United States Patent
Kotschy et al.

(10) Patent No.: US 11,046,681 B2
(45) Date of Patent: Jun. 29, 2021

(54) SUBSTITUTED PIPERIDINES FOR THE TREATMENT OF CANCER

(71) Applicants: LES LABORATOIRES SERVIER, Suresnes (FR); VERNALIS (R&D) LTD, Winnersh (GB)

(72) Inventors: András Kotschy, Törőbálint (HU); Csaba Wéber, Pilisszentlászló (HU); Attila Vasas, Fót (HU); Balázs Molnár, Isaszeg (HU); Árpád Kiss, Budapest (HU); Alba Macias, Cambridgeshire (GB); James Brooke Murray, Linton (GB); Elodie Lewkowicz, Paris (FR); Olivier Geneste, Rueil-Malmaison (FR); Maïa Chanrion, Issy les Moulineaux (FR); Didier Demarles, Checy (FR)

(73) Assignees: LES LABORATOIRES SERVIER, Suresnes (FR); VERNALIS (R&D) LTD, Winnersh (GB)

( * ) Notice: Subject to any disclaimer, the term of this patent is extended or adjusted under 35 U.S.C. 154(b) by 116 days.

(21) Appl. No.: 16/306,933

(22) PCT Filed: Jun. 9, 2017

(86) PCT No.: PCT/EP2017/064067
§ 371 (c)(1),
(2) Date: Dec. 4, 2018

(87) PCT Pub. No.: WO2017/212012
PCT Pub. Date: Dec. 14, 2017

(65) Prior Publication Data
US 2019/0144448 A1     May 16, 2019

(30) Foreign Application Priority Data
Jun. 10, 2016 (FR) ...................... 1655392

(51) Int. Cl.
| | |
|---|---|
| A61K 31/4545 | (2006.01) |
| C07D 211/32 | (2006.01) |
| C07D 471/04 | (2006.01) |
| C07D 487/04 | (2006.01) |
| C07D 495/04 | (2006.01) |
| A61P 37/02 | (2006.01) |
| A61P 35/00 | (2006.01) |
| A61K 45/06 | (2006.01) |

(52) U.S. Cl.
CPC ............ *C07D 471/04* (2013.01); *A61P 35/00* (2018.01); *A61P 37/02* (2018.01); *C07D 487/04* (2013.01); *C07D 495/04* (2013.01); *A61K 45/06* (2013.01)

(58) Field of Classification Search
CPC .. C07D 471/04; C07D 487/04; C07D 211/32; A61P 37/03; A61P 35/00; A61K 31/4545

USPC ........................................ 514/316; 546/314
See application file for complete search history.

(56) References Cited

FOREIGN PATENT DOCUMENTS

| | | |
|---|---|---|
| WO | WO 2013030218 | 0/2013 |
| WO | WO 2008/108957 | 9/2008 |
| WO | WO 292008108957 | 9/2008 |

OTHER PUBLICATIONS

Kemp, Mark. Progress in Medicinal Chemistry, vol. 55, 2016, 149-192. (Year: 2016).*
MedicineNet.com (2004) Web <http://www.medterms.com. (Year: 2004).*
International Search Report for PCT/EP2017/064067 dated Jul. 6, 2017.
Agathanggelou, et al., Blood, 2017, 130(2), 156-166.
Alonso de Vega, et al., Cell Cycle, 2014, 13(24), 3921-3926.
An, et al., Biochem Pharmacol., 2017, 131, 29-39.
Cai, et al., Hepatology, 2015, 61(5), 1603-1614.
Callegari, et al., Cell Commun Signal., 2018, 16(1), 60.
Carrà, et al., Oncotarget, 2017, 8(22), 35508-35522.
Chauhan, et al., Cancer Cell, 2012, 22, 345-358.
Chen, et al., J Biol Chem., 2015, 290(35), 21713-21723.
Cheng, et al., Nat. Commun., 2015, 6, 7023.
Cheng, et al., Oncol Rep., 2013, 29(5), 1730-1736.
Cummins, et al., Cell Cycle, 2004, 3(6), 689-692.
Felle, et al., Nucleic Acids Res., 2011, 39(19), 8355-8365.
Franqui-Machin, et al., J Clin Invest., 2018, 128(7), 2877-2893.
Fu, et al., Onco Targets Ther., 2019, 12, 609-617.
He, et al., J Biol Chem., 2019, pii: jbc.RA119.010724.
Hernández-Pérez, et al., Oncogene, 2017, 36(33), 4802-4809.
Hu, et al., Mol Carcinog., 2019, 58(1), 42-54.
Jin, et al., Clin Cancer Res., 2019, 25(1), 222-239.
Li et al., Nature, 2002, 416(6881), 648-653.
Li, et al., Mol Cell, 2004, 13(6), 879-886.

(Continued)

*Primary Examiner* — Douglas M Willis
(74) *Attorney, Agent, or Firm* — Hueschen and Sage

(57) ABSTRACT

Compounds of formula (I):

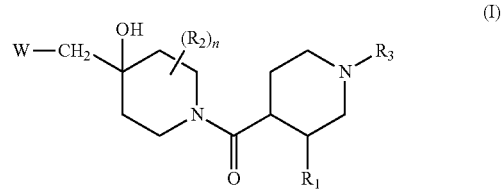

wherein $R_1$, $R_2$, $R_3$, n and W are as defined in the description.
Medicinal products containing the same which are useful in treating conditions requiring pro-apoptotic and/or anti-proliferative agents.

17 Claims, No Drawings

(56) References Cited

OTHER PUBLICATIONS

Liu, et al., EMBO Rep., 2019, e48597.
Ma, et al., Onco Targets Ther., 2016, 9, 1559-1569.
Malapelle, et al., Lung Cancer, 2017, 107, 41-49.
Masuya, et al., J Pathol., 2006, 208(5), 724-732.
Morotti, et al., Eur J Haematol., 2015, 94(4), 318-321.
Morra et al., Oncotarget, 2015, 6(14), 12697-12709.
Morra et al., Oncotarget, 2017, 8(19), 31815-31829.
Morra, et al., J Exp Clin Cancer Res., 2019, 38(1), 90.
Noguera, et al., Leukemia, 2013, 27(5), 1037-1043.
Novellasdemunt, et al., Cell Rep., 2017, 21(3), 612-627.
Qin et al., Oncotarget, 2016, 7(47), 77096-77109.
Qin, et al., J Cell Biochem., 2011, 112(2), 439-444.
Shan, et al., Signal Transduct Target Ther., 2018, 3, 29.
Sho, et al., J Surg Oncol., 2017, 116(8), 996-1004.
Song, et al., Nature, 2008, 455, 813-817.
Su, et al., J Ciin Invest., 2018, 128(10), 4280-4296.
Son, et al., Nat Commun., 2019, 10(1), 411.
Tavana, et al., Nat Med., 2016, 22(10), 1180-1186.
van der Knapp, et al., Molecular Cell, vol. 17, Mar. 4, 2005, 695-707.
van Loosdregt, et al., Immunity, 2013, 39, 259-271.
Varol, et al., Exp Biol Med, 2015, 240(5), 624-630.
Vishnoi, et al., Cancer Res. 2018, 78(18), 5349-5362.
Wang et al., EBioMedicine. 2016, 13, 99-112.
Wang et al., J. Clin. Invest., 2016, 126(6), 2205-2220.
Wang et al., Med Sci Monit., 2018, 24, 1742-1750.
Wang et al., PLoS One, 2017, 12(12), e0189744.
Wang, et al., Cell Physiol Biochem., 2017, 43(5), 1755-1766.
Xia et al., Mol Oncol., 2020, doi: 10.1002/1878-0261.12641.
Xia, et al., Cancer Lett., 2019, 465, 118-128.
Yamaguchi, et al., Sci Rep., 2017, 7(1), 55.
Yao, et al., J Leukoc Biol., 2018, 104(6), 1105-1115.
Zhang et al., Nat Cell Biol., 2014, 16(9), 864-875.
Zhang et al., Tohoku J Exp Med., 2016, 239(3), 165-175.
Zhang, et al., Int J Biochem Cell Biol., 2016, 79, 209-221.
Zhao, et al., Tumor Biol., 2015, 36, 1721-1729.
Zhu, et al., Cell Cycle, 2015, 14(9), 1413-1425.
Zlatanou, et al., Oncogene, 2016, 35(8), 965-976.

\* cited by examiner

SUBSTITUTED PIPERIDINES FOR THE TREATMENT OF CANCER

The present invention relates to new piperidinyl derivatives, to a process for their preparation and to pharmaceutical compositions containing them.

The compounds of the present invention are new and have very valuable pharmacological characteristics in the field of apoptosis and oncology.

Ubiquitination is a process controlling essential cellular functions such as protein turnover and homeostasis, protein activation and localisation. Ubiquitin is a 76 amino acids polypeptide which is covalently attached to postranslationnaly modified protein substrates via an isopeptide bond. Deubiquinating enzymes (DUBs) are in majority cysteine proteases that cleave the ubiquitin-ubiquitin bond or ubiquitin-protein bond at the Cter glycine of Ubiquitin. Approximately 100 DUBs regulate the thousands ubiquitinated proteins and then some redundancy of deubiquitinase substrates regulation are observed.

Dysregulation of DUBs have been associated with several diseases such as neurodegenerative and infectious diseases (Edelman et al., *Expert Rev. Mol. Med.* 2011, 13, 1-17) and human malignancies (Pal et al., *Cancer Res.* 2014, 74, 4955-4966). Accordingly, overexpression of DUBs or increase of their activity have been associated to numerous types of cancers (Luise et al., *Plos One* 2011, 6, e15891; Rolen et al., *Mol. Carcinog.* 2006, 45, 260-269) and poor prognosis.

Ubiquitin Specific Protease 7 (USP7), also known as Herpes-virus-Associated Ubiquitin-Specific Protease (HAUSP), belongs to the deubiquitinating family. USP7 has been reported to stabilize numerous oncogenes involved in survival and proliferations via cell cycle progression, apoptosis, DNA repair, DNA replication and epigenetic factors regulation (Nicholson et al., *Cell Biochem. Biophys.* 2011, 60, 61-68). In addition, USP7 has been shown to regulate immune response via inflammation and Treg modulation (Van Loosdregt et al., *Immunity* 2013, 39, 259-27; Colleran et al., *Proc. Natl. Acad. Sci. USA* 2013, 110, 618-623). USP7 has also been implicated in other pathologic states such as neurodevelopmental disorder (Hao et al., *Mol. Cell* 2015, 59, 956-969) and viral infection (Holowaty et al., *Biochem. Soc. Trans.* 2004, 32, 731-732).

USP7 overexpression has been associated with late stages of cancers and poor prognosis in lung, neuroblastoma, myeloma, prostate, colon and breast cancers. Although some inhibitors have been published in the literature, most of them were not selective and, to date, no USP7 inhibitors have entered the clinic (Kemp et al., *Progress in Medicinal Chemistry* 2016, 55, 149-192). There is, therefore, a therapeutic need for compounds that inhibit the activity of the protein USP7.

In addition to being new, the compounds of the present invention have pro-apoptotic and/or anti-proliferative properties making it possible to use them in pathologies involving a defect in apoptosis, such as, for example, in the treatment of cancer and of immune and auto-immune diseases.

The present invention relates more especially to compounds of formula (I):

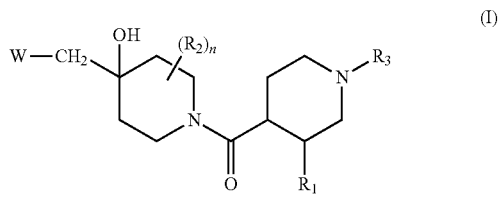

wherein:
$R_1$ represents an aryl group or a heteroaryl group,
$R_2$ represents a hydrogen atom or a halogen atom,
$R_3$ represents a hydrogen atom, a linear or branched $(C_1-C_6)$alkyl group, a linear or branched halo$(C_1-C_6)$ alkyl, a —C(O)—$R_8$ group, a —C(O)—$OR_8$ group,
n is an integer equal to 0, 1 or 2,
W represents the group

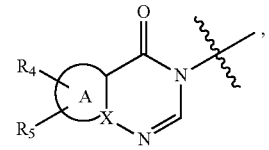

wherein:
A represents a heteroaryl ring,
X represents a carbon atom or a nitrogen atom,
$R_4$ represents a hydrogen atom, a halogen atom, a linear or branched $(C_1-C_6)$alkyl group, a linear or branched $(C_2-C_6)$alkenyl group, a linear or branched $(C_2-C_6)$ alkynyl group, a —$Y_1$—$NR_6R_7$ group, a —$Y_1$— $OR_6$ group, a linear or branched halo$(C_1-C_6)$alkyl group, an oxo group, a —$Y_1$-$Cy_1$ group, a -$Cy_1$—$R_7$ group, a -$Cy_1$—$OR_7$ group, or a —$Y_1$—$NR_6$—C (O)—$R_7$ group,
$R_5$ represents a hydrogen atom, a halogen atom, a linear or branched $(C_1-C_6)$alkyl group, a cyano group, or a -hydroxy$(C_1-C_6)$alkyl group,
$R_6$ represents a hydrogen atom, a linear or branched $(C_1-C_6)$alkyl group, or a —$Y_2$—Si$[(C_1-C_4)$alkyl$]_3$ group,
$R_7$ represents a hydrogen atom, a linear or branched $(C_1-C_6)$alkyl group, or a —$Y_2$-$Cy_2$ group,
$Y_1$ and $Y_2$ independently of one another represent a bond or a linear or branched $(C_1-C_4)$alkylene group,
$R_8$ represents a hydrogen atom or a linear or branched $(C_1-C_6)$alkyl group,
$Cy_1$ and $Cy_2$ independently of one another, represent a cycloalkyl group, a heterocycloalkyl group, an aryl group, or a heteroaryl group,
it being understood that:
"aryl" means a phenyl, naphthyl, or indanyl group,
"heteroaryl" means any mono- or fused bi-cyclic group composed of from 5 to 10 ring members, having at least one aromatic moiety and containing from 1 to 3 heteroatoms selected from oxygen, sulphur and nitrogen,
"cycloalkyl" means any mono- or fused bi-cyclic non-aromatic carbocyclic group containing from 3 to 7 ring members,
"heterocycloalkyl" means any non-aromatic mono- or fused bi-cyclic group containing from 3 to 10 ring members, and containing from 1 to 3 heteroatoms selected from oxygen, sulphur and nitrogen, it being possible for the aryl, heteroaryl, cycloalkyl and heterocycloalkyl groups so defined to be substituted by from 1 to 4 groups selected from linear or branched $(C_1-C_6)$alkyl, linear or branched $(C_2-C_6)$alkenyl, linear or branched $(C_2-C_6)$alkynyl, linear or branched halo$(C_1-C_6)$alkyl, —Y—OR', —$Y_1$—NR'R", —$Y_1$—S(O)$_m$—R', oxo (or N-oxide where appropriate), nitro, cyano, —C(O)—R', —C(O)—OR', —O—C(O)—R', —C(O)—NR'R", —$Y_1$—NR'—C(O)—R", —$Y_1$—NR'—C(O)—OR", halogen, cyclopropyl, and pyridinyl which can be substituted by a linear or branched $(C_1-C_6)$alkyl group, it being understood that R' and R" independently of one another represent a hydrogen atom, a linear or branched $(C_1-C_6)$alkyl group, a linear or branched $(C_2-C_6)$alkenyl group, a linear or branched $(C_1-C_6)$alkoxy group, a linear or branched halo$(C_1-C_6)$alkyl, a linear or branched hydroxy$(C_1-C_6)$alkyl group, a linear or branched $(C_1-C_6)$alkoxy$(C_1-C_6)$alkyl group, a phenyl group, a cyclopropylmethyl group, a tetrahydropyranyl group, or the substituents of the pair (R', R") form together with the nitrogen atom carrying them a non-aromatic ring composed of from 5 to 7 ring members, which may contain in addition to the nitrogen a second heteroatom selected from oxygen and nitrogen, it being understood that the nitrogen in question may be substituted by from 1 to 2 groups representing a hydrogen atom, or a linear or branched $(C_1-C_6)$alkyl group, and it being understood that m is an integer equal to 0, 1 and 2, their enantiomers, diastereoisomers, and addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

Among the heteroaryl groups there may be mentioned, without implying any limitation, pyrrolyl, furyl, thienyl, thiazolyl, isothiazolyl, oxazolyl, isoxazolyl, pyrazolyl, imidazolyl, pyridinyl, pyrazinyl, pyridazinyl, pyrimidinyl, pyridinonyl, indolyl, dihydroindolyl, dihydroisoindolyl, indazolyl, dihydrocyclopentathienyl, benzothienyl, tetrahydrobenzothienyl, benzofuranyl, imidazopyridinyl, benzotriazolyl, benzodioxolyl, dihydrobenzodioxinyl, quinolinyl, isoquinolinyl, tetrahydroquinolinyl, tetrahydroisoquinolinyl, quinoxalinyl, dihydroquinoxalinyl, dihydrothienodioxinyl, quinazolinonyl, pyrrolopyridazinyl, dihydropyrrolizinyl, tetrahydroindolizinyl, etc.

Among the cycloalkyl groups there may be mentioned, without implying any limitation, cyclopropyl, cyclobutyl, cyclopentyl, cyclohexyl, etc.

Among the heterocycloalkyl groups there may be mentioned, without implying any limitation, pyrrolidinyl, tetrahydropyranyl, piperidinyl, piperazinyl, morpholinyl, etc.

In another embodiment of the invention, W advantageously represents the group

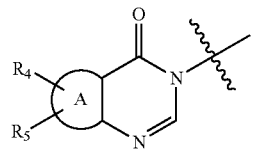

wherein $R_4$, $R_5$ and A are as defined for formula (I).

More especially,

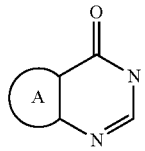

represents

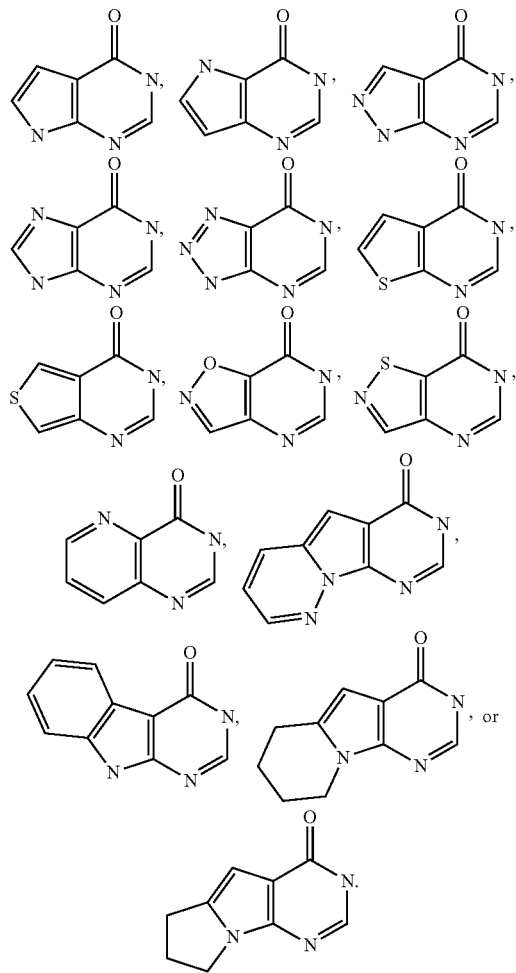

More particularly,

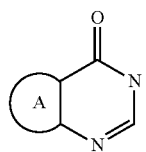

represents

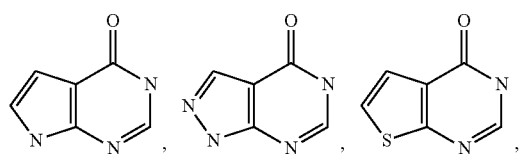

Advantageously,

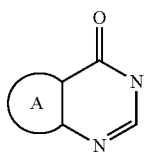

represents

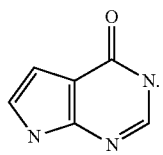

In another embodiment of the invention, W advantageously represents the group

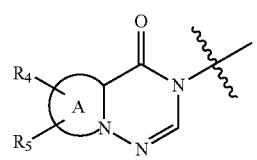

wherein $R_4$, $R_5$ and A are as defined for formula (I).

More especially,

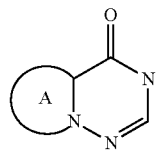

represents

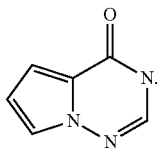

$R_1$ advantageously represents a phenyl group.

Advantageously, the compounds of formula (I) display a trans configuration as follows:

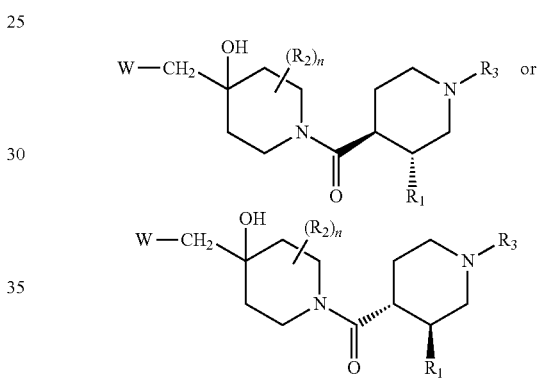

More preferably, the compounds of formula (I) display a trans configuration as follows:

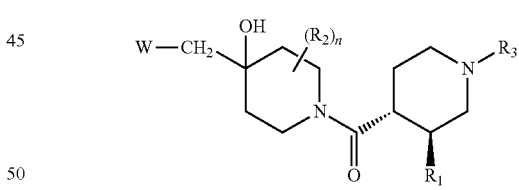

Preferably, $R_2$ represents a hydrogen atom.

In some preferred embodiment of the invention, $R_3$ represents a hydrogen atom, a methyl group, a —$CH_2$—$CH(CH_3)_2$ group, a —$CH_2$—$CF_3$ group, a —$C(O)$—$CH_3$ group, a —$C(O)$—$CH(CH_3)_2$ group, a —$C(O)$—$CH_2$—$C(CH_3)_3$ group, or a —$C(O)$—$OC(CH_3)_3$ group.

In the preferred compounds of the invention, $R_4$ represents a hydrogen atom, a linear or branched ($C_1$-$C_6$)alkyl group, a linear or branched ($C_2$-$C_6$)alkenyl group, a linear or branched ($C_2$-$C_6$)alkynyl group, a —$Y_1$—$NR_6R_7$ group, a —$Y_1$—$OR_6$ group, a linear or branched halo($C_1$-$C_6$)alkyl group, a —$Y_1$-$Cy_1$ group, a -$Cy_1$—$R_7$ group, or a -$Cy_1$—$OR_7$ group.

Advantageously, $Cy_1$ represents a phenyl group, a naphthyl group, a thienyl group, a thiazolyl group, a pyrazolyl group, an imidazolyl group, a pyridinyl group, a pyrimidinyl group, a pyridinonyl group, a benzodioxolyl group, a dihydrobenzodioxinyl group, a cyclopropyl group, a cyclobutyl group, or a piperidinyl group.

Advantageously, $R_5$ represents a hydrogen atom, an iodine atom, a chlorine atom, a methyl group or a —$CH_2$—OH group.

In the preferred compounds of the invention, $R_6$ represents a hydrogen atom, a methyl group, or a —$(CH_2)_2$—Si$(CH_3)_3$ group.

$R_7$ preferably represents a hydrogen atom, a methyl group, or a —$CH_2$-$Cy_2$ group. Preferably, $Cy_2$ represents a phenyl group.

Among the preferred compounds of the invention there may be mentioned:

tert-butyl (3S,4S)-4-({4-hydroxy-4-[(4-oxothieno[2,3-d]pyrimidin-3(4H)-yl)methyl]piperidin-1-yl}carbonyl)-3-phenylpiperidine-1-carboxylate;

tert-butyl (3R,4R)-4-[(4-hydroxy-4-{[4-oxo-7-(pyridin-2-yl)-4,7-dihydro-3H-pyrrolo[2,3-d]pyrimidin-3-yl]methyl}piperidin-1-yl)carbonyl]-3-phenylpiperidine-1-carboxylate;

tert-butyl (3R,4R)-4-[(4-hydroxy-4-{[7-(4-methoxyphenyl)-4-oxo-4,7-dihydro-3H-pyrrolo[2,3-d]pyrimidin-3-yl]methyl}piperidin-1-yl)carbonyl]-3-phenylpiperidine-1-carboxylate;

tert-butyl (3R,4R)-4-[(4-hydroxy-4-{[1-(4-methoxyphenyl)-4-oxo-1,4-dihydro-5H-pyrazolo[3,4-d]pyrimidin-5-yl]methyl}piperidin-1-yl)carbonyl]-3-phenylpiperidine-1-carboxylate;

tert-butyl (3R,4R)-4-[(4-{[7-(4-fluoro-3-methoxyphenyl)-4-oxo-4,7-dihydro-3H-pyrrolo[2,3-d]pyrimidin-3-yl]methyl}-4-hydroxypiperidin-1-yl)carbonyl]-3-phenylpiperidine-1-carboxylate;

tert-butyl (3R,4R)-4-[(4-{[1-(2,3-dihydro-1,4-benzodioxin-6-yl)-4-oxo-1,4-dihydro-5H-pyrazolo[3,4-d]pyrimidin-5-yl]methyl}-4-hydroxypiperidin-1-yl)carbonyl]-3-phenylpiperidine-1-carboxylate;

3-[(4-hydroxy-1-{[(3R,4R)-3-phenylpiperidin-4-yl]carbonyl}piperidin-4-yl)methyl]-7-phenyl-3,7-dihydro-4H-pyrrolo[2,3-d]pyrimidin-4-one;

5-[(4-hydroxy-1-{[(3R,4R)-3-phenylpiperidin-4-yl]carbonyl}piperidin-4-yl)methyl]-1-phenyl-1,5-dihydro-4H-pyrazolo[3,4-d]pyrimidin-4-one;

3-[(4-hydroxy-1-{[(3R,4R)-3-phenylpiperidin-4-yl]carbonyl}piperidin-4-yl)methyl]-7-(pyridin-2-yl)-3,7-dihydro-4H-pyrrolo[2,3-d]pyrimidin-4-one;

3-[(4-hydroxy-1-{[(3R,4R)-3-phenyl-1-(2,2,2-trifluoroethyl)piperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-methyl-3-phenylpiperidin-4-yl]carbonyl}piperidin-4-yl)methyl]-7-phenyl-3,7-dihydro-4H-pyrrolo[2,3-d]pyrimidin-4-one;

7-(4-fluorophenyl)-3-[(4-hydroxy-1-{[(3R,4R)-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-3-phenylpiperidin-4-yl]carbonyl}piperidin-4-yl)methyl]-7-(3-methoxyphenyl)-3,7-dihydro-4H-pyrrolo[2,3-d]pyrimidin-4-one;

7-(4-fluorophenyl)-3-[(4-hydroxy-1-{[(3R,4R)-1-methyl-3-phenylpiperidin-4-yl]carbonyl}piperidin-4-yl)methyl]-3,7-dihydro-4H-pyrrolo[2,3-d]pyrimidin-4-one;

7-(3-chlorophenyl)-3-[(4-hydroxy-1-{[(3R,4R)-3-phenylpiperidin-4-yl]carbonyl}piperidin-4-yl)methyl]-3,7-dihydro-4H-pyrrolo[2,3-d]pyrimidin-4-one;

7-(4-chlorophenyl)-3-[(4-hydroxy-1-{[(3R,4R)-3-phenylpiperidin-4-yl]carbonyl}piperidin-4-yl)methyl]-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

3-[(4-hydroxy-1-{[(3R,4R)-1-methyl-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

7-(3-chlorophenyl)-3-[(4-hydroxy-1-{[(3R,4R)-1-methyl-3-phenylpiperidin-4-yl]carbonyl}piperidin-4-yl)methyl]-3,7-dihydro-4H-pyrrolo[2,3-d]pyrimidin-4-one;

7-(4-chlorophenyl)-3-[(4-hydroxy-1-{[(3R,4R)-1-methyl-3-phenylpiperidin-4-yl]carbonyl}piperidin-4-yl)methyl]-3,7-dihydro-4H-pyrrolo[2,3-d]pyrimidin-4-one;

7-(4-fluoro-3-methoxyphenyl)-3-[(4-hydroxy-1-{[(3R,4R)-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-(2-methylpropyl)-3-phenylpiperidin-4-yl]carbonyl}piperidin-4-yl)methyl]-7-phenyl-3,7-dihydro-4H-pyrrolo[2,3-d]pyrimidin-4-one;

1-(2,3-dihydro-1,4-benzodioxin-6-yl)-5-[(4-hydroxy-1-{[(3R,4R)-3-phenylpiperidin-4-yl]carbonyl}piperidin-4-yl)methyl]-1,5-dihydro-4H-pyrazolo[3,4-d]pyrimidin-4-one;

3-[(1-{[(3R,4R)-1-acetyl-3-phenylpiperidin-4-yl]carbonyl}-4-hydroxypiperidin-4-yl)methyl]-7-(4-fluorophenyl)-3,7-dihydro-4H-pyrrolo[2,3-d]pyrimidin-4-one;

(3R,4R)-4-[(4-hydroxy-4-{[1-(4-methoxyphenyl)-4-oxo-1,4-dihydro-5H-pyrazolo[3,4-d]pyrimidin-5-yl]methyl}piperidin-1-yl)carbonyl]-1,1-dimethyl-3-phenylpiperidinium;

3-[(4-hydroxy-1-{[(3R,4R)-1-(2-methylpropanoyl)-3-phenylpiperidin-4-yl]carbonyl}piperidin-4-yl)methyl]-7-phenyl-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-(3-methoxyphenyl)-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-(3-chlorophenyl)-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-(4-chlorophenyl)-3,7-dihydro-4H-pyrrolo[2,3-d]pyrimidin-4-one;

3-[(1-{[(3R,4R)-1-(2,2-dimethylpropanoyl)-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

3-[(1-{[(3R,4R)-1-(3,3-dimethylbutanoyl)-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

The invention relates also to a process for the preparation of compounds of formula (I), which process is characterized in that there is used as starting material the compound of formula (II):

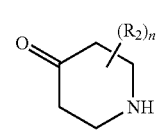

wherein $R_2$ and n are as defined for formula (I),
which is subjected to coupling with a compound of formula (III):

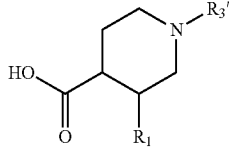
(III)

wherein $R_1$ is as defined for formula (I), and $R_3'$ represents a —C(O)—$OR_8$ group wherein $R_8$ is as defined for formula (I),
to yield the compound of formula (IV):

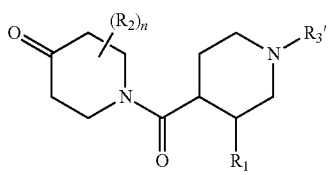
(IV)

wherein $R_1$, $R_2$, $R_3'$ and n are as defined hereinbefore,
compound of formula (IV) which is further converted to an epoxide compound of formula (V):

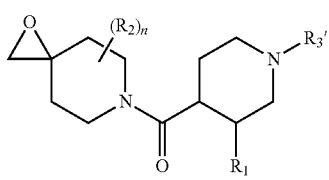
(IV)

wherein $R_1$, $R_2$, $R_3'$ and n are as defined hereinbefore,
compound of formula (V) which is further subjected to coupling with compound of formula (VI):

(VI)

wherein W is as defined for formula (I),
to yield the compound of formula (I-a), a particular case of the compounds of formula (I):

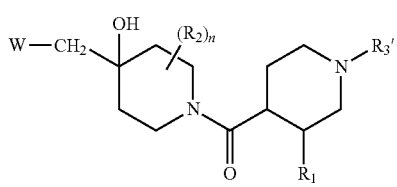
(I-a)

wherein $R_1$, $R_2$, $R_3'$, n and W are as defined hereinbefore, which compound of formula (I/a) may then, if required, be subjected to a reaction removing the $R_3'$ group,
to yield the compound of formula (I-b), a particular case of the compounds of formula (I):

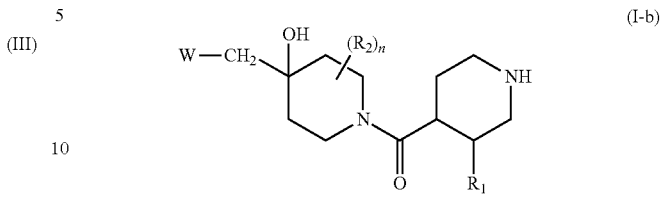
(I-b)

wherein $R_1$, $R_2$, n and W are as defined hereinbefore,
which compound of formula (I/b) may then, if required, be subjected to a coupling reaction with compound of formula $R_3''$—Cl wherein $R_3''$ represents a linear or branched ($C_1$-$C_6$)alkyl group, a linear or branched halo($C_1$-$C_6$)alkyl, or a —C(O)—$R_8$ group wherein $R_8$ is as defined for formula (I),
to yield the compound of formula (I-c), a particular case of the compounds of formula (I):

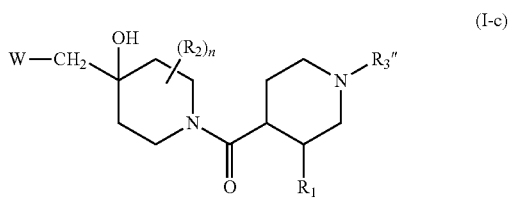
(I-c)

wherein $R_1$, $R_2$, $R_3''$, n and W are as defined hereinbefore, which compounds of formulae (I/a) to (I/c), which constitute the totality of the compounds of formula (I), may then be purified according to a conventional separation technique, which is converted, if desired, into its addition salts with a pharmaceutically acceptable acid or base and which is optionally separated into its isomers according to a conventional separation technique, it being understood that at any moment considered appropriate during the course of the process described above, some groups (hydroxy, amino . . . ) of the starting reagents or of the synthesis intermediates can be protected, subsequently deprotected and functionalized, as required by the synthesis.

The compounds of formulae (II), (III), (VI) and $R_3''$—Cl are either commercially available or can be obtained by the person skilled in the art using conventional chemical reactions described in the literature.

Pharmacological studies of the compounds of the invention have shown pro-apoptotic and/or anti-proliferative properties. The ability to reactivate the apoptotic process in cancerous cells is of major therapeutic interest in the treatment of cancers and of immune and auto-immune diseases.

Among the cancer treatments envisaged there may be mentioned, without implying any limitation, treatment of cancers of the bladder, brain, breast and uterus, chronic lymphoid leukemia, cancer of the colon, esophagus and liver, lymphoblastic leukemia, acute myeloid leukemia, lymphomas, melanomas, malignant haemopathies, myelomas, ovarian cancer, non-small-cell lung cancer, prostate cancer, pancreatic cancer and small-cell lung cancer. More especially, the compounds according to the invention will be useful in the treatment of chemo-, targeted therapy- or radio-resistant cancers.

The present invention relates also to pharmaceutical compositions comprising at least one compound of formula (I) in combination with one or more pharmaceutically acceptable excipients.

Among the pharmaceutical compositions according to the invention there may be mentioned more especially those that are suitable for oral, parenteral, nasal, per- or trans-cutaneous, rectal, perlingual, ocular or respiratory administration, especially tablets or dragdes, sublingual tablets, sachets, paquets, capsules, glossettes, lozenges, suppositories, creams, ointments, dermal gels, and drinkable or injectable ampoules.

The pharmaceutical compositions according to the invention comprise one or more excipients or carriers selected from diluents, lubricants, binders, disintegration agents, stabilisers, preservatives, absorbents, colorants, sweeteners, flavourings etc.

By Way of Non-Limiting Example there May be Mentioned:
- as diluents: lactose, dextrose, sucrose, mannitol, sorbitol, cellulose, glycerol,
- as lubricants: silica, talc, stearic acid and its magnesium and calcium salts, polyethylene glycol,
- as binders: magnesium aluminium silicate, starch, gelatin, tragacanth, methylcellulose, sodium carboxymethylcellulose and polyvinylpyrrolidone,
- as disintegrants: agar, alginic acid and its sodium salt, effervescent mixtures.

The dosage varies according to the sex, age and weight of the patient, the administration route, the nature of the therapeutic indication, or of any associated treatments, and ranges from 0.01 mg to 1 g per 24 hours in one or more administrations.

Furthermore, the present invention relates also to the combination of a compound of formula (I) with anti-cancer agents selected from genotoxic agents, mitotic poisons, anti-metabolites, proteasome inhibitors, kinase inhibitors, protein-protein interaction inhibitors, immunomodulators, E3 ligase inhibitors, chimeric antigen receptor T-cell therapy and antibodies, and also to pharmaceutical compositions comprising that type of combination and their use in the manufacture of medicaments for use in the treatment of cancer.

The combination of a compound of formula (I) with an anticancer agent may be administered simultaneously or sequentially. The administration route is preferably the oral route, and the corresponding pharmaceutical compositions may allow the instantaneous or delayed release of the active ingredients. The compounds of the combination may moreover be administered in the form of two separate pharmaceutical compositions, each containing one of the active ingredients, or in the form of a single pharmaceutical composition, in which the active ingredients are in admixture.

The compounds of formula (I) may also be used in combination with radiotherapy in the treatment of cancer.

The following Preparations and Examples illustrate the invention but do not limit it in any way.

General Procedures

All reagents obtained from commercial sources were used without further purification. Anhydrous solvents were obtained from commercial sources and used without further drying.

Flash chromatography was performed on ISCO CombiFlash Rf 200i with pre-packed silica-gel cartridges (RediSep®R$_f$ Gold High Performance).

Thin layer chromatography was conducted with 5×10 cm plates coated with Merck Type 60 F254 silica-gel.

Microwave heating was performed in an Anton Parr MonoWave or CEM Discover® instrument.

Preparative HPLC purifications were performed on an HANBON NP7000 Liquid Chromatography system with a Gemini-NX® 5 µM C18, 250 mm×50 mm i.d. column running at a flow rate of 99.9 mL min$^{-1}$ with UV diode array detection (210-400 nm) using 5 mM aqueous NH$_4$HCO$_3$ solution and MeCN as eluents unless specified otherwise.

Analytical LC-MS: The compounds of the present invention were characterized by high performance liquid chromatography-mass spectroscopy (HPLC-MS) on Agilent HP1200 with Agilent 6140 quadrupole LC/MS, operating in positive or negative ion electrospray ionisation mode. Molecular weight scan range is 100 to 1350. Parallel UV detection was done at 210 nm and 254 nm. Samples were supplied as a 1 mM solution in ACN, or in THF/H$_2$O (1:1) with 5 µL loop injection. LCMS analyses were performed on two instruments, one of which was operated with basic, and the other with acidic eluents.

Basic LCMS: Gemini-NX, 3 µm, C18, 50 mm×3.00 mm i.d. column at 23° C., at a flow rate of 1 mL min$^{-1}$ using 5 mM ammonium bicarbonate (Solvent A) and acetonitrile (Solvent B) with a gradient starting from 100% Solvent A and finishing at 100% Solvent B over various/certain duration of time.

Acidic LCMS: ZORBAX Eclipse XDB-C18, 1.8 µm, 50 mm×4.6 mm i.d. column at 40° C., at a flow rate of 1 mL min$^{-1}$ using 0.02% v/v aqueous formic acid (Solvent A) and 0.02% v/v formic acid in acetonitrile (Solvent B) with a gradient starting from 100% Solvent A and finishing at 100% Solvent B over various/certain duration of time.

$^1$H-NMR measurements were performed on Bruker Avance III 500 MHz spectrometer and Bruker Avance III 400 MHz spectrometer, using DMSO-d$_6$ or CDCl$_3$ as solvent. 1H NMR data is in the form of delta values, given in part per million (ppm), using the residual peak of the solvent (2.50 ppm for DMSO-d$_6$ and 7.26 ppm for CDCl$_3$) as internal standard. Splitting patterns are designated as: s (singlet), d (doublet), t (triplet), q (quartet), quint (quintet), sept (septet), m (multiplet), brs (broad singlet), brd (broad doublet), brt (broad triplet), brq (broad quartet), brm (broad multiplet), vbrs (very broad singlet), dd (doublet of doublets), td (triplet of doublets), dt (doublet of triplets), dq (doublet of quartet), ddd (doublet of doublet of doublets), dm (doublet of multiplets), tm (triplet of multiplets), qm (quartet of multiplets).

Combination gas chromatography and low resolution mass spectrometry were performed on Agilent 6850 gas chromatograph and Agilent 5975C mass spectrometer using 15 m×0.25 mm column with 0.25 µm HP-5MS coating and helium as carrier gas. Ion source: EI$^+$, 70 eV, 230° C., quadrupole: 150° C., interface: 300° C.

HRMS were determined on a Shimadzu IT-TOF, ion source temperature 200° C., ESI+/−, ionization voltage: (+−)4.5 kV. Mass resolution min. 10000.

Elementary analyses were performed on a Thermo Flash EA 1112 Elemental Analyzer.

| List of abbreviations | |
|---|---|
| Abbreviation | Name |
| abs. | absolute |
| aq. | aqueous |
| Ar | argon |
| AtaPhos*PdCl$_2$ | bis(di-tert-butyl(4-dimethylaminophenyl)phosphine) dichloropalladium(II) |
| Boc | tert-butoxycarbonyl |
| cc. | concentrated |

| List of abbreviations | |
|---|---|
| Abbreviation | Name |
| DCM | dichloromethane |
| DEE | diethyl ether |
| DIPO | diisopropyl oxide |
| disp. | dispersion |
| DMEDA | N,N'-dimethylethylenediamine |
| DMF | dimethylformamide |
| EDC•HCl | N-(3-dimethylaminopropyl)-N'-ethylcarbodiimide hydrochloride |
| EEO | ethyl ethanoate |
| eq. | equivalent |
| iPr$_2$NH | isopropylamine |
| LC | liquid chromatography |
| LDA | lithium diisopropylamide |
| MeCN | acetonitrile |
| MSM | methylsulfinylmethane |
| MTBE | tert-butyl methylether |
| PDO | p-dioxane |
| Pd$_2$(dba)$_3$ | tris(dibenzylideneacetone)dipalladium |
| r.t. | room temperature |
| sat. | saturated |
| TFA | trifluoroacetic acid |
| THF | tetrahydrofuran |

General Procedure 1

Step 1:

To a stirred solution of 4-chloro-7H-pyrrolo[2,3-d]pyrimidine (Preparation R1a; 1.84 g, 12 mmol, 1 eq.) in abs. DMF (15 ml) sodium-hydride (720 mg, 60% disp. in mineral oil, 18 mmol, 1.5 eq.) was added, and stirred for 10 minutes at r.t. under Ar. Alkylating agent (13.18 mmol) was added to the reaction mixture and stirred for 1-6 hours at r.t. The mixture was poured into water (150 ml), then it was extracted with EEO (3×150 ml). The combined organic layer was washed with water, brine, dried over MgSO$_4$, and evaporated.

Step 2:

A part of this residue (1.36 mmol) and lithium-hydroxide monohydrate (571 mg, 13.62 mmol, 10 eq.) were stirred in PDO-water (40 ml, 1:1 v/v) mixture at 110° C. for 7-36 hours. The reaction mixture was neutralized with 1 N aq. HCl solution. The resulted precipitate was filtered off, washed with water and dried.

General Procedure 2

Step 1:

Preparation R1a (460 mg, 3 mmol, 1 eq.), heteroaryl/aryl-boronic acid (7.5 mmol) and copper(II)-acetate (817 mg, 4.5 mmol) were stirred in pyridine (10 ml) at 50-60° C. for 16-72 hours.

Work-Up 1:

The mixture was evaporated to Celite, purified by flash chromatography (heptane-EEO, gradient).

Work-Up 2:

The mixture was filtered, the resulted filtrate was purified by preparative LC (on C-18 Gemini-NX 5 μm column, 5 mM aqueous NH$_4$HCO$_3$-MeCN, gradient).

Step 2:

The resulted compound (1.36 mmol) and lithium-hydroxide monohydrate (571 mg, 13.62 mmol, 10 eq.) were stirred in PDO-water (40 ml, 1:1 v/v) mixture at 110° C. for 7-24 hours. The reaction mixture was neutralized with 1 N aq. HCl solution. The resulted precipitate was filtered off, washed with water and dried.

General Procedure 3

Step 1:

Preparation R1b (746 mg, 5 mmol, 1 eq.), heteroaryl/aryl-iodide (10 mmol), CuI (286 mg, 1.5 mmol, 0.3 eq.), R,R-diaminocyclohexane (171 mg, 1.5 mmol, 0.3 eq.), anhydrous K$_3$PO$_4$ (4.24 g, 20 mmol, 4 eq.) was stirred in diglyme (15 ml) for 6-16 hours at 120° C. under N$_2$ atmosphere.

Work-Up 1:

After the reaction completed, the mixture was diluted with water (200 ml) (or. 25% aq. NH$_3$) and cooled to r.t. The mixture was filtered, and washed with water (3×30 ml), aq. NH$_3$ solution (40 ml, 25%), water (3×50 ml), heptane (50 then 30 ml), dried in vacuum.

Work-Up2:

The reaction mixture was evaporated to Celite, then purified by flash chromatography (heptane:EEO, gradient).

Step 2:

The corresponding 4-methoxy-7-aryl-pyrrolo[2,3-d]pyrimidine (61.3 mmol, 1 eq.), cc. HCl aqueous solution (10 ml, ~12.2 M, 122.5 mmol, 2 eq.) and PDO (70 ml) was stirred at 100° C. for 0.5-2 hours. After the reaction completed, the mixture was partially evaporated. The formed suspension was filtered and the solid on the filter was washed with water and dried.

General Procedure 4

Step 1:

Preparation R1a (154 mg, 1 mmol, 1 eq.), di-tert-butyl-diazodicarboxylate (690 mg, 3 mmol, 3 eq.), triphenylphosphine (786 mg, 3 mmol, 3 eq.) and corresponding alcohol (3 mmol, 3 eq.) were stirred in abs. toluene (10 ml) under Ar atmosphere at 50° C. for 2 hours. The reaction mixture was evaporated, taken in THF and purified by preparative LC (on C-18 Gemini-NX 5 m column, 5 mM aqueous NH$_4$HCO$_3$-MeCN, gradient).

Step 2:

A part of this residue (4-chloro-7-aryl/alkyl-pyrrolo[2,3-d]pyrimidine) (1.36 mmol) and lithium-hydroxide monohydrate (571 mg, 13.62 mmol) were stirred in PDO-water (40 ml, 1:1 v/v) mixture at 110° C. for 7-24 hours. The reaction mixture was neutralized with 1 N aq. HCl solution. The resulted precipitate was filtered off, washed with water and dried.

General Procedure 5

Pyrimidine-4-one derivative (1 mmol), epoxide compound Preparation R1c (400.5 mg, 1 mmol, 1 eq.) and K$_2$CO$_3$ (276.4 mg, 2 mmol, 2 eq.) were stirred in DMF (5 ml) at 75° C. for 2-8 hours.

Work-Up 1:

The mixture was poured into ice-water mixture. The resulted precipitate was filtered off, washed with water, and dried.

Work-Up 2:

The reaction mixture was filtered, the solid was washed with DMF. The resulted filtrate was purified by preparative LC (on C-18 Gemini-NX 5 μm column, 5 mM aqueous NH$_4$HCO$_3$-MeCN, gradient).

General Procedure 6

Compound obtained in General Procedure 5 (~1 mmol) was stirred in aq. HCl solution (1 N, 10 ml, 10 mmol, 10 eq.) and PDO (5 ml) for 1-3 hours at 75° C.

Work-Up 1:

The mixture was cooled to about 0-5° C. with ice bath and the white precipitate was filtered off, dried in vacuum (resulted HCl salt).

Work-Up2:

The mixture was totally evaporated, and was used to the further step (resulted HCl salt).

Work-Up3:

The mixture was purified by preparative LC (on C-18 Gemini-NX 5 μm column, 5 mM aqueous NH$_4$HCO$_3$-MeCN, gradient, resulted as free base).

General Procedure 7

Compound obtained in General Procedure 6 (1 mmol, 1 eq.), alkyl-X (1 mmol, 1 eq.) and K$_2$CO$_3$ (483 mg, 3.5 mmol, 3.5 eq.) were stirred in DMF (10 ml) at r.t. for 4-16 hours.

Work-Up 1:

The mixture was poured into ice-water mixture. The resulted precipitate was filtered off, washed with water, and dried.

Work-Up2:

The mixture was filtered and the filtrate was injected to preparative LC (on C-18 Gemini-NX 5 μm column, 5 mM aqueous NH$_4$HCO$_3$-MeCN, gradient).

General Procedure 8

Compound obtained in General Procedure 6 (2.7 mmol), EDC.HCl (1.183 g, 6.172 mmol) and corresponding carboxylic acid (2.7 mmol) were stirred in pyridine (25 ml) at r.t. for 16 hours.

Work-Up 1:

The reaction mixture was evaporated, the residue was taken in DMF and injected to preparative LC (on C-18 Gemini-NX 5 μm column, 5 mM aqueous NH$_4$HCO$_3$-MeCN, gradient).

Work-Up2:

The reaction mixture was evaporated and the residue was trituated with water. The resulted solid was filtered off.

Preparation R1b:
4-methoxy-7H-pyrrolo[2,3-d]pyrimidine

Preparation R1a (100 g, 0,651 mol, 1 eq.), NaOH (31.26 g, 0,781 mol, 1.2 eq.) and MeOH (400 ml) was stirred at 90° C. for 24 hours. The mixture was quenched with water (1200 ml) and cooled to r.t. with ice bath. The mixture was stirred for 30 minutes, and filtered through a glass filter. The precipitate was washed with water (3×100 ml) then dried and Preparation R1b is obtained as white solid. HRMS calculated for C$_7$H$_7$N$_3$O: 149.0589; found 150.0667 [(M+H)$^+$ form].

$^1$H-NMR (400 MHz, MSM-d$_6$): δ=12.02 (vbrs, 1H), 8.37 (s, 1H), 7.35 (d, 1H), 6.47 (d, 1H), 4.02 (s, 3H).

$^{13}$C-NMR (100 MHz, MSM-d$_6$): δ ppm 162.6, 152.9, 150.8, 124.6, 104.8, 98.3, 53.7.

Preparation R1c: tert-butyl (3R,4R)-4-(2-oxa-6-azaspiro[2.5]octane-6-carbonyl)-3-phenyl-piperidine-1-carboxylate Step 1: tert-butyl (3R,4R)-4-(4-oxopiperidine-1-carbonyl)-3-phenyl-piperidine-1-carboxylate 4-piperidone hydrochloride hydrate (0.969 g, 6.3 mmol), EDC.HCl (3.623 g, 18.9 mmol) and (3R,4R)-1-tert-butoxycarbonyl-3-phenyl-piperidine-4-carboxylic acid (1.928 g, 6.3 mmol) were dissolved in pyridine (10 mL) and stirred at r.t. for 16 hours. The reaction mixture was evaporated to Celite, purified by flash chromatography (DCM:MeOH, gradient) to give the product of the title. HRMS calculated for C$_{22}$H$_{30}$N$_2$O$_4$: 386.2206; found 409.2093 [(M+Na)$^+$ form].

$^1$H-NMR (500 MHz, MSM-d$_6$): δ=1.42 (s, 9H), 4.14-1.50 (m, 16H), 7.32-7.15 (m, 5H).

Step 2: Preparation R1c tert-Butyl (3R,4R)-4-(4-oxopiperidine-1-carbonyl)-3-phenylpiperidine-1-carboxylate) (60 g, 155 mmol 1 eq.) and trimethylsulfoxonium-iodide (85.41 g, 388 mmol, 2.5 eq.) was charged into a round bottom flask and dissolved/suspended in MeCN (150 ml) and MTBE (150 ml). NaOH (15.5 g, 388 mmol, 2.5 eq.) was dissolved in water (21.6 ml) (~40% solution). The aq. NaOH solution was added to the mixture and stirred at 60° C. for 2 hours. After the reaction completed, the mixture was cooled to r.t., filtered through a Celite bed, the filter cake was washed with MTBE (2×60 ml). Water (150 ml) was added to the organic layer and after extraction the layers were separated. The aq. layer was extracted with further MTBE (2×60 ml). The combined organic layers were dried over MgSO$_4$, and after filtration evaporated to give Preparation R1c as beige solid foam. HRMS calculated for C$_{23}$H$_{32}$N$_2$O$_4$: 400.2362; found 423.2247 [(M+Na)$^+$ form].

$^1$H-NMR (500 MHz, MSM-d$_6$): δ=1.41 (s, 9H), 1.79-0.86 (m, 6H), 2.61-2.51 (m, 2H), 4.16-2.73 (m, 10H), 7.33-7.18 (m, 5H).

Preparation R2b: 7-(pyridin-2-yl)-3H,4H,7H-pyrrolo[2,3-d]pyrimidin-4-one

Using General Procedure 3 starting from Preparation R1b and 2-iodopyridine as reagents, Preparation R2b was obtained. HRMS calculated for C$_{11}$H$_8$N$_4$O: 212.0698; found 213.0774 [(M+H)$^+$ form].

$^1$H-NMR (500 MHz, MSM-d6): δ (ppm) 12.29 (s, 1H), 8.55 (dd, 1H), 8.47 (dd, 1H), 8.06 (brs, 1H), 8.03 (t, 1H), 7.9 (d, 1H), 7.4 (t, 1H), 6.7 (d, 1H).

$^{13}$C-NMR (125 MHz, MSM-d6): δ (ppm) 149.1, 145, 139.4, 122.5, 122, 116.9, 104.

$^{15}$N-NMR (50.6 MHz, MSM-d6): δ (ppm) 171.2.

Preparation R2c: 7-(4-methoxyphenyl)-3H,4H,7H-pyrrolo[2,3-d]pyrimidin-4-one

Using General Procedure 3 starting from Preparation R1b and 4-iodoanisole as reagents, Preparation R2c was obtained. HRMS calculated for C$_{13}$H$_{11}$N$_3$O$_2$: 241.0851; found 242.0929 [(M+H)$^+$ form].

$^1$H-NMR (500 MHz, MSM-d6): δ (ppm) 12.04 (brs, 1H), 7.92 (d, 1H), 7.58 (dd, 1H), 7.4 (d, 1H), 7.08 (d, 1H), 6.65 (d, 1H), 3.81 (s, 3H).

$^{13}$C-NMR (125 MHz, MSM-d6): δ (ppm) 158.8, 158.8, 147.3, 144.4, 130.9, 126.1, 124.4, 114.8, 109.4, 103.1, 55.9.

Preparation R2e: 7-(4-fluoro-3-methoxyphenyl)-3H,4H,7H-pyrrolo[2,3-d]pyrimidin-4-one Using General Procedure 3 starting from Preparation R1b and 1-fluoro-4-iodo-2-methoxybenzene as reagents, Preparation R2e was obtained. HRMS calculated for C$_{13}$H$_{10}$N$_3$O$_2$F: 259.0757; found 260.0818 [(M+H)$^+$ form].

$^1$H-NMR (500 MHz, MSM-d6): δ (ppm) 12.1 (s, 1H), 7.95 (s, 1H), 7.51 (d, 1H), 7.48 (dd, 1H), 7.38 (dd, 1H), 7.27 (ddd, 1H), 6.68 (d, 1H), 3.9 (s, 3H).

$^{13}$C-NMR (125 MHz, MSM-d6): δ (ppm) 144.7, 124.5, 117, 116.5, 111, 103.4, 56.8.

Preparation R2g: 7-methyl-3H,4H,7H-pyrrolo[2,3-d]pyrimidin-4-one

Using General Procedure 1 starting from Preparation R1a and iodomethane as alkylating agent, Preparation R2g was obtained. HRMS calculated for C$_7$H$_7$N$_3$O: 149.0589; found 150,0668 [(M+H)$^+$ form].

¹H-NMR (500 MHz, MSM-d6): δ (ppm) 11.85 (brs, 1H), 7.88 (brs, 1H), 7.09 (d, 1H), 6.44 (d, 1H), 3.70 (m, 1H).
¹³C-NMR (125 MHz, MSM-d6): δ (ppm) 158.7, 147.7, 143.8, 125.1, 108.1, 101.7, 31.8.

Preparation R2h: 7-ethyl-3H,4H,7H-pyrrolo[2,3-d]pyrimidin-4-one

Using General Procedure 1 starting from Preparation R1a and iodoethane as reagents, Preparation R2h was obtained. HRMS calculated for $C_8H_9N_3O$: 163.0746; found 164.0823 [(M+H)⁺ form].
¹H-NMR (500 MHz, MSM-d6): δ (ppm) 11.38 (brs., 1H), 7.87 (d, J=2.0 Hz, 1H), 7.16 (d, J=3.4 Hz, 1H), 6.45 (d, J=3.4 Hz, 1H), 4.14 (q, J=7.1 Hz, 2H), 1.34 (t, J=7.1 Hz, 3H).

Preparation R2i: 7-(prop-2-yn-1-yl)-3H,4H,7H-pyrrolo[2,3-d]pyrimidin-4-one

Using General Procedure 1 starting from Preparation R1b (instead of Preparation R1a) and 3-bromoprop-1-yne as reagents (without the hydrolysis step), the crude methoxypyrimidine product (400 mg, 2.3 mmol) was dissolved in PDO (4 ml) and aqueous HCl solution (37%, 0.18 ml) was added. The mixture was heated for 100° C. for 30 minutes in a Schlenk tube. After cooling, DIPO (4 ml) was added to the reaction mixture and the resulted precipitate was filtered off and dried to give Preparation R2i.
HRMS calculated for $C_9H_7N_3O$: 173.0589; found 174.0665 [(M+H)⁺ form].
¹H-NMR (500 MHz, MSM-d6): δ (ppm) 11.98 (brs, 1H), 7.93 (s, 1H), 7.19 (d, 1H), 6.5 (d, 1H), 4.98 (d, 2H), 3.42 (t, 1H).
¹³C-NMR (125 MHz, MSM-d6): δ (ppm) 158.6, 147.3, 144.3, 123.6, 102.5, 79.4, 76, 34.1.

Preparation R2j: 7-cyclopropyl-3H,4H,7H-pyrrolo[2,3-d]pyrimidin-4-one

Using General Procedure 2 starting from Preparation R1a and cyclopropylboronic acid as reagents, Preparation R2j was obtained. HRMS calculated for $C_9H_9N_3O$: 175.0746; found 176.0819 [(M+H)⁺ form].
¹H-NMR (500 MHz, MSM-d6): δ (ppm) 11.88 (brs., 1H), 7.89 (brs., 1H), 7.05 (d, 1H), 6.4 (d, 1H), 3.53 (m, 1H), 1.06-0.92 (m, 4H).
¹³C-NMR (125 MHz, MSM-d6): δ (ppm) 158.7, 148.9, 143.8, 123.4, 108.8, 101.6, 27.5, 6.6.

Preparation R2k: 7-(buta-2,3-dien-1-yl)-3H,4H,7H-pyrrolo[2,3-d]pyrimidin-4-one

Using General Procedure 1 starting from Preparation R1b (instead of Preparation R1a) and 4-bromobuta-1,2-diene as reagents (without the hydrolysis step), the crude methoxypyrimidine product (300 mg, 1.65 mmol) was dissolved in PDO (4 ml) and aq. HCl solution (37%, 0.18 ml) was added. The mixture was heated for 100° C. for 30 minutes in a Schlenk tube. After cooling, the reaction mixture was evaporated to give Preparation R2k. HRMS calculated for $C_{10}H_9N_3O$: 187.0745; found 188.0821 [(M+H)⁺ form].
¹H-NMR (500 MHz, MSM-d6): δ (ppm) 11.91 (brs, 1H), 7.89 (s, 1H), 7.12 (d, 1H), 6.46 (d, 1H), 5.48 (m, 1H), 4.87 (m, 2H), 4.73 (m, 2H).
¹³C-NMR (125 MHz, MSM-d6): δ (ppm) 208.3, 158.7, 147.4, 143.9, 123.9, 108.2, 102.1, 88.3, 78.1, 43.

Preparation R2l: 7-(cyclopropylmethyl)-3H,4H,7H-pyrrolo[2,3-d]pyrimidin-4-one

Using General Procedure 1 starting from Preparation R1a and cyclopropylmethyl bromide as reagents, Preparation R2l was obtained. HRMS calculated for $C_{10}H_{11}N_3O$: 189.0902; found 190.0980 [(M+H)⁺ form].
¹H-NMR (500 MHz, MSM-d6): δ (ppm) 11.84 (s, 1H), 7.87 (s, 1H), 7.2 (d, 1H), 6.45 (d, 1H), 3.97 (d, 2H), 1.21 (m, 1H), 0.52-0.35 (m, 4H).
¹³C-NMR (125 MHz, MSM-d6): δ (ppm) 158.7, 147.3, 143.7, 124, 108.1, 101.7, 49, 12.3, 4.07.

Preparation R2m: 7-(2-methylpropyl)-3H,4H,7H-pyrrolo[2,3-d]pyrimidin-4-one

Using General Procedure 1 starting from Preparation R1a and 1-bromo-2-methylpropane as reagents, Preparation R2m was obtained. HRMS calculated for $C_{10}H_{13}N_3O$: 191.1059; found 192.1132 [(M+H)⁺ form].
¹H-NMR (500 MHz, MSM-d6): δ (ppm) 11.84 (brs, 1H), 7.86 (s, 1H), 7.12 (d, 1H), 6.45 (d, 1H), 3.92 (d, 2H), 2.1 (sept., 1H), 0.82 (d, 6H).
¹³C-NMR (125 MHz, MSM-d6): δ (ppm) 158.8, 147.7, 143.7, 124.5, 108, 101.6, 52, 29.6, 20.2.

Preparation R2n: 9-methyl-3H-pyrimido[4,5-b]indol-4-one

Preparation R1b (500 mg, 3.06 mmol) and 2,5-dimethoxytetrahydrofurane (810 mg, 6.13 mmol, d=1.02, 795 µl) in 5 ml 1,4-dioxane were heated up to 100° C. for 102 hours, then 5 ml 1N HCl was added. It was dissolved in DMF and purified by preparative LC (on C-18 Gemini-NX 5 µm column, 5 mM aqueous $NH_4HCO_3$-MeCN, gradient) to give Preparation R2n. HRMS calculated for $C_{11}H_9N_3O$: 199.0746; found 200.0827 [(M+H)⁺ form].
¹H-NMR (500 MHz, dmso-d6) δ ppm 12.33 (brs, 1H), 8.21 (s, 1H), 7.63 (dm, 1H), 7.41 (ddd, 1H), 7.29 (td, 1H), 3.86 (s, 3H)
¹³C-NMR (500 MHz, dmso-d6) δ ppm 158.5, 153.5, 148.1, 137, 124.6, 122, 121.8, 121, 110.7, 100.1, 28.5

Preparation R2o: 7-(cyclobutylmethyl)-3H,4H,7H-pyrrolo[2,3-d]pyrimidin-4-one

Using General Procedure 1 starting from Preparation R1a and (bromomethyl)cyclobutane as reagents, Preparation R2o was obtained. HRMS calculated for $C_{11}H_{13}N_3O$: 203.1059; found 204.1134 [(M+H)⁺ form].
¹H-NMR (500 MHz, MSM-d6): δ (ppm) 11.83 (brs, 1H), 7.87 (d, 1H), 7.12 (d, 1H), 6.43 (d, 1H), 4.13 (d, 2H), 2.72 (m, 1H), 1.92/1.74 (m+m, 4H), 1.82 (m, 2H).
¹³C-NMR (125 MHz, MSM-d6): δ (ppm) 143.7, 124.2, 101.7, 49.6, 36, 25.6, 18.

Preparation R2p: 7-[2-(dimethylamino)ethyl]-3H,4H,7H-pyrrolo[2,3-d]pyrimidin-4-one Using General Procedure 1 starting from Preparation R1a and 2-bromo-N,N-dimethylethylamine hydrobromide as reagents, Preparation R2p was obtained. HRMS calculated for $C_{10}H_{14}N_4O$: 206.1168; found 207.1242 [(M+H)⁺ form].

¹H-NMR (500 MHz, MSM-d6): δ (ppm) 11.84 (brs, 1H), 7.88 (brd, 1H), 7.16 (d, 1H), 6.44 (d, 1H), 4.19 (t, 2H), 2.6 (t, 2H), 2.16 (s, 6H).
¹³C-NMR (125 MHz, MSM-d6): δ (ppm) 158.7, 147.5, 143.7, 124.4, 108.1, 101.7, 59.2, 45.5, 42.6.

Preparation R2q: 7-phenyl-3H,4H,7H-pyrrolo[2,3-d]pyrimidin-4-one

Using General Procedure 3 starting from Preparation R1b and iodobenzene as reagents, Preparation R2q was obtained. HRMS calculated for $C_{12}H_9N_3O$: 211.0746; found 212.083 [(M+H)⁺ form].
¹H-NMR (500 MHz, MSM-d6): δ (ppm) 12.1 (brs, 1H), 7.95 (d, 1H), 7.71 (m, 2H), 7.54 (m, 2H), 7.5 (d, 1H), 7.4 (m, 1H), 6.69 (d, 1H).
¹³C-NMR (125 MHz, MSM-d6): δ (ppm) 158.8, 147.3, 144.6, 137.8, 129.7, 127.4, 124.6, 124.1, 109.8, 103.6.

Preparation R2s: 7-(pyrimidin-2-yl)-3H,4H,7H-pyrrolo[2,3-d]pyrimidin-4-one

Preparation R1b (300 mg, 2.011 mmol, 1 eq.), 2-chloropyrimidine (2.413 mmol, 1.2 eq.) and anhydrous $K_2CO_3$ (417 mg, 3.017 mmol, 1.5 eq.) was heated in DMF (10 ml) at 150° C. for 2 hours. The reaction mixture was filtered and purified by preparative LC (on C-18 Gemini-NX 5 μm column, 5 mM aqueous $NH_4HCO_3$-MCN, gradient) to give 4-methoxy-7-pyrimidin-2-yl-pyrrolo[2,3-d]pyrimidine.
Then the obtained product (0.633 mmol, 1 eq.), 1M HCl aqueous solution (3 ml) and PDO (60 ml) were stirred at 100° C. for 1 hour. After the reaction completed, the mixture was evaporated and purified by preparative LC (on C-18 Gemini-NX 5 m column, 5 mM aqueous $NH_4HCO_3$-MCN, gradient) to give Preparation R2cj. HRMS calculated for $C_{10}H_7N_5O$: 213.0651; found 214,0735 [(M+H)⁺ form].
¹H-NMR (500 MHz, MSM-d6): δ (ppm) 12.19 (brs, 1H), 8.94 (d, 1H), 8.01 (s, 1H), 7.78 (d, 1H), 7.54 (t, 1H), 6.71 (d, 1H).
¹³C-NMR (125 MHz, MSM-d6): δ (ppm) 159.7, 158.7, 156, 148.1, 145.2, 123.3, 120.1, 111.4, 104.5.

Preparation R2t: 6,8-dimethylpyrimido[5,4-b]indolizin-4(3H)-one

Preparation R1b (1.74 g, 11.67 mmol) was dissolved in DMF (80 ml) and cooled to 0° C. Sodium hydride (60% disp., 1.87 g, 46.67 mmol) was slowly added and the solution was stirred for 30 minutes at 0° C. Hydroxylamine-O-sulfonic acid (2.11 g, 18.67 mmol) was added to the reaction mixture and allowed to warm up to r.t. and stirred for 20 hours. Water (100 ml) was added to the reaction mixture and extracted with DCM (4×50 ml). The combined organic layers were washed with water, dried over $MgSO_4$ and evaporated.
A part of the resulted N-amino compound (300 mg, 1.83 mmol) and acetylacetone (206 μl, 201 mg 2.01 mmol) were dissolved in 5 ml acetic acid and heated up to 120° C. for 2 hours and 30 minutes, then TFA (5 ml) was added. It was heated at 120° C. for more 18 hours. Then 1 ml water and 10 ml methanol were added, then it was evaporated. The residue was purified by preparative LC (on C-18 Gemini-NX 5 μm column, 5 mM aqueous $NH_4HCO_3$-MCN, gradient) to give Preparation R2t. HRMS calculated for $C_{11}H_{10}N_4O$: 214.0855; found 215.0935 [(M+H)⁺ form].

¹H-NMR (500 MHz, dmso-d6) δ ppm 12.16 (s, 1H), 8 (s, 1H), 6.89 (s, 1H), 6.68 (d, 1H), 2.45 (d, 3H), 2.44 (s, 3H).
¹³C-NMR (500 MHz, dmso-d6) δ ppm 159.7, 152.5, 143.4, 141.2, 138.9, 127.7, 115.5, 109.8, 91.2, 21.9, 17.4.

Preparation R2u: 7-(1-methyl-1H-imidazol-4-yl)-3H,4H,7H-pyrrolo[2,3-d]pyrimidin-4-one Using General Procedure 3 starting from Preparation R1b and 4-iodo-1-methyl-1H-imidazole as reagents, Preparation R2u was obtained. HRMS calculated for $C_{10}H_9N_5O$: 215.0807; found 216.0879 [(M+H)⁺ form].
¹H-NMR (500 MHz, MSM-d6): δ (ppm) 9.24-7.3 (vbrs, 3H), 7.51 (d, 1H), 6.72 (brs, 1H), 3.77 (s, 3H).
¹³C-NMR (125 MHz, MSM-d6): δ (ppm) 121.7, 103.5, 35.
¹⁵N-NMR (50.6 MHz, MSM-d6): δ (ppm) 153.

Preparation R2v: 7-(thiophen-3-yl)-3H,4H,7H-pyrrolo[2,3-d]pyrimidin-4-one

Using General Procedure 2 starting from Preparation R1a and thiophene-3-boronic acid pinacol ester as reagents, Preparation R2v was obtained. HRMS calculated for $C_{10}H_7N_3OS$: 217.0310; found 218.0390 [(M+H)⁺ form].
¹H-NMR (500 MHz, MSM-d6): δ (ppm) 12.14 (s, 1H), 7.99 (d, 1H), 7.92 (dd, 1H), 7.71 (dd, 1H), 7.68 (dd, 1H), 7.57 (d, 1H), 6.66 (d, 1H).
¹³C-NMR (125 MHz, MSM-d6): δ (ppm) 158.6, 147, 144.8, 136.3, 127, 123.8, 123.3, 115.1, 109.5, 103.5.

Preparation R2w: 7-(thiophen-2-yl)-3H,4H,7H-pyrrolo[2,3-d]pyrimidin-4-one

Using General Procedure 3 starting from Preparation R1b and 2-iodothiophene as reagents, Preparation R2w was obtained. HRMS calculated for $C_{10}H_7N_3OS$: 217.0310; found 218.0384 [(M+H)⁺ form].
¹H-NMR (500 MHz, MSM-d6): δ (ppm) 12.2 (brs, 1H), 8.03 (s, 1H), 7.58 (d, 1H), 7.43 (dd, 1H), 7.39 (dd, 1H), 7.07 (dd, 1H), 6.69 (d, 1H).
¹³C-NMR (125 MHz, MSM-d6): δ (ppm) 158.5, 147.2, 145.3, 138.7, 126, 124.3, 122.8, 119.2, 109.4, 104.2.

Preparation R2x: 7-(2,2,2-trifluoroethyl)-3H,4H,7H-pyrrolo[2,3-d]pyrimidin-4-one Using General Procedure 1 starting from Preparation R1a and 2,2,2-trifluoroethyl trifluoromethanesulfonate as reagents, Preparation R2x was obtained. HRMS calculated for $C_8H_6N_3OF_3$: 217.0463; found 218.0543 [(M+H)⁺ form].
¹H-NMR (500 MHz, MSM-d6): δ (ppm) 12.08 (brs, 1H), 7.97 (s, 1H), 7.19 (d, 1H), 6.57 (d, 1H), 5.06 (q, 2H).
¹³C-NMR (125 MHz, MSM-d6): δ (ppm) 158.5, 148.4, 144.9, 124.7, 124.4, 108.8, 103.2, 45.1.
¹⁹F-NMR (376.5 MHz, MSM-d6): δ (ppm) −70.3.

Preparation R2v: 7-(1,3-thiazol-2-yl)-3H,4H,7H-pyrrolo[2,3-d]pyrimidin-4-one

Using General Procedure 3 starting from Preparation R1b and 2-iodothiazole as reagents, Preparation R2ck was obtained. HRMS calculated for $C_9H_6N_4OS$: 218.0262; found 219.0335 [(M+H)⁺ form].
¹H-NMR (500 MHz, MeCN-d3) δ ppm 8.5 (s, 1H), 7.62 (d, 1H), 7.52 (d, 1H), 7.22 (d, 1H), 6.51 (d, 1H).
¹³C-NMR (125 MHz, MeCN-d3) δ ppm 154.5, 137.9, 116.8, 114.8, 104.2.

Preparation R2z: 7-[3-(dimethylamino)propyl]-3H,4H,7H-pyrrolo[2,3-d]pyrimidin-4-one Using General Procedure 1 starting from Preparation R1a and 3-dimethylaminopropyl chloride hydrochloride as reagents, Preparation R2z was obtained. HRMS calculated for $C_{11}H_{16}N_4O$: 220.1324; found 221.1401 [(M+H)$^+$ form].
$^1$H-NMR (500 MHz, MSM-d6): δ (ppm) 11.84 (brs, 1H), 7.88 (s, 1H), 7.13 (d, 1H), 6.44 (d, 1H), 4.12 (t, 2H), 2.15 (t, 2H), 2.1 (s, 6H), 1.85 (p, 2H).
$^{13}$C-NMR (125 MHz, MSM-d6): δ (ppm) 158.8, 147.4, 143.8, 124.2, 108.2, 101.7, 56.4, 45.6, 43, 28.6.

Preparation R2aa: 7-(3-methylphenyl)-3H,4H,7H-pyrrolo[2,3-d]pyrimidin-4-one

Using General Procedure 3 starting from Preparation R1b and 3-iodotoluene as reagents, Preparation R2aa was obtained. HRMS calculated for $C_{13}H_{11}N_3O$: 225.0902; found 226.098 [(M+H)$^+$ form].
$^1$H-NMR (500 MHz, MSM-d6): δ (ppm) 12.08 (brs, 1H), 7.95 (d, 1H), 7.52 (brs, 1H), 7.49 (dm, 1H), 7.46 (d, 1H), 7.41 (t, 1H), 7.22 (brd., 1H), 6.67 (d, 1H), 2.39 (s, 3H).
$^{13}$C-NMR (125 MHz, MSM-d6): δ (ppm) 158.8, 147.3, 144.6, 139.2, 137.8, 129.5, 128.1, 125.2, 124.2, 121.8, 109.7, 103.5, 21.4.

Preparation R2ab: 7-(4-methylphenyl)-3H,4H,7H-pyrrolo[2,3-d]pyrimidin-4-one

Using General Procedure 3 starting from Preparation R1b and 4-iodotoluene as reagents, Preparation R2ab was obtained. HRMS calculated for $C_{13}H_{11}N_3O$: 225,0902; found 226.0987 [(M+H)$^+$ form].
$^1$H-NMR (500 MHz, MSM-d6): δ (ppm) 12.06 (brs, 1H), 7.93 (s, 1H), 7.58 (dm, 1H), 7.44 (d, 1H), 7.33 (dm, 1H), 6.66 (d, 1H), 2.37 (s, 3H).
$^{13}$C-NMR (125 MHz, MSM-d6): δ (ppm) 158.8, 147.3, 144.5, 136.8, 135.4, 130.1, 124.5, 124.1, 109.6, 103.4, 21.

Preparation R2ac: 7-benzyl-3H,4H,7H-pyrrolo[2,3-d]pyrimidin-4-one

Using General Procedure 1 starting from Preparation R1a and benzyl bromide as reagents, Preparation R2ac was obtained. HRMS calculated for $C_{13}H_{11}N_3O$: 225.0902; found 226.0986 [(M+H)$^+$ form].
$^1$H-NMR (400 MHz, MSM-d6): δ (ppm) 11.91 (brs, 1H), 7.91 (s, 1H), 7.36-7.17 (m, 5H), 7.2 (d, 1H), 6.49 (d, 1H), 5.34 (s, 2H).
$^{13}$C-NMR (100 MHz, MSM-d6): δ (ppm) 144.1, 124.3, 102.2, 48.1.

Preparation R2ad: 6-methyl-7-phenyl-3H-pyrrolo[2,3-d]pyrimidin-4-one

Using General Procedure 3 starting from Preparation R1b and iodobenzene as reagents, 4-methoxy-7-phenyl-pyrrolo[2,3-d]pyrimidine was obtained (without hydrolysis). This crude product (450 mg, 2 mmol) was dissolved in THF (18 ml) stirred at −78° C., then LDA solution (1.8 M, 1.7 ml, 3 mmol) was added. After one hour of stirring at −78° C., iodomethane (190 μl, 3 mmol) solution in THF (5 ml) was added, and continued stirring for 90 minutes. Then the reaction mixture was diluted with brine (10 ml), evaporated to Celite and purified by flash chromatography (Hexane-EEO=7-1).

The resulted crude product (400 mg, 1.6 mmol) was dissolved in cc. HCl aqueous solution (330 μl, ~12.2 M, 4 mmol) and PDO (5 ml) was stirred at 100° C. for 2 hours. After the reaction completed, the mixture was partially evaporated and the formed suspension was filtered. The solid on the filter was washed with water and dried to give Preparation R2de. HRMS calculated for $C_{13}H_{11}N_3O$: 225.0902; found 226.0985 [(M+H)$^+$ form].
$^1$H-NMR (500 MHz, MSM-d6) δ ppm 11.94 (s, 1H), 7.76 (d, 1H), 7.55 (tm, 2H), 7.49 (tm, 1H), 7.4 (dm, 2H), 6.41 (d, 1H), 2.17 (d, 3H).
$^{13}$C-NMR (125 MHz, MSM-d6) δ ppm 158.4, 143.6, 136.2, 132.6, 129.6, 128.7, 128.5, 100.9, 13.3.

Preparation R2ae: 7-(4-fluorophenyl)-3H,4H,7H-pyrrolo[2,3-d]pyrimidin-4-one

Using General Procedure 3 starting from Preparation R1b and 4-fluoroiodobenzene as reagents, Preparation R2ae was obtained. HRMS calculated for $C_{12}H_8FN_3O$: 229.0651; found 230.0714 [(M+H)$^+$ form].
$^1$H-NMR (500 MHz, MSM-d6): δ (ppm) 12.12 (brs, 1H), 7.95 (d, 1H), 7.74 (m, 2H), 7.48 (d, 1H), 7.39 (m, 2H), 6.68 (d, 1H).
$^{13}$C-NMR (125 MHz, MSM-d6): δ (ppm) 144.7, 126.8, 124.2, 116.4, 103.5.

Preparation R2ai: 6-chloro-7-phenyl-3H-pyrrolo[2,3-d]pyrimidin-4-one

Using General Procedure 3 starting from Preparation R1b and iodobenzene as reagents, 4-methoxy-7-phenyl-pyrrolo[2,3-d]pyrimidine was obtained (without hydrolysis). The crude product (394 mg, 1.75 mmol) was dissolved in THF (14 ml) stirred at −78° C., then LDA solution (1.8 M, 1.2 ml, 2.16 mmol) was added. After one hour of stirring at −78° C., hexachloroethane (632 mg, 2.63 mmol) solution in THF (5 ml) was added, and continued stirring for 90 minutes. Then the reaction mixture was diluted with brine (10 ml), evaporated to Celite and purified by flash chromatography (Hexane-EEO=9-1).

The resulted crude product (110 mg, 0.42 mmol) was dissolved in cc. HCl aqueous solution (82 μl, ~12.2 M, 1 mmol) and PDO (5 ml) was stirred at 100° C. for 2 hours. After the reaction completed, the mixture was partially evaporated and the formed suspension was filtered. The solid on the filter was washed with water and dried to give Preparation R2dh. HRMS calculated for $C_{12}H_8N_3OCl$: 245.0356; found 246.043 [(M+H)$^+$ form].
$^1$H-NMR (500 MHz, MSM-d6) δ ppm 12.16 (s, 1H), 7.88 (s, 1H), 7.6-7.52 (m, 5H), 6.78 (s, 1H).
$^{13}$C-NMR (125 MHz, MSM-d6) δ ppm 157.6, 148.2, 145.3, 101.6.

Preparation R2aj: 6-iodo-7-methyl-3H-pyrrolo[2,3-d]pyrimidin-4-one

To a stirred solution of Preparation R1a (8 g, 52.1 mmol) in abs. DMF (50 ml) was cooled down to 0° C., then sodium-hydride (3.13 g, 60% disp. in mineral oil, 78.2 mmol, 1.5 eq.) was added, and stirred for 20 minutes at r.t. under Ar. Methyl iodide (8.2 g, 57.2 mmol, d=2.28, 3.6 ml) was added to the reaction mixture and stirred for 1.5 hours at r.t. The mixture was poured into water (50 ml). Solid compound was formed, which was filtered off.

A part of the resulted N-methylated compound (500 mg, 2.98 mmol) was dissolved in 5 ml abs. THF and cooled down to −78° C. Then 2M LDA (1.7 ml, 3.4 mmol) was added dropwise. The mixture was stirred at −78° C. for 1 hour, then iodide (757 mg, 2.98 mmol) was added. The solution was allowed to warm to r.t. and stirred for 22 hours, then 5 ml water was added. Solid compound was formed and filtered off to give Preparation R2aj. HRMS calculated for $C_7H_6IN_3O$: 274.9556; found 275.9634 [(M+H)+ form].

$^1$H-NMR (500 MHz, dmso-d6) δ ppm 11.97 (s, 1H), 7.85 (s, 1H), 6.79 (s, 1H), 3.64 (s, 3H).

$^{13}$C-NMR (500 MHz, dmso-d6) δ ppm 157.3, 149.1, 144.2, 111.4, 110.3, 80.4, 33.2.

Preparation R2al: 6-iodo-7-(2-trimethylsilylethoxymethyl)-3H-pyrrolo[2,3-d]pyrimidin-4-one 233 mg (0.82 mmol) 2-[(4-chloropyrrolo[2,3-d]pyrimidin-7-yl)methoxy]ethyl-trimethyl-silane was dissolved in 4 ml dry THF and cooled down to −78° C. and 500 μL (1.8 M stock solution, 0.9 mmol, 1.1 eq.) LDA was added. The mixture was stirred under nitrogen for 40 minutes at −78° C. then 208 mg iodine (0.82 mmol, 1 eq.) was added and allowed to warm to r.t. It was stirred for 40 minutes, then water was added. The solution was extracted with EEO (2×15 ml), combined organic phase was dried (magnesium sulfate) and evaporated. The residue was purified by flash chromatography (Eluent: heptane-EEO gradient).

Resulted crude 2-[(4-chloro-6-iodo-pyrrolo[2,3-d]pyrimidin-7-yl)methoxy]ethyl-trimethyl-silane was solved in 3 ml PDO and 3 ml water and 166 mg (3.98 mmol) lithium hydroxide hydrate was added. The mixture was heated and stirred at 110° C. for 5 hours. The solution was cooled to r.t., then 1 N HCl was added till pH 3-4. Solid compound was formed, which was filted off, and washed with water, Preparation R2 μl was obtained.

HRMS calculated for $C_{12}H_{18}IN_3O_2Si$: 391.0213; found 392.0298 [(M+H)+ form].

$^1$H-NMR (500 MHz, DMSO-d6) δ ppm 12.1 (brs, 1H), 7.91 (d, 1H), 6.84 (s, 1H), 5.45 (s, 2H), 3.51 (m, 2H), 0.82 (m, 2H), −0.08 (s, 9H).

$^{13}$C-NMR (500 MHz, DMSO-d6) δ ppm 157.3, 149.9, 144.8, 112.9, 110.5, 79.3, 73.7, 66.0, 17.5.

Preparation R2am: 7-(3,4,5-trimethoxyphenyl)-3H,4H,7H-pyrrolo[2,3-d]pyrimidin-4-one Using General Procedure 3 starting from Preparation R1b and 5-iodo-1,2,3-trimethoxybenzene as reagents, Preparation R2am was obtained. HRMS calculated for $C_{15}H_{15}N_3O_4$: 301.1063; found 302.1138 [(M+H)+ form].

$^1$H-NMR (500 MHz, MSM-d6): δ (ppm) 12.07 (brs, 1H), 7.95 (d, 1H), 7.49 (d, 1H), 6.99 (s, 2H), 6.66 (d, 1H), 3.82 (s, 6H), 3.7 (s, 3H).

$^{13}$C-NMR (125 MHz, MSM-d6): δ (ppm) 144.5, 124.6, 103.2, 103, 60.6, 56.6.

Preparation R2an: 7-(3,5-dichlorophenyl)-3H,4H,7H-pyrrolo[2,3-d]pyrimidin-4-one

Using General Procedure 2 starting from Preparation R1a and 3,5-dichlorophenylboronic acid as reagents, Preparation R2an was obtained. HRMS calculated for $C_{12}H_7Cl_2N_3O$: 278.9966; found 280.0040 [(M+H)+ form].

$^1$H-NMR (500 MHz, MSM-d6): δ (ppm) 12.03 (vbrs, 1H), 8.03 (s, 1H), 7.95 (d, 2H), 7.64 (t, 1H), 7.63 (d, 1H), 6.71 (d, 1H).

$^{13}$C-NMR (125 MHz, MSM-d6): δ (ppm) 145.3, 126.7, 123.8, 122.7, 104.4.

Preparation R2ao: 7-(3-chloro-5-methoxyphenyl)-3H,4H,7H-pyrrolo[2,3-d]pyrimidin-4-one Using General Procedure 2 starting from Preparation R1a and 3-chloro-5-methoxyphenylboronic acid as reagents, Preparation R2ao was obtained. HRMS calculated for $C_{13}H_{10}ClN_3O_2$: 275.0461; found 276.0541 [(M+H)+ form].

$^1$H-NMR (400 MHz, MSM-d6): δ (ppm) 12.18 (s, 1H), 8 (d, 1H), 7.6 (d, 1H), 7.51 (t, 1H), 7.33 (t, 1H), 7.08 (t, 1H), 6.69 (d, 1H), 3.85 (s, 3H).

$^{13}$C-NMR (100 MHz, MSM-d6): δ (ppm) 161, 158.7, 147.5, 145, 139.7, 134.5, 124, 116.3, 112.7, 110.2, 109.4, 104, 56.4.

Preparation R2ap: 7-(3,5-dimethoxyphenyl)-3H,4H,7H-pyrrolo[2,3-d]pyrimidin-4-one Using General Procedure 2 starting from Preparation R1a and 2-(3,5-dimethoxy)-phenyl-4,4,5,5-tetramethyl-(1,3,2)-dioxaborolane as reagents, Preparation R2ap was obtained. HRMS calculated for $C_{14}H_{13}N_3O_3$: 271.0957; found 272.1030 [(M+H)+ form].

$^1$H-NMR (500 MHz, MSM-d6): δ (ppm) 12.11 (s, 1H), 7.95 (d, 1H), 7.52 (d, 1H), 6.91 (d, 2H), 6.66 (d, 1H), 6.54 (t, 1H), 3.8 (s, 6H).

$^{13}$C-NMR (125 MHz, MSM-d6): δ (ppm) 144.5, 124.2, 103.5, 103.1, 98.9.

Preparation R2aq: 7-(3,4-dichlorophenyl)-3H,4H,7H-pyrrolo[2,3-d]pyrimidin-4-one

Using General Procedure 2 starting from Preparation R1b and 3,4-dichlorophenylboronic acid as reagents, Preparation R2aq was obtained. HRMS calculated for $C_{12}H_7Cl_2N_3O$: 278.9966; found 280.003 [(M+H)+ form].

$^1$H-NMR (500 MHz, MSM-d6): δ (ppm) 12.21 (brs, 1H), 8.15 (t, 1H), 8.02 (brs, 1H), 7.82 (d, 1H), 7.82 (d, 1H), 7.61 (d, 1H), 6.72 (d, 1H).

$^{13}$C-NMR (125 MHz, MSM-d6): δ (ppm) 145.1, 131.5, 125.9, 124.3, 123.8, 104.2.

Preparation R2ar: 7-(4-chloro-3-fluorophenyl)-3H,4H,7H-pyrrolo[2,3-d]pyrimidin-4-one Using General Procedure 3 starting from Preparation R1b and 4-chloro-3-fluoroiodobenzene as reagents, Preparation R2ar was obtained. HRMS calculated for $C_{12}H_7ClFN_3O$: 263.0262; found 264.0339 [(M+H)+ form].

$^1$H-NMR (500 MHz, MSM-d6): δ (ppm) 12.21 (s, 1H), 8.02 (d, 1H), 7.97 (dd, 1H), 7.77 (dd, 1H), 7.72 (dd, 1H), 7.6 (d, 1H), 6.72 (d, 1H).

$^{13}$C-NMR (125 MHz, MSM-d6): δ (ppm) 145.1, 131.5, 123.7, 121.5, 112.8, 104.2.

Preparation R2as: 7-(4-chloro-3-methoxyphenyl)-3H,4H,7H-pyrrolo[2,3-d]pyrimidin-4-one Using General Procedure 3 starting from Preparation R1b and 2-chloro-5-iodoanisole as reagents, Preparation R2as was obtained. HRMS calculated for $C_{13}H_{10}ClN_3O_2$: 275.0461; found 276.0537 [(M+H)+ form].

$^1$H-NMR (500 MHz, MSM-d6): δ (ppm) 12.15 (brs, 1H), 7.98 (brs, 1H), 7.58 (d, 1H), 7.57 (d, 1H), 7.49 (d, 1H), 7.36 (dd, 1H), 6.7 (d, 1H), 3.93 (s, 3H).

$^{13}$C-NMR (125 MHz, MSM-d6): δ (ppm) 158.7, 155.3, 147.4, 144.8, 137.7, 130.5, 124.2, 119.8, 117.3, 110, 109.4, 103.7, 56.9.

Preparation R2at: 7-(3,4-dimethoxyphenyl)-3H,4H,7H-pyrrolo[2,3-d]pyrimidin-4-one Using General Procedure 2 starting from Preparation R1b and 3,4-dimethoxyphenylboronic acid pinacol ester as reagents, Preparation R2at was obtained. HRMS calculated for $C_{14}H_{13}N_3O_3$: 271.0957; found 272.103 [(M+H)⁺ form].

¹H-NMR (500 MHz, MSM-d6): δ (ppm) 7.92 (d, 1H), 7.43 (d, 1H), 7.25 (d, 1H), 7.19 (dd, 1H), 7.08 (d, 1H), 6.65 (d, 1H), 3.8 (s, 6H).

¹³C-NMR (125 MHz, MSM-d6): δ (ppm) 144.5, 124.6, 116.9, 112.2, 109.3, 103.1, 56.3.

Preparation R2au: 4-{4-oxo-3H,4H,7H-pyrrolo[2,3-d]pyrimidin-7-yl}benzonitrile

Using General Procedure 3 starting from Preparation R1b and 4-iodobenzonitrile as reagents, Preparation R2au was obtained. HRMS calculated for $C_{13}H_8N_4O$: 236,0698; found 237.0775 [(M+H)⁺ form].

¹H-NMR (500 MHz, MSM-d6): δ (ppm) 12.25 (brs, 1H), 8.05 (m, 2H), 8.03 (m, 2H), 8.02 (brs, 1H), 7.66 (d, 1H), 6.75 (d, 1H).

¹³C-NMR (125 MHz, MSM-d6): δ (ppm) 147.6, 145.2, 141.5, 134, 124.6, 123.6, 119, 110.6, 109.4, 104.7.

Preparation R2av: 7-[4-(trifluoromethyl)phenyl]-3H,4H,7H-pyrrolo[2,3-d]pyrimidin-4-one Using General Procedure 3 starting from Preparation R1b and 4-iodobenzotrifluoride as reagents, Preparation R2av was obtained. HRMS calculated for $C_{13}H_8F_3N_3O$: 279, 0619; found 280.0691 [(M+H)⁺ form].

¹H-NMR (500 MHz, MSM-d6): δ (ppm) 12.23 (brs, 1H), 8.02 (m, 2H), 8.01 (d, 1H), 7.92 (m, 2H), 7.63 (d, 1H), 6.74 (d, 1H).

¹³C-NMR (125 MHz, MSM-d6): δ (ppm) 158.7, 147.6, 145.1, 126.9, 124.7, 123.8, 110.4, 104.5 ⁵N-NMR (50.6 MHz, MSM-d6): δ (ppm) 170.9.

Preparation R2aw: 7-[4-(difluoromethyl)phenyl]-3H,4H,7H-pyrrolo[2,3-d]pyrimidin-4-one Using General Procedure 3 starting from Preparation R1b and 1-(difluoromethyl)-4-iodobenzene as reagents, Preparation R2aw was obtained. HRMS calculated for $C_{13}H_9F_2N_3O$: 261.0714; found 262.0784 [(M+H)⁺ form].

¹H-NMR (500 MHz, MSM-d6): δ (ppm) 12.17 (brs, 1H), 7.99 (d, 1H), 7.91 (m, 2H), 7.75 (m, 2H), 7.58 (d, 1H), 7.12 (t, 1H), 6.72 (d, 1H).

¹³C-NMR (125 MHz, MSM-d6): δ (ppm) 144.9, 127.2, 124.7, 123.9, 115.1, 104.1.

Preparation R2ax: 7-[4-(hydroxymethyl)phenyl]-3H,4H,7H-pyrrolo[2,3-d]pyrimidin-4-one Using General Procedure 3 starting from Preparation R1b and 4-iodobenzyl alcohol as reagents, Preparation R2ax was obtained. HRMS calculated for $C_{13}H_{11}N_3O_2$: 241.0851; found 242.0925 [(M+H)⁺ form].

¹H-NMR (500 MHz, MSM-d6): δ (ppm) 12.07 (brs, 1H), 7.94 (s, 1H), 7.66 (m, 2H), 7.47 (m, 2H), 7.45 (d, 1H), 6.67 (d, 1H), 5.31 (t, 1H), 4.56 (d, 2H).

¹³C-NMR (125 MHz, MSM-d6): δ (ppm) 158.9, 147.4, 144.6, 142.2, 136.6, 127.6, 124.3, 124.2, 109.9, 103.5, 62.8.

Preparation R2ay: 7-(4-chlorophenyl)-3H,4H,7H-pyrrolo[2,3-d]pyrimidin-4-one

Using General Procedure 3 starting from Preparation R1b and 1-chloro-4-iodobenzene as reagents, Preparation R2ay was obtained. HRMS calculated for $C_{12}H_8ClN_3O$: 245.0356; found 246.0427 [(M+H)⁺ form].

¹H-NMR (500 MHz, MSM-d6): δ (ppm) 12.15 (brs, 1H), 7.97 (d, 1H), 7.78 (dm, 1H), 7.61 (dm, 1H), 7.53 (d, 1H), 6.7 (d, 1H).

¹³C-NMR (125 MHz, MSM-d6): δ (ppm) 158.7, 147.3, 144.8, 136.7, 131.7, 129.6, 126.1, 123.9, 109.9, 103.9.

Preparation R2az: 7-[4-(dimethylamino)phenyl]-3H,4H,7H-pyrrolo[2,3-d]pyrimidin-4-one Using General Procedure 2 starting from Preparation R1a and 4-(dimethylamino)phenylboronic acid as reagents, Preparation R2az was obtained.

HRMS calculated for $C_{14}H_{14}N_4O$: 254.1168; found 255.1243 [(M+H)⁺ form].

¹H-NMR (400 MHz, MSM-d6): δ (ppm) 11.98 (brs, 1H), 7.89 (d, 1H), 7.43 (m, 2H), 7.33 (d, 1H), 6.82 (m, 2H), 6.61 (d, 1H), 2.94 (s, 6H).

¹³C-NMR (100 MHz, MSM-d6): δ (ppm) 144.1, 125.6, 124.3, 112.7, 102.7, 40.6.

Preparation R2ba: 7-[4-(trifluoromethoxy)phenyl]-3H,4H,7H-pyrrolo[2,3-d]pyrimidin-4-one Using General Procedure 3 starting from Preparation R1b and 1-iodo-4-(trifluoromethoxy)benzene as reagents, Preparation R2ba was obtained. HRMS calculated for $C_{13}H_8F_3N_3O_2$: 295.0569; found 296.0648 [(M+H)⁺ form].

¹H-NMR (500 MHz, MSM-d6): δ (ppm) 12.15 (s, 1H), 7.97 (d, 1H), 7.86 (m, 2H), 7.56 (m, 2H), 7.54 (m, 1H), 6.71 (d, 1H).

¹³C-NMR (125 MHz, MSM-d6): δ (ppm) 144.8, 126.4, 124.1, 122.5, 103.9.

Preparation R2bb: 7-[4-(benzyloxy)phenyl]-3H,4H,7H-pyrrolo[2,3-d]pyrimidin-4-one Using General Procedure 3 starting from Preparation R1b and 4-benzyloxyiodobenzene as reagents, Preparation R2bb was obtained. HRMS calculated for $C_{19}H_{15}N_3O_2$: 317.1164; found 318.1243 [(M+H)⁺ form].

¹H-NMR (500 MHz, MSM-d6): δ (ppm) 12.05 (brs, 1H), 7.92 (d, 1H), 7.59 (dm, 2H), 7.48 (dm, 2H), 7.41 (d, 1H), 7.41 (tm, 2H), 7.35 (tm, 1H), 7.16 (dm, 2H), 6.65 (d, 1H), 5.18 (s, 2H).

¹³C-NMR (125 MHz, MSM-d6): δ (ppm) 158.8, 157.6, 147.3, 144.4, 137.4, 131, 129, 128.4, 128.2, 126.1, 124.3, 115.7, 109.4, 103.1, 69.9.

Preparation R2bc: 7-(5-methylthiophen-2-yl)-3H,4H,7H-pyrrolo[2,3-d]pyrimidin-4-one Using General Procedure 3 starting from Preparation R1b and 2-iodo-5-methylthiophene as reagents, Preparation R2bc was obtained. HRMS calculated for $C_{11}H_9N_3OS$: 231.0466; found 232.0541 [(M+H)⁺ form].

¹H-NMR (400 MHz, MSM-d6): δ (ppm) 12.17 (brs, 1H), 7.99 (d, 1H), 7.49 (d, 1H), 7.14 (d, 1H), 6.76 (dq, 1H), 6.67 (d, 1H), 2.46 (d, 3H).

¹³C-NMR (100 MHz, MSM-d6): δ (ppm) 145, 124.2, 123.9, 119.4, 103.9, 15.4.

Preparation R2bd: 7-(5-chlorothiophen-2-yl)-3H,4H,7H-pyrrolo[2,3-d]pyrimidin-4-one Using General Procedure 3 starting from Preparation R1b and 2-chloro-5-iodothiophene as reagents, Preparation R2bd was obtained. HRMS calculated for $C_{10}H_6N_3OSCl$: 250.9920; found 252.0005 ((M+H)$^+$ form].

1H-NMR (500 MHz, dmso-d6) δ ppm 12.28 (brs, 1H), 8.07 (d, 1H), 7.67 (d, 1H), 7.3 (d, 1H), 7.13 (d, 1H), 6.72 (d, 1H).

13C-NMR (500 MHz, dmso-d6) δ ppm 158.4, 146.8, 145.6, 136.4, 125.5, 124.6, 123.3, 117.5, 109.3, 104.6.

Preparation R2be: 7-(2,3-dihydro-1,4-benzodioxin-6-yl)-3H,4H,7H-pyrrolo[2,3-d]pyrimidin-4-one Using General Procedure 2 starting from Preparation R1a and 1,4-benzodioxane-6-boronic acid as reagents, Preparation R2be was obtained. HRMS calculated for $C_{14}H_{11}N_3O_3$: 269,0800; found 270.0881 [(M+H)$^+$ form].

$^1$H-NMR (500 MHz, MSM-d6): δ (ppm) 12.05 (brs, 1H), 7.92 (d, 1H), 7.4 (d, 1H), 7.22 (d, 1H), 7.13 (dd, 1H), 6.99 (d, 1H), 6.63 (d, 1H), 4.33-4.25 (m, 4H).

$^{13}$C-NMR (125 MHz, MSM-d6): δ (ppm) 144.4, 124.3, 117.7, 117.6, 113.8, 103.2.

Preparation R2bf: 7-(2H-1,3-benzodioxol-5-yl)-3H, 4H,7H-pyrrolo[2,3-d]pyrimidin-4-one Using General Procedure 2 starting from Preparation R1a and 3,4-methylenedioxyphenylboronic acid as reagents, Preparation R2bf was obtained. HRMS calculated for $C_{13}H_9N_3O_3$: 255,0644; found 256.0719 [(M+H)$^+$ form].

$^1$H-NMR (500 MHz, MSM-d6): δ (ppm) 12.05 (brs, 1H), 7.92 (d, 1H), 7.4 (d, 1H), 7.29 (d, 1H), 7.12 (dd, 1H), 7.05 (d, 1H), 6.63 (d, 1H), 6.11 (s, 2H).

$^{13}$C-NMR (125 MHz, MSM-d6): δ (ppm) 144.5, 124.5, 118.2, 108.7, 106.5, 103.1, 102.2.

Preparation R2bg: 7-(naphthalen-2-yl)-3H,4H,7H-pyrrolo[2,3-d]pyrimidin-4-one

Using General Procedure 2 starting from Preparation R1a and 2-naphthaleneboronic acid as reagents, Preparation R2bg was obtained. HRMS calculated for $C_{16}H_{11}N_3O$: 261,0902; found 262.0982 [(M+H)$^+$ form].

$^1$H-NMR (500 MHz, MSM-d6): δ (ppm) 12.14 (s, 1H), 8.25 (d, 1H), 8.09 (d, 1H), 8.01 (m, 1H), 8.01 (m, 1H), 8 (s, 1H), 7.91 (dd, 1H), 7.63 (d, 1H), 7.6 (tm, 1H), 7.57 (tm, 1H), 6.74 (d, 1H).

$^{13}$C-NMR (125 MHz, MSM-d6): δ (ppm) 158.8, 147.6, 144.8, 135.4, 133.4, 132, 129.4, 128.4, 128.2, 127.4, 126.9, 124.4, 123.5, 122.3, 109.9, 103.8.

Preparation R2bh: 7-[3-(trifluoromethyl)phenyl]-3H,4H,7H-pyrrolo[2,3-d]pyrimidin-4-one Using General Procedure 3 starting from Preparation R1b and 3-iodobenzotrifluoride as reagents, Preparation R2bh was obtained. HRMS calculated for $C_{13}H_8F_3N_3O$: 279.0620; found 280.0699 [(M+H)$^+$ form].

$^1$H-NMR (500 MHz, MSM-d6): δ (ppm) 12.19 (brs, 1H), 8.18 (brs, 1H), 8.07 (dm, 1H), 8.02 (d, 1H), 7.79 (t, 1H), 7.77 (dm, 1H), 7.65 (d, 1H), 6.73 (d, 1H).

$^{13}$C-NMR (125 MHz, MSM-d6): δ (ppm) 145.1, 131.1, 128.3, 124, 123.9, 121, 104.1.

Preparation R2bi: 7-{3-[(4-methylpiperazin-1-yl)methyl]phenyl}-3H,4H,7H-pyrrolo[2,3-d]pyrimidin-4-one Using General Procedure 2 starting from Preparation R1b and 3-(4-methyl-1-piperazinylmethyl)benzeneboronic acid pinacol ester as reagents, Preparation R2bi was obtained. HRMS calculated for $C_{18}H_{21}N_5O$: 323.1746; found 324.1828 [(M+H)$^+$ form].

$^1$H-NMR (500 MHz, MSM-d6): δ (ppm) 12.37/12.2/11.95 (brs, 3H), 8.04 (brs, 1H), 7.98 (s, 1H), 7.91 (dm, 1H), 7.67 (dm, 1H), 7.63 (d, 1H), 7.62 (t, 1H), 6.72 (d, 1H), 4.49 (brs, 2H), 3.8-3.3 (brm, 8H), 2.8 (brs, 3H).

$^{13}$C-NMR (125 MHz, MSM-d6): δ (ppm) 144.8, 130.3, 130, 127.3, 125.7, 124, 103.9, 58.7, 42.7.

Preparation R2bj: 7-[3-(hydroxymethyl)phenyl]-3H, 4H,7H-pyrrolo[2,3-d]pyrimidin-4-one Using General Procedure 3 starting from Preparation R1b and 3-iodobenzyl alcohol as reagents, Preparation R2bj was obtained. HRMS calculated for $C_{13}H_{11}N_3O_2$: 241.0851; found 242.0935 [(M+H)$^+$ form].

$^1$H-NMR (500 MHz, MSM-d6): δ (ppm) 12.11 (brs, 1H), 7.95 (d, 1H), 7.64 (brt, 1H), 7.55 (dm, 1H), 7.48 (t, 1H), 7.46 (d, 1H), 7.35 (dm, 1H), 6.68 (d, 1H), 4.58 (s, 2H).

$^{13}$C-NMR (125 MHz, MSM-d6): δ (ppm) 158.8, 147.4, 144.6, 144.4, 137.7, 129.4, 125.4, 124.2, 123, 122.5, 109.7, 103.5, 62.9.

Preparation R2bk: 7-(3-chlorophenyl)-3H,4H,7H-pyrrolo[2,3-d]pyrimidin-4-one

Using General Procedure 3 starting from Preparation R1b and 1-chloro-3-iodobenzene as reagents, Preparation R2bk was obtained. HRMS calculated for $C_{12}H_8ClN_3O$: 245.0356; found 246.0437 [(M+H)$^+$ form].

$^1$H-NMR (400 MHz, MSM-d6): δ (ppm) 12.17 (brs, 1H), 8 (d, 1H), 7.92 (m, 1H), 7.74 (dm, 1H), 7.58 (d, 1H), 7.57 (t, 1H), 7.47 (dm, 1H), 6.7 (d, 1H).

$^{13}$C-NMR (100 MHz, MSM-d6): δ (ppm) 145, 131.3, 127.2, 124.1, 123.9, 122.9, 104.

Preparation R2bl: 7-(3-fluorophenyl)-3H,4H,7H-pyrrolo[2,3-d]pyrimidin-4-one

Using General Procedure 3 starting from Preparation R1b and 1-fluoro-3-iodobenzene as reagents, Preparation R2bl was obtained. HRMS calculated for $C_{12}H_8N_3OF$: 229.0651; found 230.0729 [(M+H)$^+$ form].

$^1$H-NMR (400 MHz, MSM-d6): δ (ppm) 12.17 (brs, 1H), 7.99 (d, 1H), 7.72 (dm, 1H), 7.64 (m, 1H), 7.58 (d, 1H), 7.58 (m, 1H), 7.25 (m, 1H), 6.71 (d, 1H).

$^{13}$C-NMR (100 MHz, MSM-d6): δ (ppm) 144.9, 131.4, 130.9, 123.9, 120.2, 114, 111.6.

$^{19}$F-NMR (376.5 MHz, MSM-d6): δ (ppm) −111.7.

Preparation R2bm: 7-[3-(dimethylamino)phenyl]-3H,4H,7H-pyrrolo[2,3-d]pyrimidin-4-one Using General Procedure 2 starting from Preparation R1a and 3-(N,N-dimethylamino)phenylboronic acid as reagents, Preparation R2bm was obtained. HRMS calculated for $C_{14}H_{14}N_4O$: 254.1168; found 255.1229 [(M+H)$^+$ form].

$^1$H-NMR (500 MHz, MSM-d6): δ (ppm) 12.04 (brs, 1H), 7.92 (d, 1H), 7.45 (d, 1H), 7.3 (t, 1H), 6.94 (m, 1H), 6.93 (dm, 1H), 6.74 (dm, 1H), 6.65 (d, 1H), 2.95 (s, 6H).

$^{13}$C-NMR (125 MHz, MSM-d6): δ (ppm) 144.3, 129.9, 124.4, 112.4, 111.4, 108.6, 103.1, 40.5.

Preparation R2bn: 7-[3-(morpholin-4-yl)phenyl]-3H,4H,7H-pyrrolo[2,3-d]pyrimidin-4-one Using General Procedure 2 starting from Preparation R1a and 3-(morpholino)phenylboronic acid as reagents, Preparation R2bn was obtained. ¹H-NMR (400 MHz, MSM-d6): δ (ppm) 12.05 (brs, 1H), 7.93 (s, 1H), 7.47 (d, J=3.53 Hz, 1H), 7.36 (t, J=8.13 Hz, 1H), 7.19 (t, J=2.20 Hz, 1H), 7.11 (dd, J=1.27, 7.93 Hz, 1H), 6.98 (dd, J=1.96, 8.49 Hz, 1H), 6.65 (d, J=3.5 Hz, 1H), 3.75 (t, J=4.61 Hz, 4H), 3.18 (t, J=4.61 Hz, 4H).

Preparation R2bo: 7-[3-(trifluoromethoxy)phenyl]-3H,4H,7H-pyrrolo[2,3-d]pyrimidin-4-one Using General Procedure 3 starting from Preparation R1b and 3-(trifluoromethoxy)iodobenzene as reagents, Preparation R2bo was obtained. HRMS calculated for $C_{13}H_8F_3N_3O_2$: 295.0569; found 296.0651 [(M+H)⁺ form].
¹H-NMR (500 MHz, MSM-d6): δ (ppm) 12.91 (s, 1H), 8 (s, 1H), 7.87 (t, 1H), 7.82 (ddd, 1H), 7.68 (t, 1H), 7.6 (d, 1H), 7.41 (ddd, 1H), 6.71 (d, 1H).
¹³C-NMR (125 MHz, MSM-d6): δ (ppm) 145.1, 131.5, 123.9, 123.2, 119.5, 117.1, 104.1.

Preparation R2 bp: 7-(3-methoxyphenyl)-3H,4H,7H-pyrrolo[2,3-d]pyrimidin-4-one

Using General Procedure 3 starting from Preparation R1b and 3-iodoanisole as reagents, Preparation R2 bp was obtained. HRMS calculated for $C_{13}H_{11}N_3O_2$: 241.0851; found 242.0928 [(M+H)⁺ form].
¹H-NMR (400 MHz, MSM-d6): δ (ppm) 12.1 (brs, 1H), 7.95 (d, 1H), 7.51 (d, 1H), 7.44 (t, 1H), 7.31 (m, 1H), 7.3 (m, 1H), 6.98 (dm, 1H), 6.67 (d, 1H), 3.82 (s, 3H).
¹³C-NMR (100 MHz, MSM-d6): δ (ppm) 144.6, 130.4, 124.2, 116.7, 112.9, 110.5, 103.5.

Preparation R2bq: 7-[3-(benzyloxy)phenyl]-3H,4H,7H-pyrrolo[2,3-d]pyrimidin-4-one Using General Procedure 3 starting from Preparation R1b and 1-benzyloxy-3-iodobenzene as reagents, Preparation R2bq was obtained. HRMS calculated for $C_{19}H_{15}N_3O_2$: 317.1164; found 318.1235 [(M+H)⁺ form].
¹H-NMR (500 MHz, MSM-d6): δ (ppm) 12.1 (brs, 1H), 7.95 (d, 1H), 7.51 (d, 1H), 7.51-7.31 (m, 5H), 7.44 (t, 1H), 7.41 (m, 1H), 7.32 (dm, 1H), 7.05 (dm, 1H), 6.68 (d, 1H), 5.18 (s, 2H).
¹³C-NMR (125 MHz, MSM-d6): δ (ppm) 144.6, 130.5, 124.1, 116.8, 113.6, 111.4, 103.6, 70.

Preparation R2br: 7-(6-methylpyridin-2-yl)-3H,4H,7H-pyrrolo[2,3-d]pyrimidin-4-one Using General Procedure 3 starting from Preparation R1b and 2-iodo-6-methylpyridine as reagents, Preparation R2br was obtained. HRMS calculated for $C_{12}H_{10}N_4O$: 226.0855; found 227.0933 [(M+H)⁺ form].
¹H-NMR (500 MHz, MSM-d6): δ (ppm) 12 (brs, 1H), 8.25 (dm, 1H), 8.05 (s, 1H), 7.9 (t, 1H), 7.88 (d, 1H), 7.25 (dm, 1H), 6.68 (d, 1H), 2.52 (s, 3H).
¹³C-NMR (125 MHz, MSM-d6): δ (ppm) 144.9, 139.5, 122, 121.8, 113.8, 103.7, 24.4.

Preparation R2bs: 7-(6-methoxypyridin-2-yl)-3H,4H,7H-pyrrolo[2,3-d]pyrimidin-4-one The mixture of Preparation R1a (1.0 g, 6.51 mmol)), 2-iodo-6-methoxy-pyridine (2.35 g, 9.77 mmol, 1.5 eq.), copper(I)-iodide (125 mg, 0.65 mmol, 0.1 eq.), potassium-phosphate tribasic (2.76 g, 13 mmol, 2 eq.), (1R,2R)-(−)-1, 2-diaminocyclohexane (74 mg, 0.65 mmol, 0.1 eq.) in PDO (50 ml) was stirred under inert atmosphere for 4 hours at 100° C. The inorganics was filtered off and the filtrate was evaporated. The resulted residue was purified by flash chromatography (DCM).

The arylated product (920 mg, 3.5 mmol) and lithium-hydroxide monohydrate (1.48 g, 35 mmol) were stirred in the mixture of PDO (15 ml) and water (15 ml) at 110° C. for 24 hours. The residue was acidified by aq. HCl solution (1 N, 50 ml) and the resulted precipitate was filtered off and dried to give Preparation R2bs. HRMS calculated for $C_{12}H_{10}N_4O_2$: 242.0804; found 243.0884 [(M+H)⁺ form].
¹H-NMR (500 MHz, MSM-d6): δ (ppm) 12.21 (brs, 1H), 8.08 (dd, 1H), 8.03 (s, 1H), 7.94 (d, 1H), 7.9 (t, 1H), 6.78 (dd, 1H), 6.7 (d, 1H), 3.94 (s, 3H).
¹³C-NMR (125 MHz, MSM-d6): δ (ppm) 163.2, 158.5, 147.6, 147.4, 144.9, 141.9, 121.9, 111.2, 108.4, 108.4, 103.8, 53.9.

Preparation R2bt: 7-(naphthalen-1-yl)-3H,4H,7H-pyrrolo[2,3-d]pyrimidin-4-one

Using General Procedure 2 starting from Preparation R1a and 1-naphthaleneboronic acid as reagents, Preparation R2bt was obtained. HRMS calculated for $C_{16}H_{11}N_3O$: 261.0902; found 262.0984 [(M+H)⁺ form].
¹H-NMR (500 MHz, MSM-d6): δ (ppm) 12.04 (s, 1H), 8.12 (d, 1H), 8.09 (d, 1H), 7.78 (d, 1H), 7.67 (t, 1H), 7.61 (dm, 1H), 7.6 (t, 1H), 7.51 (tm, 1H), 7.39 (d, 1H), 7.21 (t, 1H), 6.77 (d, 1H).
¹³C-NMR (125 MHz, MSM-d6): δ (ppm) 158.9, 149.2, 144.6, 134.2, 134.1, 130.4, 129.5, 128.7, 127.8, 127.2, 126.4, 126.3, 126, 123, 108.7, 103.1.

Preparation R2bu: 7-(pyridin-3-yl)-3H,4H,7H-pyrrolo[2,3-d]pyrimidin-4-one

Using General Procedure 2 starting from Preparation R1a and pyridine-3-boronic acid as reagents, Preparation R2bu was obtained. HRMS calculated for $C_{11}H_8N_4O$: 212.0698; found 213.0774 [(M+H)⁺ form].
¹H-NMR (500 MHz, MSM-d6): δ (ppm) 12.29 (s, 1H), 8.55 (dd, 1H), 8.47 (dd, 1H), 8.06 (brs, 1H), 8.03 (t, 1H), 7.9 (d, 1H), 7.4 (t, 1H), 6.7 (d, 1H).
¹³C-NMR (125 MHz, MSM-d6): δ (ppm) 149.1, 145, 139.4, 122.5, 122, 116.9, 104.
¹⁵N-NMR (50.6 MHz, MSM-d6): δ (ppm) 171.2.

Preparation R2bv: 7-(pyridin-4-yl)-3H,4H,7H-pyrrolo[2,3-d]pyrimidin-4-one

Using General Procedure 2 starting from Preparation R1a and pyridine-4-boronic acid pinacol ester as reagents, Preparation R2bv was obtained. HRMS calculated for $C_{11}H_8N_4O$: 212.0698; found 213.0773 [(M+H)⁺ form].
¹H-NMR (500 MHz, MSM-d6): δ ppm 12.31 (brs, 1H), 8.69 (m, 2H), 8.05 (s, 1H), 7.99 (m, 2H), 7.73 (d, 1H), 6.76 (d, 1H).
¹³C-NMR (125 MHz, MSM-d6): δ (ppm) 151.3, 145.6, 122.8, 117.3, 105.

Preparation R2bw: 7-[1-(difluoromethyl)-1H-pyrazol-4-yl]-3H,4H,7H-pyrrolo[2,3-d]pyrimidin-4-one Using General Procedure 3 starting from Preparation R1b and 1-(difluoromethyl)-4-iodo-1H-pyrazole as reagents, Preparation R2bw was obtained. HRMS calculated for $C_{10}H_7F_2N_5O$: 251.0619; found 252.0682 [(M+H)$^+$ form].

$^1$H-NMR (500 MHz, MSM-d6): δ (ppm) 11.88 (brs, 1H), 8.83 (d, 1H), 8.4 (d, 1H), 8.03 (s, 1H), 7.91 (t, 1H), 7.58 (d, 1H), 6.69 (d, 1H).

$^{13}$C-NMR (125 MHz, MSM-d6): δ (ppm) 145.2, 136.2, 123.2, 121.3, 111, 104.

Preparation R2bx: 7-(1-methyl-1H-pyrazol-4-yl)-3H,4H,7H-pyrrolo[2,3-d]pyrimidin-4-one Using General Procedure 3 starting from Preparation R1b and 4-iodo-1-methyl-1H-pyrazole as reagents, Preparation R2bx was obtained. HRMS calculated for $C_{10}H_9N_5O$: 215.0807; found 216.0889 [(M+H)$^+$ form].

$^1$H-NMR (500 MHz, MSM-d6): δ (ppm) 12.12 (brs, 1H), 8.27 (s, 1H), 7.96 (s, 1H), 7.91 (d, 1H), 7.42 (d, 1H), 6.63 (d, 1H), 3.89 (s, 3H).

$^{13}$C-NMR (125 MHz, MSM-d6): δ (ppm) 158.6, 146.9, 144.7, 132.1, 124.3, 123.4, 121.4, 109, 103.4, 38.5.

Preparation R2by: 7-(propan-2-yl)-3H,4H,7H-pyrrolo[2,3-d]pyrimidin-4-one

Using General Procedure 1 starting from Preparation R1a and 2-iodopropane as reagents, Preparation R2by was obtained. HRMS calculated for $C_9H_{11}N_3O$: 177.0902; found 178.0979 [(M+H)$^+$ form].

$^1$H-NMR (500 MHz, MSM-d6): δ (ppm) 11.83 (brs, 1H), 7.87 (s, 1H), 7.24 (d, 1H), 6.47 (d, 1H), 4.85 (sept., 1H), 1.42 (d, 6H).

$^{13}$C-NMR (125 MHz, MSM-d6): δ (ppm) 158.8, 146.8, 143.5, 120.7, 108.2, 102, 46.5, 23.

$^{15}$N-NMR (50.6 MHz, MSM-d6): δ (ppm) 168.

Preparation R2ca: 7-cyclobutyl-3H,4H,7H-pyrrolo[2,3-d]pyrimidin-4-one

Using General Procedure 1 starting from Preparation R1a and cyclobutyl bromide as reagents, Preparation R2ca was obtained. HRMS calculated for $C_{10}H_{11}N_3O$: 189.0902; found 190.0974 [(M+H)$^+$ form].

$^1$H-NMR (500 MHz, MSM-d6): δ (ppm) 11.85 (brs, 1H), 7.88 (brs, 1H), 7.09 (d, 1H), 6.44 (d, 1H), 3.70 (m, 1H).

$^{13}$C-NMR (125 MHz, MSM-d6): δ (ppm) 158.7, 147.7, 143.8, 125.1, 108.1, 101.7, 31.8.

Preparation R2cb: 7-(1-methylpiperidin-4-yl)-3H,4H,7H-pyrrolo[2,3-d]pyrimidin-4-one Using General Procedure 4 starting from Preparation R1a and 4-hydroxy-1-methylpiperidine as reagents, Preparation R2cb was obtained. HRMS calculated for $C_{12}H_{16}N_4O$: 232.1324; found 233.1405 [(M+H)$^+$ form].

$^1$H-NMR (500 MHz, MSM-d6): δ (ppm) 11.82 (brs, 1H), 7.86 (d, 1H), 7.29 (d, 1H), 6.46 (d, 1H), 4.44 (m, 1H), 2.89/2.05 (m, 4H), 2.22 (s, 3H), 2.02/1.82 (m, 4H).

$^{13}$C-NMR (125 MHz, MSM-d6): δ (ppm) 143.9, 121.2, 102.1, 55.1, 52.1, 46.1, 32.3.

Preparation R2cc: 7-(2,2-difluoroethyl)-3H,4H,7H-pyrrolo[2,3-d]pyrimidin-4-one

Using General Procedure 1 starting from Preparation R1a and 2-iodo-1,1-difluoroethane as reagents, Preparation R2cc was obtained. HRMS calculated for $C_8H_7N_3OF_2$: 199.0557; found 200.0634 ((M+H)$^+$ form].

$^1$H-NMR (400 MHz, DMSO-d6) δ ppm 11.99 (brs, 1H), 7.93 (s, 1H), 7.16 (d, 1H), 6.53 (d, 1H), 6.37 (tt, 1H), 4.6 (td, 2H).

$^{13}$C-NMR (400 MHz, DMSO-d6) δ ppm 144.4, 124.8, 114.3, 102.5, 46.2.

Preparation R2cd: 7-(2-fluoroethyl)-3H,4H,7H-pyrrolo[2,3-d]pyrimidin-4-one

Using General Procedure 1 starting from Preparation R1a and 1-fluoro-2-iodoethane as reagents, Preparation R2cd was obtained. HRMS calculated for $C_8H_8NOF$: 181.0651; found 182.0728 ((M+H)$^+$ form].

$^1$H-NMR (400 MHz, dmso-d6) δ ppm 11.91 (brs, 1H), 7.9 (s, 1H), 7.17 (d, 1H), 6.49 (d, 1H), 4.74 (dt, 2H), 4.43 (dt, 2H).

$^{13}$C-NMR (400 MHz, dmso-d6) δ ppm 144, 124.3, 102, 83.1, 45.1.

Preparation R2ce: 7-(2-hydroxyethyl)-3H,4H,7H-pyrrolo[2,3-d]pyrimidin-4-one

Using General Procedure 1 starting from Preparation R1a and 2-chloroethanol as reagents, Preparation R2ce was obtained. $^1$H-NMR (400 MHz, MSM-d6): δ (ppm) 11.83 (brs, 1H), 7.86 (d, J=2.4 Hz, 1H), 7.12 (d, J=3.92 Hz, 1H), 6.43 (d, J=3.14 Hz, 1H), 4.92 (t, J=5.49 Hz, 1H), 4.15 (t, J=6.28 Hz, 2H), 3.68 (q, J=5.49 Hz, 2H).

Preparation R2cg: 7-[(4-chlorophenyl)methyl]-3H,4H,7H-pyrrolo[2,3-d]pyrimidin-4-one Using General Procedure 1 starting from Preparation R1a and 4-chlorobenzyl bromide as reagents, Preparation R2cg was obtained. HRMS calculated for $C_{13}H_{10}ClN_3O$: 259.0512; found 260.0583 [(M+H)$^+$ form].

$^1$H-NMR (400 MHz, MSM-d6): δ (ppm) 11.93 (s, 7.9 (s, 1H), 7.39 (m, 2H), 7.23 (m, 2H), 7.22 (d, 1H), 6.51 (d, 1H), 5.34 (s, 2H).

$^{13}$C-NMR (100 MHz, MSM-d6): δ (ppm) 158.7, 147.4, 144.2, 137.5, 132.5, 129.5, 129, 124.2, 108.3, 102.4, 47.5.

Preparation R2ch: 7-[(3-chlorophenyl)methyl]-3H,4H,7H-pyrrolo[2,3-d]pyrimidin-4-one Using General Procedure 1 starting from Preparation R1a and 3-chlorobenzyl bromide as reagents, Preparation R2ch was obtained. HRMS calculated for $C_{13}H_{10}ClN_3O$: 259.0512; found 260.0580 [(M+H)$^+$ form].

$^1$H-NMR (500 MHz, MSM-d6): δ (ppm) 11.94 (brs, 1H), 7.92 (d, 1H), 7.35 (m, 1H), 7.35 (m, 1H), 7.28 (t, 1H), 7.25 (d, 1H), 7.16 (dm, 1H), 6.51 (d, 1H), 5.35 (s, 2H).

$^{13}$C-NMR (125 MHz, MSM-d6): δ (ppm) 158.7, 147.6, 144.3, 140.9, 133.6, 131.1, 128, 127.5, 126.4, 124.3, 108.4, 102.4, 47.5.

Preparation R2ci: 7-[(2-chlorophenyl)methyl]-3H,4H,7H-pyrrolo[2,3-d]pyrimidin-4-one Using General Procedure 1 starting from Preparation R1a and 2-chlorobenzyl bromide as reagents, Preparation R2ci was obtained. HRMS calculated for $C_{13}H_{10}ClN_3O$: 259.0512; found 260.0587 [(M+H)$^+$ form].

$^1$H-NMR (400 MHz, MSM-d6): δ (ppm) 11.95 (brs, 1H), 7.89 (d, 1H), 7.5 (dm, 1H), 7.32 (m, 1H), 7.26 (m, 1H), 7.17 (d, 1H), 6.72 (dm, 1H), 6.55 (d, 1H), 5.44 (s, 2H).

$^{13}$C-NMR (100 MHz, MSM-d6): δ (ppm) 144.3, 129.8, 129.8, 128.8, 128.1, 124.5, 102.5, 46.

EXAMPLES

The following Examples illustrate the invention but do not limit it in any way.

tert-butyl (3R,4R)-4-[4-hydroxy-4-[(7-methyl-4-oxo-pyrrolo[2,3-d]pyrimidin-3-yl)methyl]piperidine-1-carbonyl]-3-phenyl-piperidine-1-carboxylate (EXAMPLE 1)

Using General Procedure 5 starting from Preparation R2g and Preparation R1c as reagents, EXAMPLE 1 was obtained. HRMS calculated for $C_{30}H_{39}N_5O_5$: 549.2951; found 550.3021 [(M+H) form].

tert-butyl (3R,4R)-4-[4-hydroxy-4-[(4-oxothieno[2,3-d]pyrimidin-3-yl)methyl]piperidine-1-carbonyl]-3-phenyl-piperidine-1-carboxylate (EXAMPLE 2)

Using General Procedure 5 starting from 3H-thieno[2,3-d]pyrimidin-4-one and Preparation R1c as reagents, EXAMPLE 2 was obtained. HRMS calculated for $C_{29}H_{36}N_4O_5S$: 552.2406; found 553.2479 [(M+H) form].

tert-butyl (3R,4R)-4-[4-[(7-ethyl-4-oxo-pyrrolo[2,3-d]pyrimidin-3-yl)methyl]-4-hydroxy-piperidine-1-carbonyl]-3-phenyl-piperidine-1-carboxylate (EXAMPLE 3)

Using General Procedure 5 starting from Preparation R2h and Preparation R1c as reagents, EXAMPLE 3 was obtained. HRMS calculated for $C_{31}H_{41}N_5O_5$: 563.3108; found 564.319 [(M+H) form].

tert-butyl (3R,4R)-4-[4-hydroxy-4-[(4-oxo-7-prop-2-ynyl-pyrrolo[2,3-d]pyrimidin-3-yl)methyl]piperidine-1-carbonyl]-3-phenyl-piperidine-1-carboxylate (EXAMPLE 4)

Using General Procedure 5 starting from Preparation R2i and Preparation R1c as reagents, EXAMPLE 4 was obtained. HRMS calculated for $C_{32}H_{39}N_5O_5$: 573.2951; found 574.3024 [(M+H) form].

tert-butyl (3R,4R)-4-[4-[(7-cyclopropyl-4-oxo-pyrrolo[2,3-d]pyrimidin-3-yl)methyl]-4-hydroxy-piperidine-1-carbonyl]-3-phenyl-piperidine-1-carboxylate (EXAMPLE 5)

Using General Procedure 5 starting from Preparation R2j and Preparation R1c as reagents, EXAMPLE 5 was obtained. HRMS calculated for $C_{32}H_{41}N_5O_5$: 575.3108; found 576.3189 [(M+H) form].

tert-butyl (3R,4R)-4-[4-[(7-chloro-4-oxo-thieno[3,4-d]pyrimidin-3-yl)methyl]-4-hydroxy-piperidine-1-carbonyl]-3-phenyl-piperidine-1-carboxylate (EXAMPLE 6)

Using General Procedure 5 starting from 7-chloro-3H-thieno[3,4-d]pyrimidin-4-one and Preparation R1c as reagents, EXAMPLE 6 was obtained. HRMS calculated for $C_{29}H_{35}ClN_4O_5S$: 586.2017; found 609.1912 [(M+Na) form].

tert-butyl (3R,4R)-4-[4-[(7-buta-2,3-dienyl-4-oxo-pyrrolo[2,3-d]pyrimidin-3-yl)methyl]-4-hydroxy-piperidine-1-carbonyl]-3-phenyl-piperidine-1-carboxylate (EXAMPLE 7)

Using General Procedure 5 starting from Preparation R2k and Preparation R1c as reagents, EXAMPLE 7 was obtained. HRMS calculated for $C_{33}H_{41}N_5O_5$: 587.3108; found 588.318 [(M+H) form].

tert-butyl (3R,4R)-4-[4-[[7-(cyclopropylmethyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 8)

Using General Procedure 5 starting from Preparation R2l and Preparation R1c as reagents, EXAMPLE 8 was obtained. HRMS calculated for $C_{33}H_{43}N_5O_5$: 589.3264; found 590.3342 [(M+H) form].

tert-butyl (3R,4R)-4-[4-hydroxy-4-[(7-isobutyl-4-oxo-pyrrolo[2,3-d]pyrimidin-3-yl)methyl]piperidine-1-carbonyl]-3-phenyl-piperidine-1-carboxylate (EXAMPLE 9)

Using General Procedure 5 starting from Preparation R2m and Preparation R1c as reagents, EXAMPLE 9 was obtained. HRMS calculated for $C_{33}H_{45}N_5O_5$: 591.342; found 592.3501 [(M+H) form].

tert-butyl (3R,4R)-4-[4-hydroxy-4-[(9-methyl-4-oxo-pyrimido[4,5-b]indol-3-yl)methyl]piperidine-1-carbonyl]-3-phenyl-piperidine-1-carboxylate (EXAMPLE 10)

Using General Procedure 5 starting from Preparation R2n and Preparation R1c as reagents, EXAMPLE 10 was obtained. HRMS calculated for $C_{34}H_{41}N_5O_5$: 599.3108; found 600.3181 [(M+H) form].

tert-butyl (3R,4R)-4-[4-[[7-(cyclobutylmethyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 11)

Using General Procedure 5 starting from Preparation R2o and Preparation R1c as reagents, EXAMPLE 11 was obtained. HRMS calculated for $C_{34}H_{45}N_5O_5$: 603.342; found 604.3502 [(M+H) form].

tert-butyl (3R,4R)-4-[4-[[7-(2-dimethylaminoethyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 12)

Using General Procedure 5 starting from Preparation R2p and Preparation R1c as reagents, EXAMPLE 12 was obtained. HRMS calculated for $C_{33}H_{46}N_6O_5$: 606.353; found 607.36 [(M+H) form].

tert-butyl (3R,4R)-4-[4-hydroxy-4-[(4-oxo-7-phenyl-pyrrolo[2,3-d]pyrimidin-3-yl)methyl]piperidine-1-carbonyl]-3-phenyl-piperidine-1-carboxylate (EXAMPLE 13)

Using General Procedure 5 starting from Preparation R2q and Preparation R1c as reagents, EXAMPLE 13 was obtained. HRMS calculated for $C_{35}H_{41}N_5O_5$: 611.3108; found 612.3192 [(M+H) form].

tert-butyl (3R,4R)-4-[4-hydroxy-4-[(4-oxo-7-phenyl-5H-pyrrolo[3,2-d]pyrimidin-3-yl)methyl]piperidine-1-carbonyl]-3-phenyl-piperidine-1-carboxylate (EXAMPLE 14)

Using General Procedure 5 starting from 7-phenyl-3,5-dihydropyrrolo[3,2-d]pyrimidin-4-one and Preparation R1c as reagents, EXAMPLE 14 was obtained. HRMS calculated for $C_{35}H_{41}N_5O_5$: 611.3108; found 612.3182 [(M+H) form].

tert-butyl (3R,4R)-4-[4-hydroxy-4-[[4-oxo-7-(2-pyridyl)pyrrolo[2,3-d]pyrimidin-3-yl]methyl]piperidine-1-carbonyl]-3-phenyl-piperidine-1-carboxylate (EXAMPLE 15)

Using General Procedure 5 starting from Preparation R2b and Preparation R1c as reagents, EXAMPLE 15 was obtained. HRMS calculated for $C_{34}H_{40}N_6O_5$: 612.306; found 613.3132 [(M+H) form].

tert-butyl (3R,4R)-4-[4-hydroxy-4-[(4-oxo-1-phenyl-pyrazolo[3,4-d]pyrimidin-5-yl)methyl]piperidine-1-carbonyl]-3-phenyl-piperidine-1-carboxylate (EXAMPLE 16)

Using General Procedure 5 starting from 1-phenyl-5H-pyrazolo[3,4-d]pyrimidin-4-one and Preparation R1c as reagents, EXAMPLE 16 was obtained. HRMS calculated for $C_{34}H_{40}N_6O_5$: 612.306; found 613.312 [(M+H) form].

tert-butyl (3R,4R)-4-[4-hydroxy-4-[(6-oxo-9-phenyl-purin-1-yl)methyl]piperidine-1-carbonyl]-3-phenyl-piperidine-1-carboxylate (EXAMPLE 17)

Using General Procedure 5 starting from 9-phenyl-1H-purin-6-one and Preparation R1c as reagents, EXAMPLE 17 was obtained. HRMS calculated for $C_{34}H_{40}N_6O_5$: 612.306; found 613.3142 [(M+H) form].

tert-butyl (3R,4R)-4-[4-[(7-bromo-4-oxo-pyrrolo[2,1-f][1,2,4]triazin-3-yl)methyl]-4-hydroxy-piperidine-1-carbonyl]-3-phenyl-piperidine-1-carboxylate (EXAMPLE 18)

Using General Procedure 5 starting from 7-bromo-3H-pyrrolo[2,1-f][1,2,4]triazin-4-one and Preparation R1c as reagents, EXAMPLE 18 was obtained. HRMS calculated for $C_{29}H_{36}BrN_5O_5$: 613.19; found 612.1851 [(M−H) form].

tert-butyl (3R,4R)-4-[4-hydroxy-4-[(7-oxo-3-phenyl-isoxazolo[4,5-d]pyrimidin-6-yl)methyl]piperidine-1-carbonyl]-3-phenyl-piperidine-1-carboxylate (EXAMPLE 19)

Using General Procedure 5 starting from 3-phenyl-6H-isoxazolo[4,5-d]pyrimidin-7-one and Preparation R1c as reagents, EXAMPLE 19 was obtained. HRMS calculated for $C_{34}H_{39}N_5O_6$: 613.29; found 636.2782 [(M+Na) form].

tert-butyl (3R,4R)-4-[4-hydroxy-4-[(4-oxo-7-pyrimidin-2-yl-pyrrolo[2,3-d]pyrimidin-3-yl)methyl]piperidine-1-carbonyl]-3-phenyl-piperidine-1-carboxylate (EXAMPLE 20)

Using General Procedure 5 starting from Preparation R2s and Preparation R1c as reagents, EXAMPLE 20 was obtained. HRMS calculated for $C_{33}H_{39}N_7O_5$: 613.3013; found 614.3102 [(M+H) form].

tert-butyl (3R,4R)-4-[4-hydroxy-4-[(7-oxo-3-phenyl-triazolo[4,5-d]pyrimidin-6-yl)methyl]piperidine-1-carbonyl]-3-phenyl-piperidine-1-carboxylate (EXAMPLE 21)

Using General Procedure 5 starting from 3-phenyl-6H-triazolo[4,5-d]pyrimidin-7-one and Preparation R1c as reagents, EXAMPLE 21 was obtained. HRMS calculated for $C_{33}H_{39}N_7O_5$: 613.3013; found 614.3095 [(M+H) form].

tert-butyl (3R,4R)-4-({4-[(6,8-dimethyl-4-oxopyrimido[5,4-b]indolizin-3(4H)-yl)methyl]-4-hydroxypiperidin-1-yl}carbonyl)-3-phenylpiperidine-1-carboxylate (EXAMPLE 22)

Using General Procedure 5 starting from Preparation R2t and Preparation R1c as reagents, EXAMPLE 22 was obtained. HRMS calculated for $C_{34}H_{42}N_6O_5$: 614.3217; found 615.3301 [(M+H) form].

tert-butyl (3R,4R)-4-[4-hydroxy-4-[[7-(1-methylimidazol-4-yl)-4-oxo-pyrrolo[2,3-d]pyrimidin-3-yl]methyl]piperidine-1-carbonyl]-3-phenyl-piperidine-1-carboxylate (EXAMPLE 23)

Using General Procedure 5 starting from Preparation R2u and Preparation R1c as reagents, EXAMPLE 23 was obtained. HRMS calculated for $C_{33}H_{41}N_7O_5$: 615.3169; found 616.324 [(M+H) form].

tert-butyl (3R,4R)-4-[4-hydroxy-4-[[4-oxo-7-(3-thienyl)pyrrolo[2,3-d]pyrimidin-3-yl]methyl]piperidine-1-carbonyl]-3-phenyl-piperidine-1-carboxylate (EXAMPLE 24)

Using General Procedure 5 starting from Preparation R2v and Preparation R1c as reagents, EXAMPLE 24 was obtained. HRMS calculated for $C_{33}H_{39}N_5O_5S$: 617.2672; found 618.2736 [(M+H) form].

tert-butyl (3R,4R)-4-[4-hydroxy-4-[[4-oxo-7-(2-thienyl)pyrrolo[2,3-d]pyrimidin-3-yl]methyl]piperidine-1-carbonyl]-3-phenyl-piperidine-1-carboxylate (EXAMPLE 25)

Using General Procedure 5 starting from Preparation R2w and Preparation R1c as reagents, EXAMPLE 25 was obtained. HRMS calculated for $C_{33}H_{39}N_5O_5S$: 617.2672; found 618.2744 [(M+H) form].

tert-butyl (3R,4R)-4-[4-hydroxy-4-[[4-oxo-7-(2,2,2-trifluoroethyl)pyrrolo[2,3-d]pyrimidin-3-yl]methyl]piperidine-1-carbonyl]-3-phenyl-piperidine-1-carboxylate (EXAMPLE 26)

Using General Procedure 5 starting from Preparation R2x and Preparation R1c as reagents, EXAMPLE 26 was obtained. HRMS calculated for $C_{31}H_{38}F3N_5O_5$: 617.2825; found 618.2912 [(M+H) form].

tert-butyl (3R,4R)-4-[4-hydroxy-4-[(4-oxo-7-thiazol-2-yl-pyrrolo[2,3-d]pyrimidin-3-yl)methyl]piperidine-1-carbonyl]-3-phenyl-piperidine-1-carboxylate (EXAMPLE 27)

Using General Procedure 5 starting from Preparation R2y and Preparation R1c as reagents, EXAMPLE 27 was obtained. HRMS calculated for $C_{32}H_{38}N_6O_5S$: 618.2625; found 641.251 [(M+Na) form].

tert-butyl (3R,4R)-4-[4-[[7-[3-(dimethylamino)propyl]-4-oxo-pyrrolo[2,3-d]pyrimidin-3-yl]methyl]-4-hydroxy-piperidine-1-carbonyl]-3-phenyl-piperidine-1-carboxylate (EXAMPLE 28)

Using General Procedure 5 starting from Preparation R2z and Preparation R1c as reagents, EXAMPLE 28 was obtained. HRMS calculated for $C_{34}H_{48}N_6O_5$: 620.3686; found 621.3731 [(M+H) form].

tert-butyl (3R,4R)-4-[4-hydroxy-4-[[7-(m-tolyl)-4-oxo-pyrrolo[2,3-d]pyrimidin-3-yl]methyl]piperidine-1-carbonyl]-3-phenyl-piperidine-1-carboxylate (EXAMPLE 29)

Using General Procedure 5 starting from Preparation R2aa and Preparation R1c as reagents, EXAMPLE 29 was obtained. HRMS calculated for $C_{36}H_{43}N_5O_5$: 625.3264; found 626.3357 [(M+H) form].

tert-butyl (3R,4R)-4-[4-hydroxy-4-[[4-oxo-7-(p-tolyl)pyrrolo[2,3-d]pyrimidin-3-yl]methyl]piperidine-1-carbonyl]-3-phenyl-piperidine-1-carboxylate (EXAMPLE 30)

Using General Procedure 5 starting from Preparation R2ab and Preparation R1c as reagents, EXAMPLE 30 was obtained. HRMS calculated for $C_{36}H_{43}N_5O_5$: 625.3264; found 626.3358 [(M+H) form].

tert-butyl (3R,4R)-4-[4-[(7-benzyl-4-oxo-pyrrolo[2,3-d]pyrimidin-3-yl)methyl]-4-hydroxy-piperidine-1-carbonyl]-3-phenyl-piperidine-1-carboxylate (EXAMPLE 31)

Using General Procedure 5 starting from Preparation R2ac and Preparation R1c as reagents, EXAMPLE 31 was obtained. HRMS calculated for $C_{36}H_{43}N_5O_5$: 625.3264; found 626.3343 [(M+H) form].

tert-butyl (3R,4R)-4-[4-hydroxy-4-[(6-methyl-4-oxo-7-phenyl-pyrrolo[2,3-d]pyrimidin-3-yl)methyl]piperidine-1-carbonyl]-3-phenyl-piperidine-1-carboxylate (EXAMPLE 32)

Using General Procedure 5 starting from Preparation R2ad and Preparation R1c as reagents, EXAMPLE 32 was obtained. HRMS calculated for $C_{36}H_{43}N_5O_5$: 625.3264; found 626.3335 [(M+H) form].

tert-butyl (3R,4R)-4-[4-hydroxy-4-[(7-oxo-3-phenyl-isothiazolo[4,5-d]pyrimidin-6-yl)methyl]piperidine-1-carbonyl]-3-phenyl-piperidine-1-carboxylate (EXAMPLE 33)

Using General Procedure 5 starting from 3-phenyl-6H-isothiazolo[4,5-d]pyrimidin-7-one and Preparation R1c as reagents, EXAMPLE 33 was obtained. HRMS calculated for $C_{34}H_{39}N_5O_5S$: 629.2672; found 652.2559 [(M+Na) form].

tert-butyl (3R,4R)-4-[4-[[7-(4-fluorophenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 34)

Using General Procedure 5 starting from Preparation R2ae and Preparation R1c as reagents, EXAMPLE 34 was obtained. HRMS calculated for $C_{35}H_{40}FN_5O_5$: 629.3013; found 530.2568 [(M+H-Boc) form].

tert-butyl (3R,4R)-4-[4-[[7-(3-fluorophenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 35)

Using General Procedure 5 starting from Preparation R2bl and Preparation R1c as reagents, EXAMPLE 35 was obtained. HRMS calculated for $C_{35}H_{40}FN_5O_5$: 629.3013; found 652.2909 [(M+Na) form].

tert-butyl (3R,4R)-4-[4-[(7-bromo-4-oxo-thieno[3,2-d]pyrimidin-3-yl)methyl]-4-hydroxy-piperidine-1-carbonyl]-3-phenyl-piperidine-1-carboxylate (EXAMPLE 36)

Using General Procedure 5 starting from 7-bromo-3H-thieno[3,2-d]pyrimidin-4-one and Preparation R1c as reagents, EXAMPLE 36 was obtained. HRMS calculated for $C_{29}H_{35}BrN_4O_5S$: 630.1511; found 653.1419 [(M+Na) form].

tert-butyl (3R,4R)-4-[4-hydroxy-4-[[7-(5-methyl-2-thienyl)-4-oxo-pyrrolo[2,3-d]pyrimidin-3-yl]methyl]piperidine-1-carbonyl]-3-phenyl-piperidine-1-carboxylate (EXAMPLE 37)

Using General Procedure 5 starting from Preparation R2bc and Preparation R1c as reagents, EXAMPLE 37 was obtained. HRMS calculated for $C_{34}H_{41}N_5O_5S$: 631.2828; found 654.2719 [(M+Na) form].

tert-butyl (3R,4R)-4-[4-hydroxy-4-[[7-(1-methyl-4-piperidyl)-4-oxo-pyrrolo[2,3-d]pyrimidin-3-yl]methyl]piperidine-1-carbonyl]-3-phenyl-piperidine-1-carboxylate (EXAMPLE 38)

Using General Procedure 5 starting from Preparation R2cb and Preparation R1c as reagents, EXAMPLE 38 was obtained. HRMS calculated for $C_{35}H_{48}N_6O_5$: 632.3686; found 633.3766 [(M+H) form].

tert-butyl (3R,4R)-4-[4-[[7-(4-cyanophenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 39)

Using General Procedure 5 starting from Preparation R2au and Preparation R1c as reagents, EXAMPLE 39 was obtained. HRMS calculated for $C_{36}H_{40}N_6O_5$: 636.306; found 637.3127 [(M+H) form].

tert-butyl (3R,4R)-4-[4-hydroxy-4-[[7-(4-methoxyphenyl)-4-oxo-pyrrolo[2,3-d]pyrimidin-3-yl]methyl]piperidine-1-carbonyl]-3-phenyl-piperidine-1-carboxylate (EXAMPLE 40)

Using General Procedure 5 starting from Preparation R2c and Preparation R1c as reagents, EXAMPLE 40 was obtained. HRMS calculated for $C_{36}H_{43}N_5O_6$: 641.3214; found 642.3297 [(M+H) form].

tert-butyl (3R,4R)-4-[4-hydroxy-4-[[7-(3-methoxy-phenyl)-4-oxo-pyrrolo[2,3-d]pyrimidin-3-yl]methyl]piperidine-1-carbonyl]-3-phenyl-piperidine-1-carboxylate (EXAMPLE 41)

Using General Procedure 5 starting from Preparation R2bp and Preparation R1c as reagents, EXAMPLE 41 was obtained. HRMS calculated for $C_{36}H_{43}N_5O_6$: 641.3214; found 642.3313 [(M+H) form].

tert-butyl (3R,4R)-4-[4-hydroxy-4-[[7-[4-(hydroxymethyl)phenyl]-4-oxo-pyrrolo[2,3-d]pyrimidin-3-yl]methyl]piperidine-1-carbonyl]-3-phenyl-piperidine-1-carboxylate (EXAMPLE 42)

Using General Procedure 5 starting from Preparation R2ax and Preparation R1c as reagents, EXAMPLE 42 was obtained. HRMS calculated for $C_{36}H_{43}N_5O_6$: 641.3214; found 642.3288 [(M+H) form].

tert-butyl (3R,4R)-4-[4-hydroxy-4-[[6-(hydroxymethyl)-4-oxo-7-phenyl-pyrrolo[2,3-d]pyrimidin-3-yl]methyl]piperidine-1-carbonyl]-3-phenyl-piperidine-1-carboxylate (EXAMPLE 43)

Preparation R1b (10 g, 67.05 mmol, 1 eq.), iodobenzene (87.2 mmol, 1.3 eq.), CuI (1.28 g, 190.45, 6,705 mmol, 0.1 eq.), DMEDA (1.45 ml, 13.4 mmol, 1.18 g, 0.2 eq.), anhydrous $K_2CO_3$ (12.05 g, 87.16 mmol, 1.3 eq.) was suspended in dry acetonitrile (50 ml), flushed with $N_2$ and stirred at 80° C. for 1.5 h. After the reaction completed, the mixture was diluted with water (200 ml) and cooled to r.t. The mixture was filtered, and washed with water (3×30 ml), aq. $NH_3$ solution (40 ml, 25%), water (3×50 ml), heptane (50 then 30 ml) and dried in vacuum.

A flame dried 3-necked round flask was charged with 5 ml dry THF under $N_2$ atmosphere. 420 µl (1.5 eq.) $iPr_2NH$ was added via a syringe and the round flask was cooled to −78° C. 1.25 ml (1.5 eq.) n-BuLi was added via a syringe and stirred for 30 minutes. Then 4-methoxy-7-phenyl-pyrrolo[2,3-d]pyrimidine obtained in previous step (450 mg, 2 mmol, 1 eq.) dissolved in 20 ml dry THF was added dropwise and stirred for 1 hour. Then methyl formate (360 mg, 3 eq.) was added dissolved in 10 ml dry THF. After the reaction was completed 40 ml sat. $NH_4Cl$ was added and extracted with 3×40 ml EEO, dried, filtered and evaporated. Flash chromatography with Hexane:EEO gave (4-methoxy-7-phenyl-pyrrolo[2,3-d]pyrimidin-6-yl)methanol.

A part of the crude product (127 mg, 0.5 mmol) was dissolved in 2.5 ml PDO and cc. HCl (82 µL, 1 mmol, 2 eq.) was added. The solution was heated, stirred at 100° C. for 2 hours, and it was evaporated to give 6-(hydroxymethyl)-7-phenyl-3H-pyrrolo[2,3-d]pyrimidin-4-one which was reacted according to General Procedure 5 with Preparation R1c as reagents to give EXAMPLE 43. HRMS calculated for $C_{36}H_{43}N_5O_6$: 641.3214; found 642.3295 [(M+H) form].

tert-butyl (3R,4R)-4-[4-hydroxy-4-[[1-(4-methoxy-phenyl)-4-oxo-pyrazolo[3,4-d]pyrimidin-5-yl]methyl]piperidine-1-carbonyl]-3-phenyl-piperidine-1-carboxylate (EXAMPLE 44)

Using General Procedure 5 starting from 1-(4-methoxy-phenyl)-5H-pyrazolo[3,4-d]pyrimidin-4-one and Preparation R1c as reagents, EXAMPLE 44 was obtained. HRMS calculated for $C_{35}H_{42}N_6O_6$: 642.3166; found 665.3057 [(M+Na) form].

tert-butyl (3R,4R)-4-[4-hydroxy-4-[[7-(6-methoxy-2-pyridyl)-4-oxo-pyrrolo[2,3-d]pyrimidin-3-yl]methyl]piperidine-1-carbonyl]-3-phenyl-piperidine-1-carboxylate (EXAMPLE 45)

Using General Procedure 5 starting from Preparation R2bs and Preparation R1c as reagents, EXAMPLE 45 was obtained. HRMS calculated for $C_{35}H_{42}N_6O_6$: 642.3166; found 643.3231 [(M+H) form].

tert-butyl (3R,4R)-4-[4-[[7-(4-chlorophenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 46

Using General Procedure 5 starting from Preparation R2ay and Preparation R1c as reagents, EXAMPLE 46 was obtained. HRMS calculated for $C_{35}H_{40}ClN_5O_5$: 645.2718; found 646.2787 [(M+H) form].

tert-butyl (3R,4R)-4-[4-[[7-(3-chlorophenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 47)

Using General Procedure 5 starting from Preparation R2bk and Preparation R1c as reagents, EXAMPLE 47 was obtained. HRMS calculated for $C_{35}H_{40}ClN_5O_5$: 645.2718; found 646.2821 [(M+H) form].

tert-butyl (3R,4R)-4-[4-[(6-chloro-4-oxo-7-phenyl-pyrrolo[2,3-d]pyrimidin-3-yl)methyl]-4-hydroxy-piperidine-1-carbonyl]-3-phenyl-piperidine-1-carboxylate (EXAMPLE 48)

Using General Procedure 5 starting from Preparation R2ai and Preparation R1c as reagents, EXAMPLE 48 was obtained. HRMS calculated for $C_{35}H_{40}ClN_5O_5$: 645.2718; found 646.2782 [(M+H) form].

tert-butyl (3R,4R)-4-[4-[[7-(5-chloro-2-thienyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 49)

Using General Procedure 5 starting from Preparation R2bd and Preparation R1c as reagents, EXAMPLE 49 was obtained. HRMS calculated for $C_{33}H_{38}ClN_5O_5S$: 651.2282; found 652.2348 [(M+H) form].

tert-butyl (3R,4R)-4-[4-[[7-[1-(difluoromethyl)pyra-zol-4-yl]-4-oxo-pyrrolo[2,3-d]pyrimidin-3-yl]methyl]-4-hydroxy-piperidine-1-carbonyl]-3-phenyl-piperidine-1-carboxylate (EXAMPLE 50)

Using General Procedure 5 starting from Preparation R2bw and Preparation R1c as reagents, EXAMPLE 50 was obtained. HRMS calculated for $C_{33}H_{39}F_2N_7O_5$: 651.2981; found 674.2867 [(M+Na) form].

tert-butyl (3R,4R)-4-[4-[[7-(4-dimethylaminophe-nyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 51)

Using General Procedure 5 starting from Preparation R2az and Preparation R1c as reagents, EXAMPLE 51 was tert-butyl (3R,4R)-4-[4-[[7-[3-(dimethylamino)phenyl]-4-oxo-pyrrolo[2,3-d]pyrimidin-3-yl]methyl]-4-hydroxy-piperidine-1-carbonyl]-3-phenyl-piperidine-1-carboxylate (EXAMPLE 52)

Using General Procedure 5 starting from Preparation R2bm and Preparation R1c as reagents, EXAMPLE 52 was obtained. HRMS calculated for $C_{37}H_{46}N_6O_5$: 654.353; found 655.3602 [(M+H) form].

tert-butyl (3R,4R)-4-[4-[[7-(1,3-benzodioxol-5-yl)-4-oxo-pyrrolo[2,3-d]pyrimidin-3-yl]methyl]-4-hydroxy-piperidine-1-carbonyl]-3-phenyl-piperidine-1-carboxylate (EXAMPLE 53)

Using General Procedure 5 starting from Preparation R2bf and Preparation R1c as reagents, EXAMPLE 53 was obtained. HRMS calculated for $C_{36}H_{41}N_5O_7$: 655.3006; found 655.3006 [(M+H) form].

tert-butyl (3R,4R)-4-[4-[[7-[(2-chlorophenyl)methyl]-4-oxo-pyrrolo[2,3-d]pyrimidin-3-yl]methyl]-4-hydroxy-piperidine-1-carbonyl]-3-phenyl-piperidine-1-carboxylate (EXAMPLE 54)

Using General Procedure 5 starting from Preparation R2ci and Preparation R1c as reagents, EXAMPLE 54 was obtained. HRMS calculated for $C_{36}H_{42}N_5O_5Cl$: 659.2875; found 660.2949 [(M+H) form].

tert-butyl (3R,4R)-4-[4-[[7-[(3-chlorophenyl)methyl]-4-oxo-pyrrolo[2,3-d]pyrimidin-3-yl]methyl]-4-hydroxy-piperidine-1-carbonyl]-3-phenyl-piperidine-1-carboxylate (EXAMPLE 55)

Using General Procedure 5 starting from Preparation R2ch and Preparation R1c as reagents, EXAMPLE 55 was obtained. HRMS calculated for $C_{36}H_{42}ClN_5O_5$: 659.2875; found 660.2933 [(M+H) form].

tert-butyl (3R,4R)-4-[4-[[7-[(4-chlorophenyl)methyl]-4-oxo-pyrrolo[2,3-d]pyrimidin-3-yl]methyl]-4-hydroxy-piperidine-1-carbonyl]-3-phenyl-piperidine-1-carboxylate (EXAMPLE 56)

Using General Procedure 5 starting from Preparation R2cg and Preparation R1c as reagents, EXAMPLE 56 was obtained. HRMS calculated for $C_{36}H_{42}ClN_5O_5$: 659.2875; found 660.2949 [(M+H) form].

tert-butyl (3R,4R)-4-[4-[[7-(4-fluoro-3-methoxyphenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 57)

Using General Procedure 5 starting from Preparation R2e and Preparation R1c as reagents, EXAMPLE 57 was obtained. HRMS calculated for $C_{36}H_{42}FN_5O_6$: 659.3119; found 660.3194 [(M+H) form].

tert-butyl (3R,4R)-4-[4-[[7-[4-(difluoromethyl)phenyl]-4-oxo-pyrrolo[2,3-d]pyrimidin-3-yl]methyl]-4-hydroxy-piperidine-1-carbonyl]-3-phenyl-piperidine-1-carboxylate (EXAMPLE 58)

Using General Procedure 5 starting from Preparation R2aw and Preparation R1c as reagents, EXAMPLE 58 was obtained. HRMS calculated for $C_{36}H_{41}F2N_5O_5$: 661.3076; found 662.3141 [(M+H) form].

tert-butyl (3R,4R)-4-[4-hydroxy-4-[[7-(1-naphthyl)-4-oxo-pyrrolo[2,3-d]pyrimidin-3-yl]methyl]piperidine-1-carbonyl]-3-phenyl-piperidine-1-carboxylate (EXAMPLE 59)

Using General Procedure 5 starting from Preparation R2bt and Preparation R1c as reagents, EXAMPLE 59 was obtained. HRMS calculated for $C_{39}H_{43}N_5O_5$: 661.3264; found 662.3345 [(M+H) form].

tert-butyl (3R,4R)-4-[4-hydroxy-4-[[7-(2-naphthyl)-4-oxo-pyrrolo[2,3-d]pyrimidin-3-yl]methyl]piperidine-1-carbonyl]-3-phenyl-piperidine-1-carboxylate (EXAMPLE 60)

Using General Procedure 5 starting from Preparation R2bg and Preparation R1c as reagents, EXAMPLE 60 was obtained. HRMS calculated for $C_{35}H_{35}N_5O_5$: 661.3264; found 606.2715 [(M+H—C(CH3)3) form].

tert-butyl (3R,4R)-4-[4-[[7-(4-chloro-3-fluoro-phenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 61)

Using General Procedure 5 starting from Preparation R2ar and Preparation R1c as reagents, EXAMPLE 61 was obtained. HRMS calculated for $C_{35}H_{39}C_1FN_5O_5$: 663.2624; found 564.218 [(M+H-Boc) form].

tert-butyl (3R,4R)-4-[4-hydroxy-4-[[4-oxo-7-(2-trimethylsilylethoxymethyl)pyrrolo[2,3-d]pyrimidin-3-yl]methyl]piperidine-1-carbonyl]-3-phenyl-piperidine-1-carboxylate (EXAMPLE 62)

Using General Procedure 5 starting from 7-(2-trimethylsilylethoxymethyl)-3H-pyrrolo[2,3-d]pyrimidin-4-one and Preparation R1c as reagents, EXAMPLE 62 was obtained. HRMS calculated for $C_{35}H_{51}N_5O_6Si$: 665.3609; found 666.3696 [(M+H) form].

tert-butyl (3R,4R)-4-[4-[[7-(2,3-dihydro-1,4-benzodioxin-6-yl)-4-oxo-pyrrolo[2,3-d]pyrimidin-3-yl]methyl]-4-hydroxy-piperidine-1-carbonyl]-3-phenyl-piperidine-1-carboxylate (EXAMPLE 63)

Using General Procedure 5 starting from Preparation R2be and Preparation R1c as reagents, EXAMPLE 63 was obtained. HRMS calculated for $C_{37}H_{43}N_5O_7$: 669.3162; found 670.3238 [(M+H) form].

tert-butyl (3R,4R)-4-[4-[[1-(2,3-dihydro-1,4-benzodioxin-6-yl)-4-oxo-pyrazolo[3,4-d]pyrimidin-5-yl]methyl]-4-hydroxy-piperidine-1-carbonyl]-3-phenyl-piperidine-1-carboxylate (EXAMPLE 64)

Using General Procedure 5 starting from 1-(2,3-dihydro-1,4-benzodioxin-6-yl)-5H-pyrazolo[3,4-d]pyrimidin-4-one and Preparation R1c as reagents, EXAMPLE 64 was obtained. HRMS calculated for $C_{36}H_{42}N_6O_7$: 670.3115; found 693.3019 [(M+Na) form].

tert-butyl (3R,4R)-4-[4-[[7-(3,4-dimethoxyphenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 65)

Using General Procedure 5 starting from Preparation R2at and Preparation R1c as reagents, EXAMPLE 65 was obtained. HRMS calculated for $C_{37}H_{45}N_5O_7$: 671.3319; found 672.3396 [(M+H) form].

tert-butyl (3R,4R)-4-[4-[[7-(3,5-dimethoxyphenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 66)

Using General Procedure 5 starting from Preparation R2ap and Preparation R1c as reagents, EXAMPLE 66 was obtained. HRMS calculated for $C_{37}H_{45}N_5O_7$: 671.3319; found 672.3401 [(M+H) form].

tert-butyl (3R,4R)-4-[4-hydroxy-4-[(6-iodo-7-methyl-4-oxo-pyrrolo[2,3-d]pyrimidin-3-yl)methyl]piperidine-1-carbonyl]-3-phenyl-piperidine-1-carboxylate (EXAMPLE 67)

Using General Procedure 5 starting from Preparation R2aj and Preparation R1c as reagents, EXAMPLE 67 was obtained. HRMS calculated for $C_{30}H_{38}1N_5O_5$: 675.1918; found 676.1994 [(M+H) form].

tert-butyl (3R,4R)-4-[4-[[7-(3-chloro-5-methoxyphenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 68)

Using General Procedure 5 starting from Preparation R2ao and Preparation R1c as reagents, EXAMPLE 68 was obtained. HRMS calculated for $C_{36}H_{42}ClN_5O_6$: 675.2823; found 676.2891 [(M+H) form].

tert-butyl (3R,4R)-4-[4-[[7-(4-chloro-3-methoxyphenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 69)

Using General Procedure 5 starting from Preparation R2as and Preparation R1c as reagents, EXAMPLE 69 was obtained. HRMS calculated for $C_{36}H_{42}ClN_5O_6$: 675.2823; found 676.2885 [(M+H) form].

tert-butyl (3R,4R)-4-[4-[[7-(3,4-dichlorophenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 70)

Using General Procedure 5 starting from Preparation R2aq and Preparation R1c as reagents, EXAMPLE 70 was obtained. HRMS calculated for $C_{35}H_{39}Cl_2N_5O_5$: 679.2328; found 680.2399 [(M+H) form].

tert-butyl (3R,4R)-4-[4-[[7-(3,5-dichlorophenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 71)

Using General Procedure 5 starting from Preparation R2an and Preparation R1c as reagents, EXAMPLE 71 was obtained. HRMS calculated for $C_{35}H_{39}Cl_2N_5O_5$: 679.2328; found 680.2399 [(M+H) form].

tert-butyl (3R,4R)-4-[4-hydroxy-4-[[4-oxo-7-[4-(trifluoromethyl)phenyl]pyrrolo[2,3-d]pyrimidin-3-yl]methyl]piperidine-1-carbonyl]-3-phenyl-piperidine-1-carboxylate (EXAMPLE 72)

Using General Procedure 5 starting from Preparation R2av and Preparation R1c as reagents, EXAMPLE 72 was obtained. HRMS calculated for $C_{36}H_{40}F3N_5O_5$: 679.2982; found 680.3068 [(M+H) form].

tert-butyl (3R,4R)-4-[4-hydroxy-4-[[4-oxo-7-[3-(trifluoromethyl)phenyl]pyrrolo[2,3-d]pyrimidin-3-yl]methyl]piperidine-1-carbonyl]-3-phenyl-piperidine-1-carboxylate (EXAMPLE 73)

Using General Procedure 5 starting from Preparation R2bh and Preparation R1c as reagents, EXAMPLE 73 was obtained. HRMS calculated for $C_{36}H_{40}F3N_5O_5$: 679.2982; found 702.2875 [(M+Na) form].

tert-butyl (3R,4R)-4-[4-hydroxy-4-[[6-iodo-4-oxo-7-(2-trimethylsilylethoxymethyl)pyrrolo[2,3-d]pyrimidin-3-yl]methyl]piperidine-1-carbonyl]-3-phenyl-piperidine-1-carboxylate (EXAMPLE 74)

Using General Procedure 5 starting from Preparation R2al and Preparation R1c as reagents, EXAMPLE 74 was obtained. HRMS calculated for $C_{35}H_{50}IN_5O_6Si$: 791.2575; found 792.265 [(M+H) form].

tert-butyl (3R,4R)-4-[4-hydroxy-4-[[4-oxo-7-[3-(trifluoromethoxy)phenyl]pyrrolo[2,3-d]pyrimidin-3-yl]methyl]piperidine-1-carbonyl]-3-phenyl-piperidine-1-carboxylate (EXAMPLE 75)

Using General Procedure 5 starting from Preparation R2bo and Preparation R1c as reagents, EXAMPLE 75 was obtained. HRMS calculated for $C_{36}H_{40}F3N_5O_6$: 695.2931; found 696.2997 [(M+H) form].

tert-butyl (3R,4R)-4-[4-hydroxy-4-[[4-oxo-7-[4-(trifluoromethoxy)phenyl]pyrrolo[2,3-d]pyrimidin-3-yl]methyl]piperidine-1-carbonyl]-3-phenyl-piperidine-1-carboxylate (EXAMPLE 76)

Using General Procedure 5 starting from Preparation R2ba and Preparation R1c as reagents, EXAMPLE 76 was obtained. HRMS calculated for $C_{36}H_{40}F3N_5O_6$: 695.2931; found 696.3006 [(M+H) form].

tert-butyl (3R,4R)-4-[4-hydroxy-4-[[7-(3-morpholinophenyl)-4-oxo-pyrrolo[2,3-d]pyrimidin-3-yl]methyl]piperidine-1-carbonyl]-3-phenyl-piperidine-1-carboxylate (EXAMPLE 77)

Using General Procedure 5 starting from Preparation R2bn and Preparation R1c as reagents, EXAMPLE 77 was obtained. HRMS calculated for $C_{39}H_{48}N_6O_6$: 696.3635; found 697.3708 [(M+H) form].

tert-butyl (3R,4R)-4-[4-hydroxy-4-[[4-oxo-7-(3,4,5-trimethoxyphenyl)pyrrolo[2,3-d]pyrimidin-3-yl]methyl]piperidine-1-carbonyl]-3-phenyl-piperidine-1-carboxylate (EXAMPLE 78)

Using General Procedure 5 starting from Preparation R2am and Preparation R1c as reagents, EXAMPLE 78 was obtained. HRMS calculated for $C_{38}H_{47}N_5O_8$: 701.3425; found 702.3487 [(M+H) form].

tert-butyl (3R,4R)-4-[4-[[7-(4-benzyloxyphenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 79)

Using General Procedure 5 starting from Preparation R2bb and Preparation R1c as reagents, EXAMPLE 79 was obtained. HRMS calculated for $C_{42}H_{47}N_5O_6$: 717.3527; found 718.3603 [(M+H) form].

tert-butyl (3R,4R)-4-[4-[[7-(3-benzyloxyphenyl)-4-oxo-pyrrolo[2,3-d]pyrimidin-3-yl]methyl]-4-hydroxy-piperidine-1-carbonyl]-3-phenyl-piperidine-1-carboxylate (EXAMPLE 80)

Using General Procedure 5 starting from Preparation R2bq and Preparation R1c as reagents, EXAMPLE 80 was obtained. HRMS calculated for $C_{42}H_{47}N_5O_6$: 717.3527; found 740.3423 [(M+Na) form].

tert-butyl (3R,4R)-4-[4-hydroxy-4-[[7-[3-[(4-methylpiperazin-1-yl)methyl]phenyl]-4-oxo-pyrrolo[2,3-d]pyrimidin-3-yl]methyl]piperidine-1-carbonyl]-3-phenyl-piperidine-1-carboxylate (EXAMPLE 81)

Using General Procedure 5 starting from Preparation R2bi and Preparation R1c as reagents, EXAMPLE 81 was obtained. HRMS calculated for $C_{41}H_{53}N_7O_5$: 723.4108; found 724.4175 [(M+H) form].

tert-butyl (3R,4R)-4-[4-[[6-cyano-4-oxo-7-(2-trimethylsilylethoxymethyl)pyrrolo[2,3-d]pyrimidin-3-yl]methyl]-4-hydroxy-piperidine-1-carbonyl]-3-phenyl-piperidine-1-carboxylate (EXAMPLE 82)

EXAMPLE 74 was dissolved in PDO and copper cyanide (4.2 eq) tetraethylammonium cyanide (1.05 eq.), $Pd_2(dba)_3$ (0.1 eq.), and 1,1'-bis(diphenylphosphino)ferrocene (0.4 eq.) were added. The mixture was heated and stirred at 110° C. till the reaction was completed. The residue was purified by flash chromatography in DCM-MeOH gradient to give EXAMPLE 82. HRMS calculated for $C_{36}H_{50}N_6O_6Si$: 690.3561; found 691.3637 [(M+H) form].

3-[[4-hydroxy-1-[(3R,4R)-3-phenylpiperidine-4-carbonyl]-4-piperidyl]methyl]-7H-pyrrolo[2,3-d]pyrimidin-4-one (EXAMPLE 83)

Using General Procedure 5 starting from 3H,4H,7H-pyrrolo[2,3-d]pyrimidin-4-one and Preparation R1c as reagents, the resulted Boc-protected crude product was reacted using General Procedure 6, to give EXAMPLE 83 as HCl salt. HRMS calculated for $C_{24}H_{29}N_5O_3$: 435.2271; found 436.2345 [(M+H) form].

3-[[4-hydroxy-1-[(3R,4R)-3-phenylpiperidine-4-carbonyl]-4-piperidyl]methyl]-7-methyl-pyrrolo[2,3-d]pyrimidin-4-one (EXAMPLE 84)

Using General Procedure 6 starting from EXAMPLE 1 as reagent, EXAMPLE 84 was obtained as HCl salt. HRMS calculated for $C_{25}H_{31}N_5O_3$: 449.2427; found 450.2517 [(M+H) form].

3-[[4-hydroxy-1-[(3R,4R)-3-phenylpiperidine-4-carbonyl]-4-piperidyl]methyl]thieno[2,3-d]pyrimidin-4-one (EXAMPLE 85)

Using General Procedure 6 starting from EXAMPLE 2 as reagent, EXAMPLE 85 was obtained as HCl salt. HRMS calculated for $C_{24}H_{28}N_4O_3S$: 452.1882; found 453.1933 [(M+H) form].

7-ethyl-3-[[4-hydroxy-1-[(3R,4R)-3-phenylpiperidine-4-carbonyl]-4-piperidyl]methyl]pyrrolo[2,3-d]pyrimidin-4-one (EXAMPLE 86)

Using General Procedure 6 starting from EXAMPLE 3 as reagent, EXAMPLE 86 was obtained as HCl salt. HRMS calculated for $C_{26}H_{33}N_5O_3$: 463.2583; found 464.2654 [(M+H) form].

3-[[4-hydroxy-1-[(3R,4R)-3-phenylpiperidine-4-carbonyl]-4-piperidyl]methyl]-7-prop-2-ynyl-pyrrolo[2,3-d]pyrimidin-4-one (EXAMPLE 87)

Using General Procedure 6 starting from EXAMPLE 4 as reagent, EXAMPLE 87 was obtained as HCl salt. HRMS calculated for $C_{27}H_{31}N_5O_3$: 473.2427; found 474.2502 [(M+H) form].

7-cyclopropyl-3-[[4-hydroxy-1-[(3R,4R)-3-phenylpiperidine-4-carbonyl]-4-piperidyl]methyl]pyrrolo[2,3-d]pyrimidin-4-one (EXAMPLE 88)

Using General Procedure 6 starting from EXAMPLE 5 as reagent, EXAMPLE 88 was obtained as HCl salt. HRMS calculated for $C_{27}H_{33}N_5O_3$: 475.2583; found 476.2668 [(M+H) form].

3-[[4-hydroxy-1-[(3R,4R)-3-phenylpiperidine-4-carbonyl]-4-piperidyl]methyl]-7-isopropyl-pyrrolo[2,3-d]pyrimidin-4-one (EXAMPLE 89)

Using General Procedure 5 starting from Preparation R2by and Preparation R1c as reagents, the resulted Boc-protected crude product was reacted using General Procedure 6, to give EXAMPLE 89 as HCl salt. HRMS calculated for $C_{27}H_{35}N_5O_3$: 477.274; found 478.2819 [(M+H) form].

7-(2-hydroxyethyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 90)

Using General Procedure 5 starting from Preparation R2ce and Preparation R1c as reagents, the resulted Boc-protected crude product was reacted using General Procedure 6, to give EXAMPLE 90 as HCl salt. HRMS calculated for $C_{26}H_{33}N_5O_4$: 479.2533; found (NMR available form].

7-(2-fluoroethyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 91)

Using General Procedure 5 starting from Preparation R2cd and Preparation R1c as reagents, the resulted Boc-protected crude product was reacted using General Procedure 6, to give EXAMPLE 91 as HCl salt. HRMS calculated for $C_{26}H_{32}N_5O_3F$: 481.2489; found 482.2555 [(M+H) form].

7-chloro-3-[[4-hydroxy-1-[(3R,4R)-3-phenylpiperidine-4-carbonyl]-4-piperidyl]methyl]thieno[3,4-d]pyrimidin-4-one (EXAMPLE 92)

Using General Procedure 6 starting from EXAMPLE 6 as reagent, EXAMPLE 92 was obtained as HCl salt. HRMS calculated for $C_{24}H_{27}ClN_4O_3S$: 486.1492; found 487.1544 [(M+H) form].

7-buta-2,3-dienyl-3-[[4-hydroxy-1-[(3R,4R)-3-phenylpiperidine-4-carbonyl]-4-piperidyl]methyl]pyrrolo[2,3-d]pyrimidin-4-one (EXAMPLE 93)

Using General Procedure 6 starting from EXAMPLE 7 as reagents, EXAMPLE 93 was obtained as HCl salt. HRMS calculated for $C_{28}H_{33}N_5O_3$: 487.2583; found 488.2657 [(M+H) form].

7-cyclobutyl-3-[[4-hydroxy-1-[(3R,4R)-3-phenylpiperidine-4-carbonyl]-4-piperidyl]methyl]pyrrolo[2,3-d]pyrimidin-4-one (EXAMPLE 94)

Using General Procedure 5 starting from Preparation R2ca and Preparation R1c as reagents, the resulted Boc-protected crude product was reacted using General Procedure 6, to give EXAMPLE 94 as HCl salt. HRMS calculated for $C_{28}H_{35}N_5O_3$: 489.274; found 490.2796 [(M+H) form].

7-(cyclopropylmethyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 95)

Using General Procedure 6 starting from EXAMPLE 8 as reagent, EXAMPLE 95 was obtained as HCl salt. HRMS calculated for $C_{28}H_{35}N_5O_3$: 489.274; found 490.2817 [(M+H) form].

3-[[4-hydroxy-1-[(3R,4R)-3-phenylpiperidine-4-carbonyl]-4-piperidyl]methyl]-7-isobutyl-pyrrolo[2,3-d]pyrimidin-4-one (EXAMPLE 96)

Using General Procedure 6 starting from EXAMPLE 9 as reagent, EXAMPLE 96 was obtained as HCl salt. HRMS calculated for $C_{28}H_{37}N_5O_3$: 491.2896; found 492.2963 [(M+H) form].

7-(2,2-difluoroethyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 97)

Using General Procedure 5 starting from Preparation R2cc and Preparation R1c as reagents, the resulted Boc-protected crude product was reacted using General Procedure 6, to give EXAMPLE 97 as HCl salt. HRMS calculated for $C_{26}H_{31}N_5O_3F_2$: 499.2395; found 500.2485 [(M+H) form].

3-[[4-hydroxy-1-[(3R,4R)-3-phenylpiperidine-4-carbonyl]-4-piperidyl]methyl]-9-methyl-pyrimido[4,5-b]indol-4-one (EXAMPLE 98)

Using General Procedure 6 starting from EXAMPLE 10 as reagent, EXAMPLE 98 was obtained as HCl salt. HRMS calculated for $C_{29}H_{33}N_5O_3$: 499.2583; found 500.2677 [(M+H) form].

7-(cyclobutylmethyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 99)

Using General Procedure 6 starting from EXAMPLE 11 as reagent, EXAMPLE 99 was obtained as HCl salt. HRMS calculated for $C_{29}H_{37}N_5O_3$: 503.2896; found 504.2957 [(M+H) form].

7-(2-dimethylaminoethyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 100)

Using General Procedure 6 starting from EXAMPLE 12 as reagent, EXAMPLE 100 was obtained as HCl salt. HRMS calculated for $C_{28}H_{38}N_6O_3$: 506.3005; found 254.1581 [(M+2H)2+ form].

3-[[4-hydroxy-1-[(3R,4R)-3-phenylpiperidine-4-carbonyl]-4-piperidyl]methyl]-7-phenyl-pyrrolo[2,3-d]pyrimidin-4-one (EXAMPLE 101)

Using General Procedure 6 starting from EXAMPLE 13 as reagent, EXAMPLE 101 was obtained as HCl salt. HRMS calculated for $C_{30}H_{33}N_5O_3$: 511.2583; found 512.2648 [(M+H) form].

3-[[4-hydroxy-1-[(3R,4R)-3-phenylpiperidine-4-carbonyl]-4-piperidyl]methyl]-7-phenyl-5H-pyrrolo[3,2-d]pyrimidin-4-one (EXAMPLE 102)

Using General Procedure 6 starting from EXAMPLE 14 as reagents, EXAMPLE 102 was obtained as HCl salt. HRMS calculated for $C_{30}H_{33}N_5O_3$: 511.2583; found 512.2647 [(M+H) form].

5-[[4-hydroxy-1-[(3R,4R)-3-phenylpiperidine-4-carbonyl]-4-piperidyl]methyl]-1-phenyl-pyrazolo[3,4-d]pyrimidin-4-one (EXAMPLE 103)

Using General Procedure 6 starting from EXAMPLE 16 as reagent, EXAMPLE 103 was obtained as HCl salt. HRMS calculated for $C_{29}H_{32}N_6O_3$: 512.2536; found 513.2623 [(M+H) form].

3-[[4-hydroxy-1-[(3R,4R)-3-phenylpiperidine-4-carbonyl]-4-piperidyl]methyl]-7-(2-pyridyl)pyrrolo[2,3-d]pyrimidin-4-one (EXAMPLE 104)

Using General Procedure 6 starting from EXAMPLE 15 as reagent, EXAMPLE 104 was obtained as HCl salt. HRMS calculated for $C_{29}H_{32}N_6O_3$: 512.2536; found 257.134 [(M+2H)2+ form].

3-[[4-hydroxy-1-[(3R,4R)-3-phenylpiperidine-4-carbonyl]-4-piperidyl]methyl]-7-(3-pyridyl)pyrrolo[2,3-d]pyrimidin-4-one (EXAMPLE 105)

Using General Procedure 5 starting from Preparation R2bu and Preparation R1c as reagents, the resulted Boc-protected crude product was reacted using General Procedure 6, to give EXAMPLE 105 as HCl salt. HRMS calculated for $C_{29}H_{32}N_6O_3$: 512.2536; found 513.261 [(M+H) form].

3-[[4-hydroxy-1-[(3R,4R)-3-phenylpiperidine-4-carbonyl]-4-piperidyl]methyl]-7-(4-pyridyl)pyrrolo[2,3-d]pyrimidin-4-one (EXAMPLE 106)

Using General Procedure 5 starting from Preparation R2bv and Preparation R1c as reagents, the resulted Boc-protected crude product was reacted using General Procedure 6, to give EXAMPLE 106 as HCl salt. HRMS calculated for $C_{29}H_{32}N_6O_3$: 512.2536; found 513.2609 [(M+H) form].

1-[[4-hydroxy-1-[(3R,4R)-3-phenylpiperidine-4-carbonyl]-4-piperidyl]methyl]-9-phenyl-purin-6-one (EXAMPLE 107)

Using General Procedure 6 starting from EXAMPLE 17 as reagent, EXAMPLE 107 was obtained as HCl salt. HRMS calculated for $C_{29}H_{32}N_6O_3$: 512.2536; found 513.2616 [(M+H) form].

7-bromo-3-[[4-hydroxy-1-[(3R,4R)-3-phenylpiperidine-4-carbonyl]-4-piperidyl]methyl]pyrrolo[2,1-f][1,2,4]triazin-4-one (EXAMPLE 108)

Using General Procedure 6 starting from EXAMPLE 18 as reagent, EXAMPLE 108 was obtained as HCl salt. HRMS calculated for $C_{24}H_{28}BrN_5O_3$: 513.1376; found 514.1462 [(M+H) form].

6-[[4-hydroxy-1-[(3R,4R)-3-phenylpiperidine-4-carbonyl]-4-piperidyl]methyl]-3-phenyl-isoxazolo[4,5-d]pyrimidin-7-one (EXAMPLE 109)

Using General Procedure 6 starting from EXAMPLE 19 as reagent, EXAMPLE 109 was obtained as HCl salt. HRMS calculated for $C_{29}H_{31}N_5O_4$: 513.2376; found 514.2451 [(M+H) form].

3-[[4-hydroxy-1-[(3R,4R)-3-phenylpiperidine-4-carbonyl]-4-piperidyl]methyl]-7-pyrimidin-2-yl-pyrrolo[2,3-d]pyrimidin-4-one (EXAMPLE 110)

Using General Procedure 6 starting from EXAMPLE 20 as reagent, EXAMPLE 110 was obtained as HCl salt. HRMS calculated for $C_{28}H_{31}N_7O_3$: 513.2488; found 257.6326 [(M+2H)2+ form].

6-[[4-hydroxy-1-[(3R,4R)-3-phenylpiperidine-4-carbonyl]-4-piperidyl]methyl]-3-phenyl-triazolo[4,5-d]pyrimidin-7-one (EXAMPLE 111)

Using General Procedure 6 starting from EXAMPLE 21 as reagent, EXAMPLE 111 was obtained as HCl salt. HRMS calculated for $C_{28}H_{31}N_7O_3$: 513.2488; found 514.2576 [(M+H) form].

3-[(4-hydroxy-1-{[(3R,4R)-3-phenylpiperidin-4-yl]carbonyl}piperidin-4-yl)methyl]-6,8-dimethylpyrimido[5,4-b]indolizin-4(3H)-one (EXAMPLE 112)

Using General Procedure 6 starting from EXAMPLE 22 as reagent, EXAMPLE 112 was obtained as HCl salt. HRMS calculated for $C_{29}H_{34}N_6O_3$: 514.2692; found 515.2757 [(M+H) form].

3-[[4-hydroxy-1-[(3R,4R)-3-phenylpiperidine-4-carbonyl]-4-piperidyl]methyl]-7-(1-methylimidazol-4-yl)pyrrolo[2,3-d]pyrimidin-4-one (EXAMPLE 113)

Using General Procedure 6 starting from EXAMPLE 23 as reagent, EXAMPLE 113 was obtained as HCl salt. HRMS calculated for $C_{28}H_{33}N_7O_3$: 515.2645; found 516.2728 [(M+H) form].

3-[[4-hydroxy-1-[(3R,4R)-3-phenylpiperidine-4-carbonyl]-4-piperidyl]methyl]-7-(1-methylpyrazol-4-yl)pyrrolo[2,3-d]pyrimidin-4-one (EXAMPLE 114)

Using General Procedure 5 starting from Preparation R2bx and Preparation R1c as reagents, the resulted Boc-protected crude product was reacted using General Procedure 6, to give EXAMPLE 114 as HCl salt. HRMS calculated for $C_{28}H_{33}N_7O_3$: 515.2645; found 516.2716 [(M+H) form].

3-[[4-hydroxy-1-[(3R,4R)-3-phenylpiperidine-4-carbonyl]-4-piperidyl]methyl]-7-(2-thienyl)pyrrolo[2,3-d]pyrimidin-4-one (EXAMPLE 115)

Using General Procedure 6 starting from EXAMPLE 25 as reagent, EXAMPLE 115 was obtained as HCl salt. HRMS calculated for $C_{28}H_{31}N_5O_3S$: 517.2148; found 518.2231 [(M+H) form].

3-[[4-hydroxy-1-[(3R,4R)-3-phenylpiperidine-4-carbonyl]-4-piperidyl]methyl]-7-(3-thienyl)pyrrolo[2,3-d]pyrimidin-4-one (EXAMPLE 116)

Using General Procedure 6 starting from EXAMPLE 24 as reagent, EXAMPLE 116 was obtained as HCl salt. HRMS calculated for $C_{28}H_{31}N_5O_3S$: 517.2148; found 518.2233 [(M+H) form].

3-[[4-hydroxy-1-[(3R,4R)-3-phenyl-1-(2,2,2-trifluoroethyl)piperidine-4-carbonyl]-4-piperidyl]methyl]-7H-pyrrolo[2,3-d]pyrimidin-4-one (EXAMPLE 117)

EXAMPLE 62 (610 mg, 0.92 mmol) was dissolved in 12 ml DCM, then TFA (211 μl, 2.73 mmol, 3 eq.) and formic acid (399 μl, 10.6 mmol, 11.5 eq.) were added. The mixture was stirred at r.t. for 118 hours, then potassium carbonate (2.22g 16.1 mmol) was added. The solution was extrated with DCM (2×70 ml) and organic phase was dried (MgSO$_4$) and evaporated.

112 mg (0.2 mmol) of crude 3-[[4-hydroxy-1-[(3R,4R)-3-phenylpiperidine-4-carbonyl]-4-piperidyl]methyl]-7-(2-trimethylsilylethoxymethyl)pyrrolo[2,3-d]pyrimidin-4-one product was solved in 2 ml dry THF, then triethyl amine (42 μl, 0.3 mmol, 1.5 eq.) and 2,2,2-trifluoroethyl trifluoromethanesulfonate (32 μl, 0.22 mol, 1.2 eq.) were added. The mixture was stirred at r.t. for 141 hours, then 5 ml water was added. The solution was extracted with DCM (2×10 ml) and organic phase was dried (MgSO$_4$) and evaporated The obtained 3-[[4-hydroxy-1-[(3R,4R)-3-phenyl-1-(2,2,2-trifluoroethyl)piperidine-4-carbonyl]-4-piperidyl]methyl]-7-(2-trimethylsilylethoxymethyl)pyrrolo[2,3-d]pyrimidin-4-one was solved in 270 μl dry THF, and tetrabutylammonium fluoride (270 μl, 1M in THF, 0.27 mmol) and molecular sieves were added and stirred at 75° C. for 20 hours, then the molecular sieves was filtered off and the residue was purified by preparative HPLC in 25 mM NH$_4$HCO$_3$-acetonitrile gradient method, to give EXAMPLE 117. HRMS calculated for C$_{26}$H$_{30}$F3N$_5$O$_3$: 517.2301; found 518.2361 [(M+H) form].

3-[[4-hydroxy-1-[(3R,4R)-3-phenylpiperidine-4-carbonyl]-4-piperidyl]methyl]-7-(2,2,2-trifluoro-ethyl)pyrrolo[2,3-d]pyrimidin-4-one (EXAMPLE 118)

Using General Procedure 6 starting from EXAMPLE 26 as reagent, EXAMPLE 118 was obtained as HCl salt. HRMS calculated for C$_{26}$H$_{30}$F3N$_5$O$_3$: 517.2301; found 518.2386 [(M+H) form].

3-[[4-hydroxy-1-[(3R,4R)-3-phenylpiperidine-4-carbonyl]-4-piperidyl]methyl]-7-thiazol-2-yl-pyrrolo[2,3-d]pyrimidin-4-one (EXAMPLE 119)

Using General Procedure 6 starting from EXAMPLE 27 as reagent, EXAMPLE 119 was obtained as HCl salt. HRMS calculated for C$_{27}$H$_{30}$N$_6$O$_3$S: 518.21; found 519.2181 [(M+H) form].

7-[3-(dimethylamino)propyl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 120)

Using General Procedure 6 starting from EXAMPLE 28 as reagent, EXAMPLE 120 was obtained as HCl salt. HRMS calculated for C$_{29}$H$_{40}$N$_6$O$_3$: 520.3162; found 261.1666 [(M+2H)2+ form].

3-[[4-hydroxy-1-[(3R,4R)-1-methyl-3-phenyl-piperidine-4-carbonyl]-4-piperidyl]methyl]-7-phenyl-pyrrolo[2,3-d]pyrimidin-4-one (EXAMPLE 121)

Using General Procedure 7 starting from EXAMPLE 101 and methyl iodide as reagents, EXAMPLE 121 was obtained as HCl salt. HRMS calculated for C$_{31}$H$_{35}$N$_5$O$_3$: 525.274; found 526.2802 [(M+H) form].

7-benzyl-3-[[4-hydroxy-1-[(3R,4R)-3-phenylpiperidine-4-carbonyl]-4-piperidyl]methyl]pyrrolo[2,3-d]pyrimidin-4-one (EXAMPLE 122)

Using General Procedure 6 starting from EXAMPLE 31 as reagent, EXAMPLE 122 was obtained as HCl salt. HRMS calculated for C$_{31}$H$_{35}$N$_5$O$_3$: 525.274; found 526.2822 [(M+H) form].

3-[[4-hydroxy-1-[(3R,4R)-3-phenylpiperidine-4-carbonyl]-4-piperidyl]methyl]-7-(p-tolyl)pyrrolo[2,3-d]pyrimidin-4-one (EXAMPLE 123)

Using General Procedure 6 starting from EXAMPLE 30 as reagent, EXAMPLE 123 was obtained as HCl salt. HRMS calculated for C$_{31}$H$_{35}$N$_5$O$_3$: 525.274; found 526.2816 [(M+H) form].

3-[[4-hydroxy-1-[(3R,4R)-3-phenylpiperidine-4-carbonyl]-4-piperidyl]methyl]-7-(m-tolyl)pyrrolo[2,3-d]pyrimidin-4-one (EXAMPLE 124)

Using General Procedure 6 starting from EXAMPLE 29 as reagent, EXAMPLE 124 was obtained as HCl salt. HRMS calculated for C$_{31}$H$_{35}$N$_5$O$_3$: 525.274; found 526.2825 [(M+H) form].

3-[[4-hydroxy-1-[(3R,4R)-3-phenylpiperidine-4-carbonyl]-4-piperidyl]methyl]-6-methyl-7-phenyl-pyrrolo[2,3-d]pyrimidin-4-one (EXAMPLE 125)

Using General Procedure 6 starting from EXAMPLE 32 as reagent, EXAMPLE 125 was obtained as HCl salt. HRMS calculated for C$_{31}$H$_{35}$N$_5$O$_3$: 525.274; found 526.2827 [(M+H) form].

3-[[4-hydroxy-1-[(3R,4R)-3-phenylpiperidine-4-carbonyl]-4-piperidyl]methyl]-7-(6-methyl-2-pyridyl)pyrrolo[2,3-d]pyrimidin-4-one (EXAMPLE 126)

Using General Procedure 5 starting from Preparation R2br and Preparation R1c as reagents, the resulted Boc-protected crude product was reacted using General Procedure 6, to give EXAMPLE 126 as HCl salt. HRMS calculated for C$_{30}$H$_{34}$N$_6$O$_3$: 526.2692; found 527.2764 [(M+H) form].

tert-butyl (3R,4R)-4-[4-hydroxy-4-[(4-oxo-7-phenyl-thieno[3,4-d]pyrimidin-3-yl)methyl]piperidine-1-carbonyl]-3-phenyl-piperidine-1-carboxylate (EXAMPLE 127)

EXAMPLE 6 (370 mg, 0.63 mmol) was dissolved in 2 ml THF and 2 ml water, then phenyl boronic acid (308 mg, 2.52 mmol, 4 eq.), AtaPhos*PdCl$_2$ (8.6 mg, 0.012 mmol, 0.2 eq.), cesium carbonate (617 mg, 1.89 mmol, 3 eq.) were added. The mixture was heated and stirred in Anton Paar microwave reactor for 1 hour at 100° C. The residue was purified by preparative HPLC in 5 mM NH$_4$HCO$_3$-MeCN gradient method, to give EXAMPLE 127. HRMS calculated for C$_{35}$H$_{40}$N$_4$O$_5$S: 628.2719; found 629.2788 [(M+H) form].

3-[[4-hydroxy-1-[(3R,4R)-3-phenylpiperidine-4-carbonyl]-4-piperidyl]methyl]-7-(6-oxo-1H-pyridin-2-yl)pyrrolo[2,3-d]pyrimidin-4-one (EXAMPLE 128)

Using General Procedure 6 starting from EXAMPLE 45 as reagents, EXAMPLE 128 was obtained. HRMS calculated for C$_{29}$H$_{32}$N$_6$O$_4$: 528.2485; found 529.2567 [(M+H) form].

6-[[4-hydroxy-1-[(3R,4R)-3-phenylpiperidine-4-carbonyl]-4-piperidyl]methyl]-3-phenyl-isothiazolo[4,5-d]pyrimidin-7-one (EXAMPLE 129)

Using General Procedure 6 starting from EXAMPLE 33 as reagent, EXAMPLE 129 was obtained. HRMS calculated for C$_{29}$H$_{31}$N$_5$O$_3$S: 529.2148; found 530.2223 [(M+H) form].

7-(4-fluorophenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 130)

Using General Procedure 6 starting from EXAMPLE 34 as reagent, EXAMPLE 130 was obtained. HRMS calculated for C$_{30}$H$_{30}$FN$_5$O$_3$: 529.2489; found 530.2584 [(M+H) form].

7-(3-fluorophenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 131)

Using General Procedure 6 starting from EXAMPLE 35 as reagents, EXAMPLE 131 was obtained. HRMS calculated for $C_{30}H_{32}FN_5O_3$: 529.2489; found 530.2571 [(M+H) form].

3-[[4-hydroxy-1-[(3R,4R)-3-phenylpiperidine-4-carbonyl]-4-piperidyl]methyl]-7-(5-methyl-2-thienyl)pyrrolo[2,3-d]pyrimidin-4-one (EXAMPLE 132)

Using General Procedure 6 starting from EXAMPLE 37 as reagent, EXAMPLE 132 was obtained. HRMS calculated for $C_{29}H_{33}N_5O_3S$: 531.2304; found 532.2361 [(M+H) form].

3-[[4-hydroxy-1-[(3R,4R)-3-phenylpiperidine-4-carbonyl]-4-piperidyl]methyl]-7-(1-methyl-4-piperidyl)pyrrolo[2,3-d]pyrimidin-4-one (EXAMPLE 133)

Using General Procedure 6 starting from EXAMPLE 38 as reagent, EXAMPLE 133 was obtained. HRMS calculated for $C_{30}H_{40}N_6O_3$: 532.3162; found 267.1658 [(M+2H)2+ form].

4-[3-[[4-hydroxy-1-[(3R,4R)-3-phenylpiperidine-4-carbonyl]-4-piperidyl]methyl]-4-oxo-pyrrolo[2,3-d]pyrimidin-7-yl]benzonitrile (EXAMPLE 134)

Using General Procedure 6 starting from EXAMPLE 39 as reagent, EXAMPLE 134 was obtained. HRMS calculated for $C_{31}H_{32}N_6O_3$: 536.2536; found 537.2599 [(M+H) form].

3-[[4-hydroxy-1-[(3R,4R)-3-phenylpiperidine-4-carbonyl]-4-piperidyl]methyl]-7-(4-methoxyphenyl)pyrrolo[2,3-d]pyrimidin-4-one (EXAMPLE 135)

Using General Procedure 6 starting from EXAMPLE 40 as reagents, EXAMPLE 135 was obtained. HRMS calculated for $C_{31}H_{35}N_5O_4$: 541.2689; found 542.2784 [(M+H) form].

3-[[4-hydroxy-1-[(3R,4R)-3-phenylpiperidine-4-carbonyl]-4-piperidyl]methyl]-7-(3-methoxyphenyl)pyrrolo[2,3-d]pyrimidin-4-one (EXAMPLE 136)

Using General Procedure 6 starting from EXAMPLE 41 as reagent, EXAMPLE 136 was obtained. HRMS calculated for $C_{31}H_{35}N_5O_4$: 541.2689; found 542.2777 [(M+H) form].

7-[4-(hydroxymethyl)phenyl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 137)

Using General Procedure 6 starting from EXAMPLE 42 as reagent, EXAMPLE 137 was obtained. HRMS calculated for $C_{31}H_{35}N_5O_4$: 541.2689; found 542.2787 [(M+H) form].

7-[3-(hydroxymethyl)phenyl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 138)

Using General Procedure 5 starting from Preparation R2bj and Preparation R1c as reagents, the resulted Boc-protected crude product was reacted using General Procedure 6, to give EXAMPLE 138. HRMS calculated for $C_{31}H_{35}N_5O_4$: 541.2689; found 542.2769 [(M+H) form].

6-(hydroxymethyl)-3-[[4-hydroxy-1-[(3R,4R)-3-phenylpiperidine-4-carbonyl]-4-piperidyl]methyl]-7-phenyl-pyrrolo[2,3-d]pyrimidin-4-one (EXAMPLE 139)

Using General Procedure 6 starting from EXAMPLE 43 as reagent, EXAMPLE 139 was obtained. HRMS calculated for $C_{31}H_{35}N_5O_4$: 541.2689; found 542.2763 [(M+H) form].

3-[[4-hydroxy-1-[(3R,4R)-3-phenylpiperidine-4-carbonyl]-4-piperidyl]methyl]-7-(6-methoxy-2-pyridyl)pyrrolo[2,3-d]pyrimidin-4-one (EXAMPLE 140)

Using General Procedure 6 starting from EXAMPLE 45 as reagent, EXAMPLE 140 was obtained. HRMS calculated for $C_{30}H_{34}N_6O_4$: 542.2642; found 543.2698 [(M+H) form].

7-(4-fluorophenyl)-3-[[4-hydroxy-1-[(3R,4R)-1-methyl-3-phenyl-piperidine-4-carbonyl]-4-piperidyl]methyl]pyrrolo[2,3-d]pyrimidin-4-one (EXAMPLE 141)

Using General Procedure 7 starting from EXAMPLE 130 and methyl iodide as reagents, EXAMPLE 141 was obtained. HRMS calculated for $C_{31}H_{34}N_5O_3F$: 543.2646; found 544.2721 [(M+H) form].

7-(3-chlorophenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 142)

Using General Procedure 6 starting from EXAMPLE 47 as reagent, EXAMPLE 142 was obtained. HRMS calculated for $C_{30}H_{32}ClN_5O_3$: 545.2194; found 546.2248 [(M+H) form].

7-(4-chlorophenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 143)

Using General Procedure 6 starting from EXAMPLE 46 as reagent, EXAMPLE 143 was obtained. HRMS calculated for $C_{30}H_{32}ClN_5O_3$: 545.2194; found 546.2262 [(M+H) form].

6-chloro-3-[[4-hydroxy-1-[(3R,4R)-3-phenylpiperidine-4-carbonyl]-4-piperidyl]methyl]-7-phenyl-pyrrolo[2,3-d]pyrimidin-4-one (EXAMPLE 144)

Using General Procedure 6 starting from EXAMPLE 48 as reagent, EXAMPLE 144 was obtained. HRMS calculated for $C_{30}H_{32}ClN_5O_3$: 545.2194; found 546.2277 [(M+H) form].

7-(5-chloro-2-thienyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 145)

Using General Procedure 6 starting from EXAMPLE 49 as reagent, EXAMPLE 145 was obtained. HRMS calculated for $C_{28}H_{30}ClN_5O_3S$: 551.1758; found 552.1844 [(M+H) form].

7-[1-(difluoromethyl)pyrazol-4-yl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 146)

Using General Procedure 6 starting from EXAMPLE 50 as reagent, EXAMPLE 146 was obtained. HRMS calculated for $C_{28}H_{31}F2N_7O_3$: 551.2457; found 552.254 [(M+H) form].

3-[[1-[(3R,4R)-1-acetyl-3-phenyl-piperidine-4-carbonyl]-4-hydroxy-4-piperidyl]methyl]-7-phenyl-pyrrolo[2,3-d]pyrimidin-4-one (EXAMPLE 147)

Using General Procedure 8 starting from EXAMPLE 101 and acetic acid as reagents, EXAMPLE 147 was obtained. HRMS calculated for $C_{32}H_{35}N_5O_4$: 553.2689; found 554.2757 [(M+H) form].

7-(4-dimethylaminophenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 148)

Using General Procedure 6 starting from EXAMPLE 51 as reagent, EXAMPLE 148 was obtained. HRMS calculated for $C_{32}H_{38}N_6O_3$: 554.3005; found 555.3076 [(M+H) form].

7-[3-(dimethylamino)phenyl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 149)

Using General Procedure 6 starting from EXAMPLE 52 as reagent, EXAMPLE 149 was obtained. HRMS calculated for $C_{32}H_{38}N_6O_3$: 554.3005; found 555.3086 [(M+H) form].

7-(1,3-benzodioxol-5-yl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 150)

Using General Procedure 6 starting from EXAMPLE 53 as reagent, EXAMPLE 150 was obtained. HRMS calculated for $C_{31}H_{33}N_5O_5$: 555.2482; found 556.2556 [(M+H) form].

3-[[4-hydroxy-1-[(3R,4R)-1-methyl-3-phenyl-piperidine-4-carbonyl]-4-piperidyl]methyl]-7-(4-methoxy-phenyl)pyrrolo[2,3-d]pyrimidin-4-one (EXAMPLE 151)

Using General Procedure 7 starting from EXAMPLE 135 and methyl iodide as reagents, EXAMPLE 151 was obtained. HRMS calculated for $C_{32}H_{37}N_5O_4$: 555.2845; found 556.2922 [(M+H) form].

7-(3-chlorophenyl)-3-[[4-hydroxy-1-[(3R,4R)-1-methyl-3-phenyl-piperidine-4-carbonyl]-4-piperidyl]methyl]pyrrolo[2,3-d]pyrimidin-4-one (EXAMPLE 152)

Using General Procedure 7 starting from EXAMPLE 142 and methyl iodide as reagents, EXAMPLE 152 was obtained. HRMS calculated for $C_{31}H_{34}N_5O_3Cl$: 559.235; found 560.2425 [(M+H) form].

7-(4-chlorophenyl)-3-[[4-hydroxy-1-[(3R,4R)-1-methyl-3-phenyl-piperidine-4-carbonyl]-4-piperidyl]methyl]pyrrolo[2,3-d]pyrimidin-4-one (EXAMPLE 153)

Using General Procedure 7 starting from EXAMPLE 143 and methyl iodide as reagents, EXAMPLE 153 was obtained. HRMS calculated for $C_{31}H_{34}N_5O_3Cl$: 559.235; found 560.2423 [(M+H) form].

7-[(4-chlorophenyl)methyl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 154)

Using General Procedure 6 starting from EXAMPLE 56 as reagent, EXAMPLE 154 was obtained. HRMS calculated for $C_{31}H_{34}ClN_5O_3$: 559.235; found 560.2418 [(M+H) form].

7-[(3-chlorophenyl)methyl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 155)

Using General Procedure 6 starting from EXAMPLE 55 as reagent, EXAMPLE 155 was obtained. HRMS calculated for $C_{31}H_{34}ClN_5O_3$: 559.235; found 560.2432 [(M+H) form].

7-[(2-chlorophenyl)methyl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 156)

Using General Procedure 6 starting from EXAMPLE 54 as reagent, EXAMPLE 156 was obtained. HRMS calculated for $C_{31}H_{34}ClN_5O_3$: 559.235; found 560.2429 [(M+H) form].

7-(4-fluoro-3-methoxy-phenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 157)

Using General Procedure 6 starting from EXAMPLE 57 as reagent, EXAMPLE 157 was obtained. HRMS calculated for $C_{31}H_{34}FN_5O_4$: 559.2595; found 560.2638 [(M+H) form].

7-[4-(difluoromethyl)phenyl]-3-[[4-hydroxy-1-[(3R,4R)-3-phenylpiperidine-4-carbonyl]-4-piperidyl]methyl]pyrrolo[2,3-d]pyrimidin-4-one (EXAMPLE 158)

Using General Procedure 6 starting from EXAMPLE 58 as reagent, EXAMPLE 158 was obtained. HRMS calculated for $C_{31}H_{33}F2N_5O_3$: 561.2551; found 562.2636 [(M+H) form].

3-[[4-hydroxy-1-[(3R,4R)-3-phenylpiperidine-4-carbonyl]-4-piperidyl]methyl]-7-(2-naphthyl)pyrrolo[2,3-d]pyrimidin-4-one (EXAMPLE 159)

Using General Procedure 6 starting from EXAMPLE 60 as reagent, EXAMPLE 159 was obtained. HRMS calculated for $C_{34}H_{35}N_5O_3$: 561.274; found 562.2831 [(M+H) form].

3-[[4-hydroxy-1-[(3R,4R)-3-phenylpiperidine-4-carbonyl]-4-piperidyl]methyl]-7-(1-naphthyl)pyrrolo[2,3-d]pyrimidin-4-one (EXAMPLE 160)

Using General Procedure 6 starting from EXAMPLE 59 as reagent, EXAMPLE 160 was obtained. HRMS calculated for $C_{34}H_{35}N_5O_3$: 561.274; found 562.2827 [(M+H) form].

7-(4-chloro-3-fluoro-phenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 161)

Using General Procedure 6 starting from EXAMPLE 61 as reagent, EXAMPLE 161 was obtained. HRMS calculated for $C_{30}H_{31}N_5O_3FCl$: 563.21; found 564.2181 [(M+H) form].

3-[[4-hydroxy-1-[(3R,4R)-3-phenylpiperidine-4-carbonyl]-4-piperidyl]methyl]-7-(2-trimethylsilylethoxymethyl)pyrrolo[2,3-d]pyrimidin-4-one (EXAMPLE 162)

EXAMPLE 62 (1.6 g, 2.4 mmol) was dissolved in 30 ml DCM, then TFA (3 ml) and formic acid (550 µl, 7.2 mmol, 3 eq.) were added. The mixture was stirred at r.t. for 4 days, then potassium carbonate (15 g, 108 mmol) was added. The solution was extrated with DCM and organic phase was dried (MgSO$_4$) and evaporated to give EXAMPLE 162. HRMS calculated for $C_{30}H_{43}N_5O_4Si$: 565.3084; found 566.3138 [(M+H) form].

3-[[4-hydroxy-1-[(3R,4R)-1-isobutyl-3-phenyl-piperidine-4-carbonyl]-4-piperidyl]methyl]-7-phenyl-pyrrolo[2,3-d]pyrimidin-4-one (EXAMPLE 163)

Using General Procedure 7 starting from EXAMPLE 101 and 1-bromo-2-methyl-propane as reagents, EXAMPLE 163 was obtained. HRMS calculated for $C_{34}H_{41}N_5O_3$: 567.3209; found 568.328 [(M+H) form].

7-(2,3-dihydro-1,4-benzodioxin-6-yl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 164)

Using General Procedure 6 starting from EXAMPLE 63 as reagent, EXAMPLE 164 was obtained. HRMS calculated for $C_{32}H_{35}N_5O_5$: 569.2638; found 570.2709 [(M+H) form].

1-(2,3-dihydro-1,4-benzodioxin-6-yl)-5-[[4-hydroxy-1-[(3R,4R)-3-phenylpiperidine-4-carbonyl]-4-piperidyl]methyl]pyrazolo[3,4-d]pyrimidin-4-one (EXAMPLE 165)

Using General Procedure 6 starting from EXAMPLE 64 as reagent, EXAMPLE 165 was obtained. HRMS calculated for $C_{31}H_{34}N_6O_5$: 570.2591; found 571.2663 [(M+H) form].

3-[[1-[(3R,4R)-1-acetyl-3-phenyl-piperidine-4-carbonyl]-4-hydroxy-4-piperidyl]methyl]-7-(4-fluorophenyl)pyrrolo[2,3-d]pyrimidin-4-one (EXAMPLE 166)

Using General Procedure 8 starting from EXAMPLE 130 and acetic acid as reagents, EXAMPLE 166 was obtained. HRMS calculated for $C_{32}H_{34}FN_5O_4$: 571.2595; found 572.2679 [(M+H) form].

7-(3,5-dimethoxyphenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 167)

Using General Procedure 6 starting from EXAMPLE 66 as reagent, EXAMPLE 167 was obtained. HRMS calculated for $C_{32}H_{37}N_5O_5$: 571.2795; found 572.2881 [(M+H) form].

7-(3,4-dimethoxyphenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 168)

Using General Procedure 6 starting from EXAMPLE 65 as reagent, EXAMPLE 168 was obtained. HRMS calculated for $C_{32}H_{37}N_5O_5$: 571.2795; found 572.2892 [(M+H) form].

5-[[1-[(3R,4R)-1,1-dimethyl-3-phenyl-piperidin-1-ium-4-carbonyl]-4-hydroxy-4-piperidyl]methyl]-1-(4-methoxyphenyl)pyrazolo[3,4-d]pyrimidin-4-one (EXAMPLE 169)

Using General Procedure 7 starting from EXAMPLE 135 and methyl iodide as reagents, EXAMPLE 169 was obtained. HRMS calculated for $C_{32}H_{39}N_6O_4$: 571.3027; found 571.3038 [(M+) form].

3-[[4-hydroxy-1-[(3R,4R)-3-phenylpiperidine-4-carbonyl]-4-piperidyl]methyl]-6-iodo-7-methyl-pyrrolo[2,3-d]pyrimidin-4-one (EXAMPLE 170)

Using General Procedure 6 starting from EXAMPLE 67 as reagent, EXAMPLE 170 was obtained. HRMS calculated for $C_{25}H_{30}IN_5O_3$: 575.1393; found 576.1455 [(M+H) form].

7-(3-chloro-5-methoxy-phenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 171)

Using General Procedure 6 starting from EXAMPLE 68 as reagent, EXAMPLE 171 was obtained. HRMS calculated for $C_{31}H_{34}ClN_5O_4$: 575.2299; found 576.2382 [(M+H) form].

7-(4-chloro-3-methoxy-phenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 172)

Using General Procedure 6 starting from EXAMPLE 69 as reagents, EXAMPLE 172 was obtained. HRMS calculated for $C_{31}H_{34}ClN_5O_4$: 575.2299; found 576.2382 [(M+H) form].

7-(3,5-dichlorophenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 173)

Using General Procedure 6 starting from EXAMPLE 71 as reagent, EXAMPLE 173 was obtained. HRMS calculated for $C_{30}H_{31}N_5O_3Cl_2$: 579.1804; found 580.1891 [(M+H) form].

7-(3,4-dichlorophenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 174)

Using General Procedure 6 starting from EXAMPLE 70 as reagent, EXAMPLE 174 was obtained. HRMS calculated for $C_{30}H_{31}Cl_2N_5O_3$: 579.1804; found 580.187 [(M+H) form].

3-[[4-hydroxy-1-[(3R,4R)-3-phenylpiperidine-4-carbonyl]-4-piperidyl]methyl]-7-[4-(trifluoromethyl)phenyl]pyrrolo[2,3-d]pyrimidin-4-one (EXAMPLE 175)

Using General Procedure 6 starting from EXAMPLE 72 as reagent, EXAMPLE 175 was obtained. HRMS calculated for $C_{31}H_{32}N_5O_3F_3$: 579.2457; found 580.2529 [(M+H) form].

3-[[4-hydroxy-1-[(3R,4R)-3-phenylpiperidine-4-carbonyl]-4-piperidyl]methyl]-7-[3-(trifluoromethyl)phenyl]pyrrolo[2,3-d]pyrimidin-4-one (EXAMPLE 176)

Using General Procedure 6 starting from EXAMPLE 73 as reagent, EXAMPLE 176 was obtained. HRMS calculated for $C_{31}H_{32}F_3N_5O_3$: 579.2457; found 580.2509 [(M+H) form].

3-[[4-hydroxy-1-[(3R,4R)-1-(2-methylpropanoyl)-3-phenyl-piperidine-4-carbonyl]-4-piperidyl]methyl]-7-phenyl-pyrrolo[2,3-d]pyrimidin-4-one (EXAMPLE 177)

Using General Procedure 8 starting from EXAMPLE 101 and 2-methylpropanoic acid as reagents, EXAMPLE 177 was obtained. HRMS calculated for $C_{34}H_{39}N_5O_4$: 581.3002; found 582.3072 [(M+H) form].

3-[[1-[(3R,4R)-1-acetyl-3-phenyl-piperidine-4-carbonyl]-4-hydroxy-4-piperidyl]methyl]-7-(4-methoxyphenyl)pyrrolo[2,3-d]pyrimidin-4-one (EXAMPLE 178)

Using General Procedure 8 starting from EXAMPLE 135 and acetic acid as reagents, EXAMPLE 178 was obtained. HRMS calculated for $C_{33}H_{37}N_5O_5$: 583.2795; found 584.2868 [(M+H) form].

3-[[1-[(3R,4R)-1-acetyl-3-phenyl-piperidine-4-carbonyl]-4-hydroxy-4-piperidyl]methyl]-7-(3-methoxyphenyl)pyrrolo[2,3-d]pyrimidin-4-one (EXAMPLE 179)

Using General Procedure 8 starting from EXAMPLE 136 and acetic acid as reagents, EXAMPLE 179 was obtained. HRMS calculated for $C_{33}H_{37}N_5O_5$: 583.2795; found 584.2863 [(M+H) form].

3-[[1-[(3R,4R)-1-acetyl-3-phenyl-piperidine-4-carbonyl]-4-hydroxy-4-piperidyl]methyl]-7-(3-chlorophenyl)pyrrolo[2,3-d]pyrimidin-4-one (EXAMPLE 180)

Using General Procedure 8 starting from EXAMPLE 142 and acetic acid as reagents, EXAMPLE 180 was obtained. HRMS calculated for $C_{32}H_{34}ClN_5O_4$: 587.2299; found 588.238 [(M+H) form].

3-[[1-[(3R,4R)-1-acetyl-3-phenyl-piperidine-4-carbonyl]-4-hydroxy-4-piperidyl]methyl]-7-(4-chlorophenyl)pyrrolo[2,3-d]pyrimidin-4-one (EXAMPLE 181)

Using General Procedure 8 starting from EXAMPLE 143 and acetic acid as reagents, EXAMPLE 181 was obtained. HRMS calculated for $C_{32}H_{34}ClN_5O_4$: 587.2299; found 588.2366 [(M+H) form].

3-[[4-hydroxy-1-[(3R,4R)-3-phenylpiperidine-4-carbonyl]-4-piperidyl]methyl]-7-[4-(trifluoromethoxy)phenyl]pyrrolo[2,3-d]pyrimidin-4-one (EXAMPLE 182)

Using General Procedure 6 starting from EXAMPLE 76 as reagent, EXAMPLE 182 was obtained. HRMS calculated for $C_{31}H_{32}N_5O_4F_3$: 595.2407; found 596.2494 [(M+H) form].

3-[[4-hydroxy-1-[(3R,4R)-3-phenylpiperidine-4-carbonyl]-4-piperidyl]methyl]-7-[3-(trifluoromethoxy)phenyl]pyrrolo[2,3-d]pyrimidin-4-one (EXAMPLE 183)

Using General Procedure 6 starting from EXAMPLE 75 as reagent, EXAMPLE 183 was obtained. HRMS calculated for $C_{31}H_{32}N_5O_4F_3$: 595.2407; found 596.2491 [(M+H) form].

3-[[1-[(3R,4R)-1-(2,2-dimethylpropanoyl)-3-phenyl-piperidine-4-carbonyl]-4-hydroxy-4-piperidyl]methyl]-7-phenyl-pyrrolo[2,3-d]pyrimidin-4-one (EXAMPLE 184)

Using General Procedure 8 starting from EXAMPLE 101 and 2,2-dimethylpropanoic acid as reagents, EXAMPLE 184 was obtained. HRMS calculated for $C_{35}H_{41}N_5O_4$: 595.3159; found 596.3221 [(M+H) form].

3-[[4-hydroxy-1-[(3R,4R)-3-phenylpiperidine-4-carbonyl]-4-piperidyl]methyl]-7-(3-morpholinophenyl)pyrrolo[2,3-d]pyrimidin-4-one (EXAMPLE 185)

Using General Procedure 6 starting from EXAMPLE 77 as reagent, EXAMPLE 185 was obtained. HRMS calculated for $C_{34}H_{40}N_6O_4$: 596.3111; found 597.3187 [(M+H) form].

3-[[4-hydroxy-1-[(3R,4R)-3-phenylpiperidine-4-carbonyl]-4-piperidyl]methyl]-7-(3,4,5-trimethoxyphenyl)pyrrolo[2,3-d]pyrimidin-4-one (EXAMPLE 186)

Using General Procedure 6 starting from EXAMPLE 78 as reagent, EXAMPLE 186 was obtained. HRMS calculated for $C_{33}H_{39}N_5O_6$: 601.29; found 602.296 [(M+H) form].

3-[[1-[(3R,4R)-1-(3,3-dimethylbutanoyl)-3-phenyl-piperidine-4-carbonyl]-4-hydroxy-4-piperidyl]methyl]-7-phenyl-pyrrolo[2,3-d]pyrimidin-4-one (EXAMPLE 187)

Using General Procedure 8 starting from EXAMPLE 101 and 3,3-dimethylbutanoic acid as reagents, EXAMPLE 187 was obtained. HRMS calculated for $C_{36}H_{43}N_5O_4$: 609.3315; found 610.3384 [(M+H) form].

7-(4-benzyloxyphenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 188)

Using General Procedure 6 starting from EXAMPLE 79 as reagent, EXAMPLE 188 was obtained. HRMS calculated for $C_{37}H_{39}N_5O_4$: 617.3002; found 618.3083 [(M+H) form].

7-(3-benzyloxyphenyl)-3-[[4-hydroxy-1-[(3R,4R)-3-phenylpiperidine-4-carbonyl]-4-piperidyl]methyl]pyrrolo[2,3-d]pyrimidin-4-one (EXAMPLE 189)

Using General Procedure 6 starting from EXAMPLE 80 as reagent, EXAMPLE 189 was obtained. HRMS calculated for $C_{37}H_{39}N_5O_4$: 617.3002; found 618.3051 [(M+H) form].

3-[[4-hydroxy-1-[(3R,4R)-3-phenylpiperidine-4-carbonyl]-4-piperidyl]methyl]-7-[3-[(4-methylpiperazin-1-yl)methyl]phenyl]pyrrolo[2,3-d]pyrimidin-4-one (EXAMPLE 190)

Using General Procedure 6 starting from EXAMPLE 81 as reagent, EXAMPLE 190 was obtained. HRMS calculated for $C_{36}H_{45}N_7O_3$: 623.3584; found 624.3656 [(M+H) form].

3-[[4-hydroxy-1-[(3R,4R)-3-phenylpiperidine-4-carbonyl]-4-piperidyl]methyl]-7-phenyl-thieno[3,4-d]pyrimidin-4-one (EXAMPLE 191)

Using General Procedure 6 starting from EXAMPLE 127 as reagent, EXAMPLE 191 was obtained. HRMS calculated for $C_{30}H_{32}N_4O_3S$: 528.2195; found 529.2265 [(M+H) form].

3-[[4-hydroxy-1-[(3R,4R)-3-phenylpiperidine-4-carbonyl]-4-piperidyl]methyl]-6-iodo-7-(2-trimethylsilylethoxymethyl)pyrrolo[2,3-d]pyrimidin-4-one (EXAMPLE 192)

EXAMPLE 74 (647 mg, 0.82 mmol) was dissolved in 13 ml DCM, then TFA (188 µl, 2.46 mmol, 3 eq.) and formic acid (356 µl, 9.43 mmol, 11.5 eq.) were added. The mixture was stirred at r.t. for 214 hours, then potassium carbonate (1.99 g, 14.3 mmol) was added. The solution was extrated with DCM (2×70 ml) and organic phase ($MgSO_4$) was dried and evaporated to give EXAMPLE 192. HRMS calculated for $C_{30}H_{42}IN_5O_4Si$: 691.2051; found 692.2155 [(M+H) form].

tert-butyl (3R,4R)-4-[4-hydroxy-4-[(4-oxopyrido[3,2-d]pyrimidin-3-yl)methyl]piperidine-1-carbonyl]-3-phenyl-piperidine-1-carboxylate (EXAMPLE 193)

Using General Procedure 5 starting from 3H-pyrido[3,2-d]pyrimidin-4-one and Preparation R1c as reagents, EXAMPLE 193 was obtained. HRMS calculated for $C_{30}H_{37}N_5O_5$: 547.2795; found 548.2870 [(M+H) form].

3-[[4-hydroxy-1-[(3R,4R)-3-phenylpiperidine-4-carbonyl]-4-piperidyl]methyl]pyrido[3,2-d]pyrimidin-4-one (EXAMPLE 194)

Using General Procedure 6 starting from EXAMPLE 193 as reagent, EXAMPLE 194 was obtained as HCl salt. HRMS calculated for $C_{25}H_{29}N_5O_3$: 447.227; found 448.2365 [(M+H)$^+$ form].

tert-butyl (3R,4R)-4-[4-[(6-chloro-4-oxo-pyrido[3,2-d]pyrimidin-3-yl)methyl]-4-hydroxy-piperidine-1-carbonyl]-3-phenyl-piperidine-1-carboxylate (EXAMPLE 195)

Using General Procedure 5 starting from 6-chloro-3H-pyrido[3,2-d]pyrimidin-4-one and Preparation R1c as reagents, EXAMPLE 195 was obtained. HRMS calculated for $C_{30}H_{36}ClN_5O_5$: 581.2405; found 604.2239 [(M+Na) form].

6-chloro-3-[[4-hydroxy-1-[(3R,4R)-3-phenylpiperidine-4-carbonyl]-4-piperidyl]methyl]pyrido[3,2-d]pyrimidin-4-one (EXAMPLE 196)

Using General Procedure 6 starting from EXAMPLE 195 as reagent, EXAMPLE 196 was obtained as HCl salt. HRMS calculated for $C_{25}H_{28}ClN_5O_3$: 481.1881; found 482.1949 [(M+H)$^+$ form].

tert-butyl (3R,4R)-4-[4-hydroxy-4-[(6-methoxy-4-oxo-pyrido[3,2-d]pyrimidin-3-yl)methyl]piperidine-1-carbonyl]-3-phenyl-piperidine-1-carboxylate (EXAMPLE 197)

Using General Procedure 5 starting from 6-methoxy-3H-pyrido[3,2-d]pyrimidin-4-one and Preparation R1c as reagents, EXAMPLE 197 was obtained. HRMS calculated for $C_{31}H_{39}N_5O_6$: 577.29; found 578.2976 [(M+H) form].

3-[[4-hydroxy-1-[(3R,4R)-3-phenylpiperidine-4-carbonyl]-4-piperidyl]methyl]-6-methoxy-pyrido[3,2-d]pyrimidin-4-one (EXAMPLE 198)

Using General Procedure 6 starting from EXAMPLE 197 as reagent, EXAMPLE 198 was obtained as HCl salt. HRMS calculated for $C_{26}H_{31}N_5O_4$: 477.2376; found 478.2458 [(M+H)$^+$ form].

Pharmacological Study

Example A: Evaluation of the Inhibition of USP7 by the Fluorescence Intensity (FLINT) Readings USP7 activity was measured using Rhodamine-110 c-terminal labelled Ubiquitin as a substrate (Viva Biosciences). Incubation with USP7 results in the release of Rhodamine-110 leading to an increase in fluorescence which can be used in the continuous measurement of USP7 activity.

The USP7 reactions were performed in a 50 µL volume, in 384 well black solid low binding plates (Corning #3575). The reaction buffer consisted of 100 mM Bicine pH 8.0, 0.01% TritonX100, 1 mM TCEP, and 10% DMSO.

0.25 nM His-His-USP7 (aa208-560, [C315A]) was incubated with compound (final concentration 10% DMSO) for 60 minutes at 30° C. The reaction was then initiated by the addition of 500 nM Ubiquitin-Rhodamine-110 substrate and the plate read every 3 minutes for 21 minutes to measure the release of Rhodamine-110. Fluorescence Intensity (FLINT) readings were measured using a Biomek Neo plate reader (Ex.485 nm, Em.535 nm).

The inhibition of increasing doses of compound was expressed as a percentage reduction in kinetic rate compared to the kinetic rates established between 'DMSO only' and 'total inhibition' controls (no USP7). The inhibitory concentrations that gave a 50% reduction in kinetic rate ($IC_{50}$) were determined, from 11-point dose response curves, in XL-Fit using a 4-Parameter Logistic Model (Sigmoidal Dose-Response Model).

The results presented in Table 1 below show that compounds of the invention inhibit interaction between USP7 protein and the fluorescent peptide described hereinbefore.

Example B: In Vitro Cytotoxicity

The cytotoxicity studies were carried out on the MM1S multiple myeloma tumour cell line. The cells are distributed onto microplates and exposed to the test compounds for 96 hours. The cell viability is then quantified by a colorimetric assay, the Microculture Tetrazolium Assay (Cancer Res., 1987, 47, 939-942).

The results are expressed in $IC_{50}$ (the concentration of compound that inhibits cell viability by 50%) and are presented in Table 1 below.

The results show that the compounds of the invention are cytotoxic.

TABLE 1

$IC_{50}$ of USP7 inhibition and of cytotoxicity for MM1S cells

| EXAMPLE | $IC_{50}$ (M) USP7 FLINT | $IC_{50}$ (M) MTT MM1S |
|---|---|---|
| 2 | 1.28E−07 | ND |
| 15 | 2.74E−07 | ND |
| 40 | 4.99E−08 | 3.15E−08 |
| 44 | 6.15E−08 | ND |
| 57 | 7.02E−08 | ND |
| 64 | 6.87E−08 | ND |
| 101 | 3.16E−08 | 2.72E−07 |
| 103 | 5.29E−08 | ND |
| 104 | 3.94E−07 | ND |
| 117 | 1.20E−06 | ND |
| 121 | 1.40E−07 | ND |
| 130 | 3.77E−08 | ND |
| 135 | 2.87E−08 | 1.35E−07 |
| 136 | 4.86E−08 | ND |
| 141 | 7.48E−08 | ND |
| 142 | 5.67E−08 | ND |
| 143 | 4.12E−08 | ND |
| 147 | 4.06E−07 | ND |
| 151 | 5.24E−08 | ND |
| 152 | 6.48E−08 | ND |
| 153 | 4.86E−08 | 7.47E−08 |
| 157 | 3.93E−08 | ND |
| 163 | 1.08E−07 | ND |
| 165 | 1.96E−08 | 3.00E−07 |
| 166 | 1.02E−07 | ND |
| 169 | 8.60E−07 | ND |
| 177 | 1.03E−07 | ND |
| 178 | 9.61E−08 | ND |
| 179 | 8.84E−08 | ND |
| 180 | 8.90E−08 | ND |
| 181 | 7.42E−08 | ND |
| 184 | 8.30E−08 | ND |
| 187 | 8.85E−08 | ND |

ND: not determined

Example C: Anti-Tumor Activity In Vivo

The anti-tumour activity of the compounds of the invention is evaluated in a xenograft model of multiple myeloma and/or acute lymphoblastic leukaemia cells.

Human tumour cells are grafted subcutaneously into immunosuppressed mice.

When the tumour volume (TV) reaches about 200 mm³, the mice are treated per os with the various compounds once a day for 5 days on/2 days off during 3 weeks. The tumour mass is measured twice weekly from the start of treatment.

The compounds of the invention display anti-tumour activities represented by the TGI (tumor growth inhibition) at the end of the treatment period. The TGI is defined as follows:

$$TGI = \left(1 - \frac{\text{Median } (DTV \text{ at } Dx \text{ in treated group})}{\text{Median } (DTV \text{ at } Dx \text{ in control group})}\right) \times 100,$$

with:

DTV (delta tumoral volume) at $Dx$=(TV at $Dx$)−(TV at randomization for each animal).

Example D: Pharmaceutical Composition: Tablets

| | |
|---|---|
| 1000 tablets containing a dose of 5 mg of a compound selected from Examples 1 to 198 | 5 g |
| Wheat starch | 20 g |
| Maize starch | 20 g |
| Lactose | 30 g |
| Magnesium stearate | 2 g |
| Silica | 1 g |
| Hydroxypropylcellulose | 2 g |

The invention claimed is:

1. A compound of formula (I):

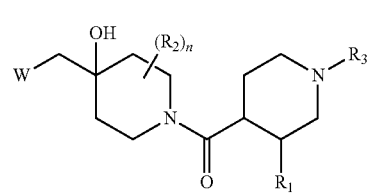

or a pharmaceutically acceptable addition salt, enantiomer, or diastereomer thereof, wherein:

W represents

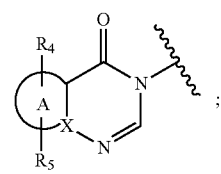

A represents a monocyclic aromatic ring or fused bicyclic ring comprising 5, 6, 7, 8, 9, or 10 ring members, wherein the monocyclic aromatic ring or fused bicyclic ring has 1, 2, or 3 heteroatoms independently selected from the group consisting of nitrogen, oxygen, and sulfur, and further wherein the fused bicyclic ring has at least one aromatic moiety, and the monocyclic aromatic ring or fused bicyclic ring is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$NR'R", $Y_1$NR'C(O)R", $Y_1$NR'C(O)OR", $Y_1$OR', OC(O)R', $Y_1$S(O)$_m$R', cyclopropyl, and pyridinyl, wherein the pyridinyl substituent is optionally substituted by a $(C_1-C_6)$alkyl substituent;

X represents C or N;

$R_1$ represents:

(i) phenyl, indanyl, or naphthyl, wherein the phenyl, indanyl, or naphthyl is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$NR'R", $Y_1$NR'C(O)R", $Y_1$NR'C(O)OR", $Y_1$OR', OC(O)R', $Y_1$S(O)$_m$R', cyclopropyl, and pyridinyl, and further wherein the pyridinyl substituent is optionally substituted by a $(C_1-C_6)$alkyl substituent; or (ii) a monocyclic aromatic ring or fused bicyclic ring comprising 5, 6, 7, 8, 9, or 10 ring members, wherein the monocyclic aromatic ring or fused bicyclic ring has 1, 2, or 3 heteroatoms independently selected from the group consisting of nitrogen, oxygen, and sulfur, and further wherein the fused bicyclic ring has at least one aromatic moiety, and the monocyclic aromatic ring or fused bicyclic ring is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$NR'R", $Y_1$NR'C(O)R", $Y_1$NR'C(O)OR", $Y_1$OR', OC(O)R', $Y_1$S(O)$_m$R', cyclopropyl, and pyridinyl, wherein the pyridinyl substituent is optionally substituted by a $(C_1-C_6)$alkyl substituent;

$R_2$ represents hydrogen or halogen;

$R_3$ represents hydrogen, $(C_1-C_6)$alkyl, halo$(C_1-C_6)$alkyl, C(O)$R_8$, or C(O)O$R_8$;

each $R_4$ independently represents hydrogen, halogen, oxo, $(C_1-C_6)$alkyl, halo$(C_1-C_6)$alkyl, $(C_2-C_6)$alkenyl, $(C_2-C_6)$alkynyl, $Y_1$NR$_6$R$_7$, $Y_1$NR$_6$C(O)R$_7$, $Y_1$OR$_6$, $Y_1$Cy$_1$, Cy$_1$R$_7$, or Cy$_1$OR$_7$;

each $R_5$ independently represents hydrogen, halogen, cyano, $(C_1-C_6)$alkyl, halo$(C_1-C_6)$alkyl, or hydroxy$(C_1-C_6)$alkyl;

each $R_6$ independently represents hydrogen, $(C_1-C_6)$alkyl, halo$(C_1-C_6)$alkyl, or $Y_2$Si[$(C_1-C_4)$alkyl]$_3$;

each $R_7$ independently represents hydrogen, $(C_1-C_6)$alkyl, or $Y_2$Cy$_2$;

$R_8$ represents hydrogen or $(C_1-C_6)$alkyl;

each Cy$_1$ independently represents:

(i) a monocyclic or fused bicyclic non-aromatic carbocyclic ring comprising 3, 4, 5, 6, or 7 ring members, wherein the monocyclic or fused bicyclic non-aromatic carbocyclic ring is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$NR'R", $Y_1$NR' C(O)R", $Y_1$NR' C(O)OR", $Y_1$OR', OC(O)R', $Y_1$S(O)$_m$R', cyclopropyl, and pyridinyl, and further wherein the pyridinyl substituent is optionally substituted by a $(C_1-C_6)$alkyl substituent;

(ii) a monocyclic or fused bicyclic non-aromatic ring comprising 3, 4, 5, 6, 7, 8, 9, or 10 ring members, wherein the monocyclic or fused bicyclic ring has 1, 2, or 3 heteroatoms independently selected from the group consisting of nitrogen, oxygen, and sulfur, and further wherein the mono cyclic or fused bicyclic non-aromatic ring is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$NR'R", $Y_1$NR'C(O)R", $Y_1$NR'C(O)OR", $Y_1$OR', OC(O)R', $Y_1$S(O)$_m$R', cyclopropyl, and pyridinyl, wherein the pyridinyl substituent is optionally substituted by a $(C_1-C_6)$alkyl substituent;

(iii) phenyl, indanyl, or naphthyl, wherein the phenyl, indanyl, or naphthyl is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$NR'R", $Y_1$ NR' C(O)R", $Y_1$NR' C(O)OR", $Y_1$OR', OC(O)R', $Y_1$S(O)$_m$R', cyclopropyl, and pyridinyl, and further wherein the pyridinyl substituent is optionally substituted by a $(C_1-C_6)$alkyl substituent; or (iv) a monocyclic aromatic ring or fused bicyclic ring comprising 5, 6, 7, 8, 9, or 10 ring members, wherein the monocyclic aromatic ring or fused bicyclic ring has 1, 2, or 3 heteroatoms independently selected from the group consisting of nitrogen, oxygen, and sulfur, and further wherein the fused bicyclic ring has at least one aromatic moiety, and the monocyclic aromatic ring or fused bicyclic ring is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$NR'R", $Y_1$NR'C(O)R", $Y_1$NR'C(O)OR", $Y_1$OR', OC(O)R', $Y_1$S(O)$_m$R', cyclopropyl, and pyridinyl, wherein the pyridinyl substituent is optionally substituted by a $(C_1-C_6)$alkyl substituent;

each Cy$_2$ independently represents:

(i) a monocyclic or fused bicyclic non-aromatic carbocyclic ring comprising 3, 4, 5, 6, or 7 ring members, wherein the monocyclic or fused bicyclic non-aromatic carbocyclic ring is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$ NR'R", $Y_1$NR'C(O)R", $Y_1$NR'C(O)OR", $Y_1$OR', OC(O)R', $Y_1$S(O)$_m$R', cyclopropyl, and pyridinyl, and further wherein the pyridinyl substituent is optionally substituted by a $(C_1-C_6)$alkyl substituent;

(ii) a monocyclic or fused bicyclic non-aromatic ring comprising 3, 4, 5, 6, 7, 8, 9, or 10 ring members, wherein the monocyclic or fused bicyclic ring has 1, 2, or 3 heteroatoms independently selected from the group consisting of nitrogen, oxygen, and sulfur, and further wherein the mono cyclic or fused bicyclic non-aromatic ring is optionally substituted by 1, 2, 3, or 4 substituents independently selected from the group consisting of halogen, nitro, cyano, oxo, $(C_1-C_6)$alkyl, halo$(C_1-C_6)$alkyl, $(C_2-C_6)$alkenyl, $(C_2-C_6)$alkynyl, C(O)R', C(O)NR'R", C(O)OR', $Y_1$NR'R", $Y_1$NR'C(O)R", $Y_1$NR'C (O)OR", Y₁OR', OC(O)R', Y₁S(O)ₘR', cyclopropyl, and pyridinyl, wherein the pyridinyl substituent is optionally substituted by a (C₁-C₆)alkyl substituent;

(iii) phenyl, indanyl, or naphthyl, wherein the phenyl, indanyl, or naphthyl is optionally substituted by 1, 2, 3, or 4 substituents independently selected from the group consisting of halogen, nitro, cyano, oxo, (C₁-C₆)alkyl, halo(C₁-C₆)alkyl, (C₂-C₆)alkenyl, (C₂-C₆)alkynyl, C(O)R', C(O)NR'R", C(O)OR', Y₁NR'R", Y₁NR'C(O)R", Y₁NR'C(O)OR", Y₁OR', OC(O)R', Y₁S(O)ₘR', cyclopropyl, and pyridinyl, and further wherein the pyridinyl substituent is optionally substituted by a (C₁-C₆)alkyl substituent; or (iv) a monocyclic aromatic ring or fused bicyclic ring comprising 5, 6, 7, 8, 9, or 10 ring members, wherein the monocyclic aromatic ring or fused bicyclic ring has 1, 2, or 3 heteroatoms independently selected from the group consisting of nitrogen, oxygen, and sulfur, and further wherein the fused bicyclic ring has at least one aromatic moiety, and the monocyclic aromatic ring or fused bicyclic ring is optionally substituted by 1, 2, 3, or 4 substituents independently selected from the group consisting of halogen, nitro, cyano, oxo, (C₁-C₆)alkyl, halo(C₁-C₆)alkyl, (C₂-C₆)alkenyl, (C₂-C₆)alkynyl, C(O)R', C(O)NR'R", C(O)OR', Y₁NR'R", Y₁NR'C(O)R", Y₁NR'C(O)OR", Y₁OR', OC(O)R', Y₁S(O)ₘR', cyclopropyl, and pyridinyl, wherein the pyridinyl substituent is optionally substituted by a (C₁-C₆)alkyl substituent;

each $Y_1$ independently represents a bond or —(C₁-C₄)alkylene;

each $Y_2$ independently represents a bond or —(C₁-C₄)alkylene;

each R' independently represents hydrogen, (C₁-C₆)alkyl, halo(C₁-C₆)alkyl, hydroxy(C₁-C₆)alkyl, (C₁-C₆)alkoxy(C₁-C₆)alkyl, cyclopropylmethyl, (C₂-C₆)alkenyl, (C₁-C₆)alkoxy, tetrahydropyranyl, or phenyl;

each R" independently represents hydrogen, (C₁-C₆)alkyl, halo(C₁-C₆)alkyl, hydroxy(C₁-C₆)alkyl, (C₁-C₆)alkoxy(C₁-C₆)alkyl, cyclopropylmethyl, (C₂-C₆)alkenyl, (C₁-C₆)alkoxy, tetrahydropyranyl, or phenyl; or each R' and R", together with the nitrogen atom to which they are attached, independently represents a non-aromatic ring comprising 5, 6, or 7 ring members, wherein the non-aromatic ring optionally has 1 additional heteroatom selected from the group consisting of nitrogen and oxygen, and further wherein the optional additional nitrogen heteroatom is substituted by 1 or 2 substituents independently selected from the group consisting of hydrogen and (C₁-C₆)alkyl;

m is 0, 1, or 2; and n is 0, 1, or 2.

2. The compound according to claim 1, or a pharmaceutically acceptable addition salt, enantiomer, or diastereomer thereof, wherein W represents:

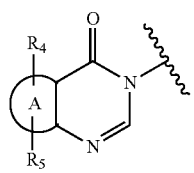

3. The compound according to claim 1, or a pharmaceutically acceptable addition salt, enantiomer, or diastereomer thereof, wherein W represents:

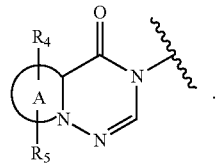

4. The compound according to claim 1, or a pharmaceutically acceptable addition salt, enantiomer, or diastereomer thereof, wherein $R_1$ represents phenyl.

5. The compound according to claim 1, or a pharmaceutically acceptable addition salt, enantiomer, or diastereomer thereof, wherein $R_2$ represents hydrogen.

6. The compound according to claim 1, or a pharmaceutically acceptable addition salt, enantiomer, or diastereomer thereof, wherein $R_3$ represents hydrogen, CH₃, CH₂CH(CH₃)₂, CH₂CF₃, C(O)CH₃, C(O)CH(CH₃)₂, C(O)CH₂C(CH₃)₃, or C(O)OC(CH₃)₃.

7. The compound according to claim 1, or a pharmaceutically acceptable addition salt, enantiomer, or diastereomer thereof, wherein each $R_4$ independently represents hydrogen, (C₁-C₆)alkyl, halo(C₁-C₆)alkyl, (C₂-C₆)alkenyl, (C₂-C₆)alkynyl, Y₁NR₆R₇, Y₁OR₆, Y₁Cy₁, Cy₁R₇, or Cy₁OR₇.

8. The compound according to claim 1, or a pharmaceutically acceptable addition salt, enantiomer, or diastereomer thereof, wherein each $R_5$ independently represents hydrogen, iodo, chloro, CH₃, or CH₂OH.

9. The compound according to claim 1, or a pharmaceutically acceptable addition salt, enantiomer, or diastereomer thereof, wherein each $R_6$ independently represents hydrogen, CH₃, or (CH₂)₂Si(CH₃)₃.

10. The compound according to claim 1, or a pharmaceutically acceptable addition salt, enantiomer, or diastereomer thereof, wherein each $R_7$ independently represents hydrogen, CH₃, or CH₂Cy₂.

11. The compound according to claim 1, or a pharmaceutically acceptable addition salt, enantiomer, or diastereomer thereof, wherein the compound, or pharmaceutically acceptable addition salt, enantiomer, or diastereomer thereof, is selected from the group consisting of:

tert-butyl (3S,4S)-4-({4-hydroxy-4-[(4-oxothieno [2,3-d]pyrimidin-3 (4H)-yl)methyl]piperidin-1-yl}carbonyl)-3-phenylpiperidine-1-carboxylate;

tert-butyl (3R,4R)-4-[(4-hydroxy-4-{[4-oxo-7-(pyridin-2-yl)-4,7-dihydro-3H-pyrrolo[2,3-d]pyrimidin-3-yl]methyl}piperidin-1-yl)carbonyl]-3-phenylpiperidine-1-carboxylate;

tert-butyl (3R,4R)-4-[(4-hydroxy-4-{[7-(4-methoxyphenyl)-4-oxo-4,7-dihydro-3H-pyrrolo [2,3-d]pyrimidin-3-yl]methyl}piperidin-1-yl)carbonyl]-3-phenylpiperidine-1-carboxylate;

tert-butyl (3R,4R)-4-[(4-hydroxy-4-{[1-(4-methoxyphenyl)-4-oxo-1,4-dihydro-5H-pyrazolo[3,4-d]pyrimidin-5-yl]methyl}piperidin-1-yl)carbonyl]-3-phenylpiperidine-1-carboxylate;

tert-butyl (3R,4R)-4-[(4-{[7-(4-fluoro-3-methoxyphenyl)-4-oxo-4,7-dihydro-3H-pyrrolo [2,3-d]pyrimidin-3-yl]methyl}-4-hydroxypiperidin-1-yl)carbonyl]-3-phenylpiperidine-1-carboxylate;

tert-butyl (3R,4R)-4-[(4-{[1-(2,3-dihydro-1,4-benzodioxin-6-yl)-4-oxo-1,4-dihydro-5H-pyrazolo [3,4-d]pyrimidin-5-yl]methyl}-4-hydroxypiperidin-1-yl)carbonyl]-3-phenylpiperidine-1-carboxylate;

3-[(4-hydroxy-1-{[(3R,4R)-3-phenylpiperidin-4-yl]carbonyl}piperidin-4-yl)methyl]-7-phenyl-3,7-dihydro-4H-pyrrolo[2,3-d]pyrimidin-4-one;

5-[(4-hydroxy-1-{[(3R,4R)-3-phenylpiperidin-4-yl]carbonyl}piperidin-4-yl)methyl]-1-phenyl-1,5-dihydro-4H-pyrazolo[3,4-d]pyrimidin-4-one;

3-[(4-hydroxy-1-{[(3R,4R)-3-phenylpiperidin-4-yl]carbonyl}piperidin-4-yl)methyl]-7-(pyridin-2-yl)-3,7-dihydro-4H-pyrrolo[2,3-d]pyrimidin-4-one;

3-[(4-hydroxy-1-{[(3R,4R)-3-phenyl-1-(2,2,2-trifluoroethyl)piperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-methyl-3-phenylpiperidin-4-yl]carbonyl}piperidin-4-yl)methyl]-7-phenyl-3,7-dihydro-4H-pyrrolo[2,3-d]pyrimidin-4-one;

7-(4-fluorophenyl)-3-[(4-hydroxy-1-{[(3R,4R)-3-phenylpiperidin-4-yl]carbonyl}piperidin-4-yl)methyl]-3,7-dihydro-4H-pyrrolo[2,3-4pyrimidin-4-one;

3-[(4-hydroxy-1-{[(3R,4R)-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

3-[(4-hydroxy-1-{[(3R,4R)-3-phenylpiperidin-4-yl]carbonyl}piperidin-4-yl)methyl]-7-(3-methoxyphenyl)-3,7-dihydro-4H-pyrrolo[2,3-d]pyrimidin-4-one;

7-(4-fluorophenyl)-3-[(4-hydroxy-1-{[(3R,4R)-1-methyl-3-phenylpiperidin-4-yl]carbonyl}piperidin-4-yl)methyl]-3,7-dihydro-4H-pyrrolo[2,3-d]pyrimidin-4-one;

7-(3-chlorophenyl)-3-[(4-hydroxy-1-{[(3R,4R)-3-phenylpiperidin-4-yl]carbonyl}piperidin-4-yl)methyl]-3,7-dihydro-4H-pyrrolo[2,3-d]pyrimidin-4-one;

7-(4-chlorophenyl)-3-[(4-hydroxy-1-{[(3R,4R)-3-phenylpiperidin-4-yl]carbonyl}piperidin-4-yl)methyl]-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-phenyl-3,7-dihydro-4H-pyrrolo[2,3-d]pyrimidin-4-one;

3-[(4-hydroxy-1-{[(3R,4R)-1-methyl-3-phenylpiperidin-4-yl]carbonyl}piperidin-4-yl)methyl]-7-(4-methoxyphenyl)-3,7-dihydro-4H-pyrrolo[2,3-d]pyrimidin-4-one;

7-(3-chlorophenyl)-3-[(4-hydroxy-1-{[(3R,4R)-1-methyl-3-phenylpiperidin-4-yl]carbonyl}piperidin-4-yl)methyl]-3,7-dihydro-4H-pyrrolo[2,3-d]pyrimidin-4-one;

7-(4-chlorophenyl)-3-[(4-hydroxy-1-{[(3R,4R)-1-methyl-3-phenylpiperidin-4-yl]carbonyl}piperidin-4-yl)methyl]-3,7-dihydro-4H-pyrrolo[2,3-d]pyrimidin-4-one;

7-(4-fluoro-3-methoxyphenyl)-3-[(4-hydroxy-1-{[(3R,4R)-3-phenylpiperidin-4-yl]carbonyl}piperidin-4-yl)methyl]-3,7-dihydro-4H-pyrrolo[2,3-d]pyrimidin-4-one;

3-[(4-hydroxy-1-{[(3R,4R)-1-(2-methylpropyl)-3-phenylpiperidin-4-yl]carbonyl} piperidin-4-yl)methyl]-7-phenyl-3,7-dihydro-4H-pyrrolo[2,3-d]pyrimidin-4-one;

1-(2,3-dihydro-1,4-benzodioxin-6-yl)-5-[(4-hydroxy-1-{[(3R,4R)-3-phenylpiperidin-4-yl]carbonyl}piperidin-4-yl)methyl]-1,5-dihydro-4H-pyrazolo[3,4-d]pyrimidin-4-one;

3-[(1-{[(3R,4R)-1-acetyl-3-phenylpiperidin-4-yl]carbonyl}-4-hydroxypiperidin-4-yl)methyl]-7-(4-fluorophenyl)-3,7-dihydro-4H-pyrrolo[2,3-d]pyrimidin-4-one;

(3R,4R)-4-[(4-hydroxy-4-{[1-(4-methoxyphenyl)-4-oxo-1,4-dihydro-5H-pyrazolo[3,4-d]pyrimidin-5-yl]methyl}piperidin-1-yl)carbonyl]-1,1-dimethyl-3-phenylpiperidinium;

3-[(4-hydroxy-1-{[(3R,4R)-1-(2-methylpropanoyl)-3-phenylpiperidin-4-yl]carbonyl} piperidin-4-yl)methyl]-7-phenyl-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-(4-methoxyphenyl)-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-(3-methoxyphenyl)-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-(3-chlorophenyl)-3,7-dihydro-4H-pyrrolo[2,3-d]pyrimidin-4-one;

3-[(1-{[(3R,4R)-1-acetyl-3-phenylpiperidin-4-yl]carbonyl}-4-hydroxypiperidin-4-yl)methyl]-7-(4-chlorophenyl)-3,7-dihydro-4H-pyrrolo[2,3-d]pyrimidin-4-one;

3-[(1-{[(3R,4R)-1-(2,2-dimethylpropanoyl)-3-phenylpiperidin-4-yl]carbonyl}-4-hydroxypiperidin-4-yl)methyl]-7-phenyl-3,7-dihydro-4H-pyrrolo [2,3-d]pyrimidin-4-one; and 3-[(1-{[(3R,4R)-1-(3,3-dimethylbutanoyl)-3-phenylpiperidin-4-yl]carbonyl}-4-hydroxypiperidin-4-yl)methyl]-7-phenyl-3,7-dihydro-4H-pyrrolo [2,3-d]pyrimidin-4-one.

12. A combination consisting of the compound according to claim 1, or a pharmaceutically acceptable addition salt, enantiomer, or diastereomer thereof, and an a cancer agent selected from the group consisting of an anti-metabolite, an antibody, a chimeric antigen receptor T-cell therapy, an E3 ligase inhibitor, a genotoxic agent, an immunomodulator, a kinase inhibitor, a mitotic poison, a proteasome inhibitor, and a protein-protein interaction inhibitor.

13. A pharmaceutical composition comprising the compound according to claim 1, or a pharmaceutically acceptable addition salt, enantiomer, or diastereomer thereof, and one or more pharmaceutically acceptable excipients.

14. A pharmaceutical composition comprising the combination according to claim 12 and one or more pharmaceutically acceptable excipients.

15. A method for treating acute myeloid leukemia, lymphoblastic leukemia, myeloma, bladder cancer, breast cancer, colon cancer, esophageal cancer, liver cancer, non-small-cell lung cancer, ovarian cancer, prostate cancer, or small-cell lung cancer in a subject in need thereof, comprising administering to the subject a therapeutically effective amount of the compound according to claim 1, or a pharmaceutically acceptable addition salt, enantiomer, or diastereomer thereof, or the pharmaceutical composition according to claim 13.

16. The method according to claim 15, wherein the method further comprises administering radiotherapy to the subject.

17. A method for treating acute myeloid leukemia, lymphoblastic leukemia, myeloma, bladder cancer, breast cancer, colon cancer, esophageal cancer, liver cancer, non-small-cell lung cancer, ovarian cancer, prostate cancer, or small-cell lung cancer in a subject in need thereof, comprising administering to the subject a therapeutically effective amount of the combination according to claim 12, or the pharmaceutical composition according to claim 14.

* * * * *

UNITED STATES PATENT AND TRADEMARK OFFICE
CERTIFICATE OF CORRECTION

PATENT NO. : 11,046,681 B2
APPLICATION NO. : 16/306933
DATED : June 29, 2021
INVENTOR(S) : András Kotschy et al.

Page 1 of 1

It is certified that error appears in the above-identified patent and that said Letters Patent is hereby corrected as shown below:

On the Title Page

Page 2
Column 1, Line 21, the last reference: Son should read Sun.

Signed and Sealed this
Thirty-first Day of August, 2021

Drew Hirshfeld
*Performing the Functions and Duties of the*
*Under Secretary of Commerce for Intellectual Property and*
*Director of the United States Patent and Trademark Office*